US010265355B2

(12) United States Patent
Yoon et al.

(10) Patent No.: US 10,265,355 B2
(45) Date of Patent: Apr. 23, 2019

(54) **SHIGATOXIN-PRODUCING F18 TYPE *E. COLI* BACTERIOPHAGE ESC-COP-1 AND USE THEREOF FOR INHIBITING PROLIFERATION OF SHIGATOXIN-PRODUCING F18 TYPE *E. COLI***

(71) Applicant: Intron Biotechnology, Inc., Gyeonggi-do (KR)

(72) Inventors: Seong Jun Yoon, Seoul (KR); Sang Hyeon Kang, Seoul (KR); Soo Youn Jun, Seoul (KR); Hyoun Rok Paik, Incheon (KR); Jee Soo Son, Seoul (KR); Suk Hwang Park, Gyeonggi-do (KR); Byung Kuk Kim, Gyeonggi-do (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 0 days.

(21) Appl. No.: 15/538,573

(22) PCT Filed: Dec. 28, 2015

(86) PCT No.: PCT/KR2015/014331
§ 371 (c)(1),
(2) Date: Jun. 21, 2017

(87) PCT Pub. No.: WO2016/108541
PCT Pub. Date: Jul. 7, 2016

(65) Prior Publication Data

US 2017/0340686 A1 Nov. 30, 2017

(30) Foreign Application Priority Data

Dec. 30, 2014 (KR) ........................ 10-2014-0192983

(51) Int. Cl.

| | |
|---|---|
| ***C12N 7/00*** | (2006.01) |
| ***A23K 10/16*** | (2016.01) |
| ***A61K 35/76*** | (2015.01) |
| ***C02F 3/34*** | (2006.01) |
| ***A23L 2/38*** | (2006.01) |
| ***A23L 2/52*** | (2006.01) |
| ***A23K 10/18*** | (2016.01) |
| ***A23K 50/30*** | (2016.01) |
| *C02F 103/02* | (2006.01) |

(52) U.S. Cl.
CPC .............. *A61K 35/76* (2013.01); *A23K 10/16* (2016.05); *A23K 10/18* (2016.05); *A23K 50/30* (2016.05); *A23L 2/38* (2013.01); *A23L 2/52* (2013.01); *C02F 3/34* (2013.01); *C12N 7/00* (2013.01); *A23V 2002/00* (2013.01); *C02F 2103/02* (2013.01); *C02F 2303/04* (2013.01); *C02F 2305/00* (2013.01); *C12N 2795/10121* (2013.01); *C12N 2795/10132* (2013.01)

(58) Field of Classification Search
None
See application file for complete search history.

(56) References Cited

U.S. PATENT DOCUMENTS

| | | | | |
|---|---|---|---|---|
| 8,066,990 | B2 * | 11/2011 | Yoon | C12N 9/503 424/94.6 |
| 8,071,352 | B2 * | 12/2011 | Yoon | A61K 35/76 435/235.1 |
| 9,211,309 | B2 * | 12/2015 | Yoon | A61K 35/76 |
| 9,402,873 | B2 * | 8/2016 | Yoon | A61K 38/162 |
| 9,433,653 | B2 * | 9/2016 | Yoon | C12N 7/00 |
| 9,540,616 | B2 * | 1/2017 | Yoon | A61K 35/76 |
| 9,950,018 | B2 | 4/2018 | Shin et al. | |
| 9,951,342 | B2 * | 4/2018 | Barrangou | C12N 15/746 |
| 10,028,984 | B2 * | 7/2018 | Yoon | A23K 20/195 |
| 2010/0015098 | A1 | 1/2010 | Bruessow et al. | |
| 2013/0323209 | A1 * | 12/2013 | Sung | A61K 35/76 424/93.6 |
| 2014/0017205 | A1 | 1/2014 | Shin et al. | |
| 2014/0356330 | A1 | 12/2014 | Kim et al. | |
| 2017/0037380 | A1 | 2/2017 | Shin et al. | |
| 2017/0037382 | A1 | 2/2017 | Shin et al. | |
| 2017/0333498 | A1 * | 11/2017 | Yoon | A61K 35/76 |
| 2017/0333499 | A1 * | 11/2017 | Yoon | A23L 2/38 |
| 2017/0340685 | A1 * | 11/2017 | Yoon | A61K 35/76 |
| 2017/0340686 | A1 * | 11/2017 | Yoon | A61K 35/76 |

(Continued)

FOREIGN PATENT DOCUMENTS

| | | |
|---|---|---|
| CN | 201580071157 | 12/2015 |
| CN | 201580071183 | 12/2015 |

(Continued)

OTHER PUBLICATIONS

Boyd et al, Trends in Microbiology, Nov. 2002, 10/11:521-529. published online: Sep. 26, 2002 (Year: 2002).*
Center for Health Protection, "Epidemiology, Prevention and Control of Shiga toxin-producing *Escherichia coli* infection", Nov. 2013, 19 pages (Year: 2013).*
Karmali, Journal Infectious Diseases, Feb. 1, 2004, 189:355-359, electronically published: Jan. 21, 2004 (Year: 2004).*
Werber et al, Clinical Infectious Diseases, Apr. 15, 2008, 46:1189-96. electronically published: Mar. 18, 2008 (Year: 2008).*
Zhu et al, Clinical and Vaccine Immunology, Feb. 2008, 15/2:359-366. published ahead of print on Nov. 14, 2007 (Year: 2008).*

(Continued)

*Primary Examiner* — Nita M. Minnifield
(74) *Attorney, Agent, or Firm* — Ballard Spahr LLP

(57) ABSTRACT

The present invention relates to a Myoviridae bacteriophage Esc-COP-1 that is isolated from the nature and can kill specifically Shigatoxin-producing type F18 *E. coli* strains, which has a genome represented by the nucleotide sequence of SEQ. ID. NO: 1 (Accession NO: KCTC 12662BP), and a method for preventing and treating the infections of Shigatoxin-producing type F18 *E. coli* using the composition comprising said bacteriophage as an active ingredient.

2 Claims, 1 Drawing Sheet

Specification includes a Sequence Listing.

(56) References Cited

U.S. PATENT DOCUMENTS

| | | | | |
|---|---|---|---|---|
| 2017/0348365 | A1* | 12/2017 | Yoon | A23L 2/38 |
| 2017/0368116 | A1 | 12/2017 | Regeimbal et al. | |
| 2017/0369852 | A1* | 12/2017 | Yoon | C12N 7/00 |
| 2018/0000125 | A1 | 1/2018 | Yoon et al. | |
| 2018/0119109 | A1* | 5/2018 | Yoon | C12N 7/00 |

FOREIGN PATENT DOCUMENTS

| | | | | |
|---|---|---|---|---|
| KR | 10-2011-0041670 A | | 4/2011 | |
| KR | 10-2012-0111535 A | | 10/2012 | |
| KR | 101260645 | | 5/2013 | |
| KR | 10-2014-0192983 | | 12/2014 | |
| KR | 10-2014-0192984 | | 12/2014 | |
| KR | 20140140698 | | 12/2014 | |
| WO | WO 2013/073843 | | 5/2013 | |
| WO | PCT/KR2015/014331 | | 12/2015 | |
| WO | PCT/KR2015/014332 | | 12/2015 | |
| WO | WO-2016108538 A1 | * | 7/2016 | A61K 35/76 |
| WO | WO-2016108541 A1 | * | 7/2016 | A61K 35/76 |
| WO | WO-2016108542 A1 | * | 7/2016 | A23L 2/38 |
| WO | WO-2017/111306 A1 | | 6/2017 | |
| WO | WO-2018101594 A1 | * | 6/2018 | |

OTHER PUBLICATIONS

Walker et al, Vaccine, 2105, 33:954-965 (Year: 2015).*

Gerdts et al, ILAR Journal, 56/1:53-62. (Year: 2015).*

Wenzel et al, Vaccine, 2017, 35:6798-6802, available online: Sep. 7, 2017 (Year: 2017).*

Hoa. N. X. et al. "Isolation and Characterization of Two T4-like Bacteriophages against Pathogenic *Escherichia coli* of Piglet", African Journal of Microbiology Research, (2014), 8 (41): 3604-3611.

Liao, W. C. et al., "T4-Like Genome Organization of the *Escherichia coli* 0157:H7 Lytic Phage AR1".Journal of Virology, (2011) 85(13): 6567-6578.

International Search Report and Written Opinion were dated Apr. 25, 2016 by the International Searching Authority for International Application No. PCT/KR2015/014331, which was filed on Dec. 28, 2015 and published as WO/2016/108541 on Jul. 7, 2016 (Applicant-Intron Biotechnology Inc.) (Original-9 pages// Translated—2 pages).

Bourgeois, A.L. et al., Status of Vaccine Research and Development for Enterotoxigenic *Escherichia coli*. Vaccine. 2016; 34:2880-6.

Clements et al., Infection Strategies of Eneteric Pathogenic *Escherichia coli*. Gut Microbes. 2012; 3(2):71-87.

Davis, Enteroirulent *E. coli* Infection Symptoms and Treatment. 2018. Retrieved from the Internet: https://www.medicinenet.com/enterovirulent_e_coli_eec/article.htm#enterovirulent_e_coli_eec_facts [retrieved on May 23, 2018] (18 pages).

Easwaran, M. et al., Functional Characterization of a Novel Lytic Phage EcSw Isolated from *Sus scrofa domesticus* and Its Potential for Phage Therapy. Mol Cell Probes. 2015; 29:151-7.

Giersing, B.K. et al., Report from the World Health Organizatio's Product Development for Vaccines Advisory Committee (PDVAC) Meeting, Geneva, Sep. 7-9, 2015. Vaccine. 2016; 34:2865-9.

Gohar, A. et al., Development of Safe, Effective and Immunogenic Vaccine Candidate for Diarrheagenic *Escherichia coli* Main Pathotypes in a Mouse Model. BCM Res Notes. 2016; 9:80 (18 pages).

Gohar, A.M.I.H. et al., Development of safe, Effective and Immungenic Vaccine Candidate for Diarrheagenic *Escherchia coli* Main Pathotypes in Mouse Model. 17th International Congress on Infectious Diseases/ Int J Infect Diseases. 2016; 45S:419 (Abstract only).

Intermountain Healthcare, Shigella/Enterinovasive *E. coli*: Information for Patients. 2018 (2 pages).

Mani, S. et al., Status of Vaccine Research and Development for *Shigella*. Vaccine. 2016; 34:2887-94.

Moriel, D.G. et al., A Novel Protective Vaccine Antigen from the Core *Escherichia coli* Genome. mSphere. 2016; 1(6):e00326016 (13 pages).

NCBI, GenBank Accession No. JN986846.1, Enterobacteria Phage vB_EcoM_ACG-C40, Complete Genome. 2012 (99 pages).

NCBI, GenBank Accession No. KM606996.1, Enterobacteria Phage RB6, Complete Genome. 2014 (98 pages).

O'Reilly et al., Centers for Disease Control and Prevention, Chapter 3: Infectious Diseases Related to Travel. May 31, 2017. https://www.cdc.gov/ (3 pages).

RightDiagnosis.com, Enteroinvasive *E. coli* Infection Symptoms, Diagnosis, Treatments and Causes. 2014 (4 pages).

Rojas-Lopez, M. et al., Intestinal Pathogenic *Escherichia coli*: Insights for Vaccine Development. Front Microbiol. 2018; 9:440 (17 pages).

Vieira, N. et al., High Prevalence of Enteroinvasive *Escherichia coli* Isolated in a Remote Region of Nothern Coastal Ecuador. Am J Trop Med Hyp. 2007; 76(3):528-33.

Walker, R.I., An Assessment of Enterotoxigenic *Escherichia coli* and Shigella Vaccine Candidates for Infants and Children. Vaccine. 2015; 33:954-65.

International Search Report and Written Opinion dated Apr. 25, 2016 by the International Searching Authority for Patent Application No. PCT/KR2015/014332, which was filed on Dec. 28, 2017 and published as WO 2016/108542 on Jul. 7, 2016 (Inventor—Yoon et al.; Applicant—Intron Biotechnology, Inc.) (Original—8 pages; Translation—7 pages).

Non-Final Office Action dated May 30, 2018 by the U.S. Patent and Trademark Office for U.S. Appl. No. 15/538,588, which was filed on Jun. 21, 2017 and published as US 2017/0333499 on Nov. 23, 2017 (Inventor—Yoon et al.; Applicant—Intron Biotechnology, Inc.) (12 pages).

U.S. Appl. No. 15/538,558 (2017/0333499), filed Jun. 21, 2017 (Nov. 23, 2017), Seong Jun Yoon (Intron Biotechnol., Inc.).

* cited by examiner

SEQUENCE LISTING

<160> NUMBER OF SEQ ID NOS: 1

<210> SEQ ID NO 1
<211> LENGTH: 169727
<212> TYPE: DNA
<213> ORGANISM: Bacteriophage Esc-COP-1

<400> SEQUENCE: 1
ctaaattagt taatagtata gcgccaggaa catataaaaa ggaaatacct gagcctcgtc 60
ttgttattcc aatttataat gctaacggaa aagccgagtc ttttcaagga cgtgcattaa 120
agaaagatgc tccccaaaaa tatatcacca tcaaagctta tcctgaggca acaaaaatct 180
atggagttga acgagtcaaa gatggtgatg tatatgttct agaaggacct atagattcac 240

-continued

```
tttttattga aaatggtata gctattacgg gtggtcaatt agacctagaa attgttccat    300
ttaaagatag acgtgtatgg gttttagata atgaacctcg tcatcctgac actattaaac    360
gaatgactaa attagttgat gcaggagaaa gggttatgtt ttgggacaaa tctccctgga    420
aatcaaaaga tgttaatgat atgattagaa aggaaggtgc aacccctgaa caaattatgg    480
aatatatgaa aaataatatt gctcaagggt tgatggctaa aatgcggcta tctaaatatg    540
ctaagattta aattaaccca actaaagcaa atgctaaatc tacgaatgta tcaagagtaa    600
ttactggaat attaacgcca tgagcaatag caattggcga taaaacaaaa ttccagagta    660
aaattcctac catagcagaa atagtaaaag ctatacgttt cttattacct tttatggcat    720
taacaagtgc cattaatttt tgtaccatgc gtcgtcctcc tttaaattaa atatttatcg    780
caaattttac aaaatttgtt tacttcctcg gttagttgtg gtattataaa ataaactgct    840
gaggataata taatgattaa taaaattgta catgaaatgg ctttaaacgg agattcatat    900
aaaatatctg ccgtagttga gaatttcata cttaataaag tgaaagagta tttcactgat    960
tgctcagtta gttatcaaga aaaaatggtt ttaactgacg atactgaaaa atcaaataat   1020
ttgttttgct cgaattttac aactaaaaag cgtactagaa gatttgatat tgtcatttct   1080
cgcaatggta aaaagcatat aattgaaatt aaacaccaag ttggtggagg tacagctatt   1140
gattctgttg gaatatattt agaagataaa gataaattaa aagaatacac aaaaactgaa   1200
acccctgtgt cattaatgat attagatttt tttgccatgc ggttattatc cacgcaataa   1260
atggacaaaa agagaatcat ttactgataa tccaactatt caggcaaggt ttaatgaata   1320
tgctaaatca caaaacgtgt tagtattact atcaaataca tatgatgaag aattatataa   1380
ttcgtttttt gctgcaataa atgagagaat ataatgttag gagctatcgc gtatacaggt   1440
aataaacagt cattattacc tgaacttaag cctcactttc caaaatatga cagattcgta   1500
gatttatttt gtggaggttt atcagtgtct ttgaatgtca atggtcctgt attggctaat   1560
gatattcaag aaccaattat tgaaatgtac aagcgtctta ttgatgtatc atgggatgac   1620
gttttaaaag taataaagca atacaaattg tcaaaaacat caaaagaaga gtttttgaaa   1680
ttgcgtgaag attataataa aactagagat cctcttttgc tttatgttct tcattttcat   1740
gggtttagta atatgattcg tataaatgac aaaggaaatt ttactactcc atttggaaaa   1800
agaactataa acaaaaatag tgaaaaacgt tttaatcact ttaaacaaaa ttgtgataaa   1860
ataatcttca gttcattgca ttttaaagat gtcaaaattt tagatggcga ttttgtatat   1920
gttgatcctc catacctcat aacagttgcc gattataata aattttggtc agaagacgaa   1980
gaaaaagacc ttttaaatct tttagactct ttaaatgaca gaggaataaa atttggattg   2040
tcgaatgttt tagagcacca cggaaaggaa aacgctcttc ttaaagaatg gtctaaaaaa   2100
tataatgtta agcatcttaa taaaaaatac gtctttaaca tacatcattc caaagaaaag   2160
aatggaactg atgaagtata tatttttaat taattgctta tatattcaaa tgatataatt   2220
atttaactta ttaatgaatt gaaaggaaaa ataatggcat attttaacga atgttcacaa   2280
ctgattgaag gcgctgataa agctcaaaat gaatactggg atattctcgg tgatgaaaaa   2340
gacccgctgc aggttatgct tgatatgcag aaatctctgc aagttcgttt agctaaagat   2400
aagcctgaat ataaccgtca tcctgatgat ttggctactg caggtgaagt tgttgattgg   2460
ttgcgtaatc agaaagatta tattgatgat gaattccgcg aacttctgac ttctcttggt   2520
ggtatgagca atggtgaaaa agatgcatct gctgtatgga agccttggaa gtcgcagcat   2580
```

-continued

```
ggtgaacgtc gtgaaactct gattactgat ttgtctccac aagaccagtt ggaaattaaa   2640
ttcgaaatga ttgatattct tcatttcgtt ctgaacatgt tccaaggtct tggtcttacg   2700
gctgaagaaa tctttaaact ttattatctg aaaaatgctg aaaactttgc tcgtcaagac   2760
cgaggttatt aatagctcgt ttatttaaac gacgacttaa aagccgtgag aattattata   2820
aataatcatg taatttaaat aaaaggagaa ttacatggct agtactcgcg gttatgttaa   2880
tatcaaaacg tttgagcaga aattagatgg aaataagaaa attgaaggaa aggaaatttc   2940
tgtagctttc cctctttatt ctgacgttca caaaatttct ggcgctcatt atcagacatt   3000
cccttcagaa aaagcagcat atactactgt atatgaagaa aatcaacgcg ctgcgtggat   3060
tgctgcaaac gaagatttgt ggaaagtaac tggtgaataa attcagggac tccttcagga   3120
gtcctttttt cattttaccg gtttactttc cacaatgagt atggtataat agaattatct   3180
tatagaggag agcactatgt taaatcgttg gattaaacca aatgaagacc tccagaaggt   3240
tcttgataaa gctatctctg ataaatgggg tatgaaaagc tgggattgtg atatcgtcac   3300
gcattcattc atgatgcatg cagatggttc agtcgagttc aatgctgaaa tgcgatacac   3360
tgactggggt ggatttcaaa gagtcgaatt tcaaagaggc tttttgtaat gtttatcttt   3420
aattggttta aaagtttctt tacggatttt ttctctacga ctccgggaga aggtgtagtt   3480
cctattacaa atgactacct tcctttaact gtagttgaat atgtttatat gggagatgga   3540
acagtagaag cagttactat gacttatgaa gaagcccagg aatattataa aaatccttgg   3600
cgttggtcaa cacctacatc atctaatacg cagaatacac agtctagttc tgattcatat   3660
gacactaatg ttcctgttca tgtatggacg ggagattcat gtggaagttc ttgtgattct   3720
agttgttcat ctacatcttg tgattgagga aaattatgga agcgattttg tttgaaatgt   3780
atattagcag taatagtttg tcgtttgcta aagacgttcc aattaccgta gcagtaatga   3840
ttgataaggg ttattgtgac ccaatgtatc tcgtagaaaa tttcgtttca atgccagttc   3900
cagaagatgc tgaaataaaa cttaaaaaga ttggtattat tgaaactgta ccaaatattc   3960
catttagagc aattgaagca tttactaaat ccgaatacat caatgttagc gcagaacaat   4020
ataatgataa ccctttatct ttttattcgt acgattcagt atatgactgg aaaatagata   4080
aaggaaataa atttataatt gcgagtgaag atgctttatc atactttatt tcttctgtat   4140
ggaatagttt acatccaaat ttgctaaaaa ttcatgaatt tgatgatgct cctactattg   4200
ttttaggtaa aacaaatgaa aattctgaag aagatgcttg aatggttcag tagaccaagc   4260
tcaatgtata ttgacgatgg ttgggttgaa caagcaaata aagaaatgca gaacgaatcg   4320
gaagaatgga tgaaatcaat gattagtgct gagaaagaaa agaaattaga acgctcagca   4380
cttaaattaa tgagagacat ctatggggat aaatcgtgaa caaagatatg acattagaag   4440
aggctaaagc taaagcaaac gaagcactgg atttgcttct taaaatcggt agtaaaatga   4500
tggaagaaaa tgagaaatac attcaggaaa acaaaattcc tgacggtcca ttagtaggca   4560
aaaggaaatc acatgattga agtagcaaaa cgttattcaa tagaatttat gtctaaagaa   4620
ggtaaatcag taaatacact taataaaaat tgctcattaa ttattccttt agcagaaaat   4680
ccggatcatt taattaaaga tataaaagaa agaaaatatc cagaaaatgt tattctagtt   4740
ataaagcata ctgaagatat tttgcataat acagattcac cgttttcttc ttctgaagct   4800
ttaactatta aaggctataa aagagctcat gaatatggtc tttttgacct gtttgaagac   4860
gataaagtta aattagctag tcaaccttct aaaagtaaaa cattcattat tgaagatatt   4920
aaagatataa atgcatttat taagatggtc tgggctcatt ttgatgttgg actacgctgg   4980
```

```
agaatgtccg aagaagaaag aaagattatt gaagctaatc gtcattttgg tttttatcgc   5040
taggaattaa tatggattta tttgagatgt tagaagataa tcattctacg aatatccaga   5100
atgattctag tgattataag aaagagtacc gtatagtatt acagaattat ggaattgaag   5160
ccccagatgc tcttctagaa gaactagctt cataccatct tgaccctccg ccctgggctc   5220
cctgggcaaa ataattcaaa aagttgttta ctttccttcc taacaatgat atgatagctt   5280
ctgaagtata tggaggctat catgattatt aatctcgcag atgttgaaca gttatctata   5340
aaagctgaaa gtgtcgattt tcaatatgat atgtataaaa aggtctgtga aaaatttact   5400
gactttgaac agtcagttct ttggcaatgt atggaagcca aaaagaatga agctcttcat   5460
cagcagttga ataaaatcgt taaaaagcat ttaactaaat cgccttatca gctatatcgt   5520
ggtatatcaa aatcgacaaa agaactcatt aaagatttac aagtcggaga agtgttttca   5580
acgaacagag tagattcatt tactactagt ttgcatacag catgcggttt ttcttatgtt   5640
gaatattcca ctgaaataat atttcgctta aaaactgata aagcttttaa ttattctgac   5700
catatcagcg atattatact ttcttctcct aatactgagt ttaagtatac atatgaagat   5760
actgatggat tagattcaga acgtactgat aacttaatga tgattgtacg tgaacaagaa   5820
tggatgattc caattggaaa gtataaaata acttctattt caaaagaaaa attacacgat   5880
tcatttggaa catttaaagt gtatgatatt gaggtagttg aatgaaatat tcagcaatgc   5940
aattaaaaga ttttaaaata aaatcaatgg atgcatcggt gcgtgcttct attcgcgaag   6000
aattactttc tgaaggattt aatttatccg aaattgaact tttaattcat tgtattacta   6060
ataagccaga cgatcattct tggttaaatg aaataatcaa atctcgtttg gttccaaacg   6120
ataaacctct ttggagaggt gttccagttg agactaagca ggtattaaat caaggaattg   6180
atattattac atttgataaa gtagtatcag cttcatatga taaaaatata gctctacatt   6240
ttgcttctgg attagaatac aacacacaag ttatttttga attcaaagct cctatggtgt   6300
ttaatttcca ggagtatgct ataaaagctc tacgttgtaa agaatatagt ccgagtttta   6360
aatttccgga tagccatcgc tatcgtaata tggaattagt ttcagatgaa caagaagtaa   6420
tgataccagc tggaagtgta tttagaattg cggatagata cgagtataaa aagtattcaa   6480
catacactat ctatactctt gactttgaag gatttaatct ataatggaag gacttagatt   6540
cattatacca tgaaagtttt aaagcatttt tcataaagtt gtttacaaac tgaagtaaaa   6600
atgttatagt ataagtagtt aaccgtccgt gagaaaaata tgaaactgtc taaaaatcaa   6660
attcgtaaaa ttacacgtcg tctagagcat acccaggcat ctgctaaaag acgttctaaa   6720
gattttaact tagacttcaa ttacattaag aacattttag atcagaaagt ttgcgcttac   6780
tcgggagaac cttttgataa tcgtattgaa ggagagaaat tatcattaga acgttttgat   6840
aataacgttg gatacattaa agggaatgtt attgcagtaa agaaaaagta taatacattt   6900
cgttctgatt atactttaga agagttgatt gaaaagcgtg atttatttgc tttgcgaatt   6960
ggtcgttcat ctgcgaaaaa agttcataaa ctaaatttag atgaaaagaa atgggctaaa   7020
atcaaaaaga cttataatca aattaaagct atacagaaaa aacgtgaaaa tcgaattgaa   7080
cacatttctc agctttctaa atcaaaacaa acctctgata ttaagctaac gattgtagca   7140
ctcaaagctc gtattgatgg ttctcgtata gcagaaggca ctgaagttgt taaattgaac   7200
gttcttctta aaggctctga ttggaaaact gtgaaaaagt tgtcagaagc agaaatgcaa   7260
tatgatatgt gtgataaaat tattcaaggt gtagagcggt atcaaaactt gtcttttatt   7320
```

```
gataaactta aactgaaaag aggataccg ctaaattgtt caatttttaa acttatccga   7380
ggataatatg ttttatgtat atgcgatagt gtatagagac aaagatggat ttgcagtgcc   7440
tgttccgctt gatgaacatc gccctgctgt attttttgaa agggagattg ctgataaagt   7500
atttaccact cttaaagagc agtatcgact agctttaggt atgggaattc cgagattagt   7560
tgagactcca cgcaagtttt ggtttaataa aatagaagtt aaacatgtta agcctgatat   7620
agacacacaa agattatatc ggcgaatttt agatactggg cgtattgtta gtataccaat   7680
tgcagggaat ttacgatgac atttgatgat ttgaccgaag gccagaaaaa tgcctttaac   7740
atcgttatga gggctattaa agaaaagaaa catcatgtaa ctattaatgg acctgctggt   7800
actggtaaga ctactcttac taagttcatc attgaagcct taatatctac gggcgaaact   7860
ggcattattt tagcagctcc tacacatgcg gctaaaaaga ttctttcaaa actatcaggg   7920
aaagaagcga gtactattca cagtattctt aaaattaacc cagtaacata tgaagaaaac   7980
gttcttttttg aacaaaaaga agtaccagat ttagctaaat gtagagtatt aatctgcgac   8040
gaagtgtcaa tgtatgatag aaagctattt aaaattctgc tttcaactat tccaccttgg   8100
tgtactataa ttggaatagg cgataataag caaattagac ctgttgaccc aggagaaaac   8160
accgcttata tcagtccgtt ctttacacat aaagattttt atcagtgtga actcactgaa   8220
gttaaacgca gtaatgctcc tattattgat gtagctactg atgttcgcaa cggtaagtgg   8280
atttatgata aagttgttga cggcgcatgga gtacgtggat ttactggtga taccgcttta   8340
cgtgatttta tggtaaatta tttttcaatc gtaaaatcac tagacgattt gtttgaaaat   8400
cgcgtaatgg catttacgaa taaatctgtt gataagttaa atagcattat tcgcaaaaag   8460
atttttgaaa ctgataaaga ttttatcgtt ggtgaaatta ttgtaatgca ggaaccatta   8520
attaaaacat ataaaattga tggaaagcct gtgtcagaaa ttatttttaa taacggacaa   8580
ttagttcgta ttatagaagc agagtataca tcaacgtttg ttaaagctcg tggtgtttct   8640
ggagaatatc taattcgtca ttgggattta acagtagaaa cttacggcga tgatgaatat   8700
tatcgcgaaa agattaaaat aatttcatct gatgaagagc tgtataagtt taacttattt   8760
ttaggtaaaa cggcagaaac ttataaaaat tggaataaag gtggaaaagc tccgtggagt   8820
gatttttggg atgctaaatc acagtttagt aaagtgaaag cacttcctgc atcaacattc   8880
cataaagctc agggcatgtc tgtagaccgt gctttcatct atacgccttg tattcattat   8940
gcagatgctg aattggctca gcagcttctt tatgttggtg tcactcgtgg tcgttatgat   9000
gtgttttatg tatgattaaa tttgaggaag ctattcgtgg aaataactaa agaccagttt   9060
tatctacttc aagataaagt gagcgaaata tatgaaatag cttatagtaa aaatcgcaaa   9120
aacgtgaaaa ttgaatcagg caagttaatg cttcaattgg aagaaattga acgagatttg   9180
attgcgttag aattcttttg tggtgaagtg aaaactgtta caatcagtga ttatatttta   9240
ggcgaaatta gccatcttta taaggcggtt attaatgatt gaattaagtt tacatcagtt   9300
taaatctctt atgacaaatg ttaaagctgt cattgaggaa aatccaggac ctgataatgt   9360
tactattcgc gaaaaagctt caaagatagt atacagtctt gaagagatac aaaaagatat   9420
tgaatctatg gcaaaattta ttgatgagcc cattaataaa gtttatatcc aagattatac   9480
tgtaggtcaa attcgcgatt tagcaaggaa aatttaatgt ttgattttat tatagatttt   9540
gaaacaatgg gaagcggtga aaaagcagct gttattgatt tggctgttat tgcctttgac   9600
cctaacccag aagtggttga atcatttgat gaattagttt cgcgcggcat taaaatcaaa   9660
tttgatttaa aaagtcaaaa aggacatcgt ctttttacta aaagcactat cgaatggtgg   9720
```

```
aaaaatcagt ctcctgaagc tcgaaaaaat attgcgccat cagatgaaga tgtaagcact   9780
atcgatggta ttgtaaaatt taatgattac atcaatgcgc ataatatcga tccttggaaa   9840
tctcagggtt ggtgccgtgg aatgtcgttt gattttccaa ttttagtcga tctcattcgc   9900
gatattcaac gtcttaatgg cgtttctgag aatgaacttg acacatttaa gttagaacca   9960
tgtaaattct ggaatcagcg tgatattcgt accagaattg aagcacttct ccttgttcgt  10020
gatatgacca cgtgtcctct tccaaaagga actttaaatg gattcgttgc acatgattct  10080
attcatgact gtgcgaaaga catcctgatg atgaagtatg ctttgcgata tgctatgggt  10140
cttgaagatg ctccgtcaga agaagagtgc gatcctctat ctcttccaat aaaacgataa  10200
aaagtagcta ttttgaatta atagtttaca aactcttggg accagagtat aatggtcccg  10260
tggagcataa aatcttttta acaagtgaga gataactatg attattaata ttggtgaaat  10320
tgctcgtgta tctgataaat cccgttctaa agcagcagga aaattggttg aaattgtaag  10380
cattcagctt aaacatggtg ttaaagatga agattctgaa gtaaaagtgc gtatcattcc  10440
taaagatgga aagtctaaac cccagtttgg atatgttcgc gcgaaatttc ttgagtctgc  10500
gtttttgaaa gctgttcctg ctaaaggaat tgaaacgatt gatacttcgc acgtaggtgt  10560
agactttaag tggaaactcg gtcaagctat taagttcgtt gctccttatg aattcgaatt  10620
tactgaagat gaggaggggg ttgttcaaaa acaccgtact cgcgctatgt gtgcatacat  10680
taccgatcag tgggtagaag atggcgttaa gttgtacaac gcggtatttt taggaacata  10740
caaagtcatt cctgaaagct ggattaaaca ctatagcaaa gcccgctatg cataaagttt  10800
aaaatttttt cataaaacta tatacatcag tagttgatta tggtactata tcaatatcaa  10860
ctactgatac agaaaacaac ttggagaata aaatggaaaa cttaattatc atcgaacaat  10920
ctttcaacga ttatggtatg gcttacggtt atcgtgcgat aatggaagat tctcgtggat  10980
gtgttatcga tattgctgaa tgtaaagatt tactgcagct tttgaagatt gttcgcaaaa  11040
attgggattg tgaaaacatt aaagctcgtg ttgtaacgga agaagaaact gtttttcatg  11100
atgtaaaatt cgccaaaggt gttgctactc ttctgaaacg catcgctcca ctgttcaatt  11160
aatgaggaaa ttgtaatgaa acgtaaaatt gttcagaatt gcactaatga tgaatttgaa  11220
gatgtattat tcgatccaga tttggtagta gttcaaaagg aacacactgc taagtttact  11280
cacttgactt cggtttatgt gtatgaaaag gttggtgata aacaaccaat ttacggtgta  11340
ttccgtgaaa tcactgaaga cggtacaact tactggaagg aaatttatta atggctatta  11400
gatttgaagt taataaatgg tatcaattta aaaataaaca agctcaagaa aattttatta  11460
aagaccatat taataacgga atctacgcgc gccgtttagg tatgtatcct tttaaaattt  11520
tagatgtgga cgctcttggg cgtcctatta aaattttgtc atctactgga aatttagtac  11580
tatctcctga taaagatgtt ttggatgaag actttatttg gctttcaaaa agtgaagctg  11640
ggttctttga tgaagttgaa aatccatacc aggcagctga agaacaagag caggaagagc  11700
aagaacaaat agaagatttc acagaatttc ctgtcatgaa agttactatt gaaaataatg  11760
aacatgcatg gtccttgtat cagatgttga aagcacactt taaggaataa ttatgccaat  11820
gtatgattat aaatgccaat ccaaagactg tgcaaaagaa tacgaaaaaa tcaagaaaat  11880
ttctgaaagg gatactgatg tatgtcctga ttgtcatcgg attgctattc ggttagtttc  11940
cgctcctaag catgtgaatg gtggatttta cgacttactt aaagggtgat tatgtttaaa  12000
atcggtaaga aatatcgtgt tcgcgaaggt gaagaaaaga aatatctact ttcttctatt  12060
```

```
tataggaatg gttctattaa tgccgtaata tctacaagcg aatttatcgt tgaagatatg  12120
aaaggtaata atgttacaat gattagtaca gcatctggaa atgatggaaa aattcttcac  12180
agttttcaga gtaatgttct aatttatgat gaagaatttg acttcttcga agaagttccc  12240
gaaggttttg attttgaatg tactatcact atgaaatctg gtgaccctct ttcttttaca  12300
gttaaagatg aaagaagtcg cttgagaatt attagtcttc ttcaagccat taaatttgag  12360
tgaaaattat gaaatatatt aatcgttcta tcgcggcatt agtattagca gtgtctttag  12420
caggatgtac tgatgctgat aatgcaacca aagttttgtc ttcaagtggg tttactaata  12480
ttgaaatcac tggatacaat tggttcggtt gctctgaaaa tgatttccaa catactggat  12540
ttcgtgctat tggacctacc gggcagaaag tagaaggaac cgtatgttct ggtctattct  12600
tcaaggattc gactatccgt tttaaataaa aggccttcgg gcctttagct ttatgattac  12660
cggagtataa tattcccgaa accaaacgag gataagtgat gattaagaat gaaattaaaa  12720
ttctgagcga tattgaacat atcaaaaagc gtagcggcat gtatattggt tcttctgcta  12780
atgaaatgca tgagcgcttt ctgtttggta aatgggaaag tgttcagtat gtacctggtc  12840
ttgttaagct tattgatgaa attatcgata actcagtaga tgaaggtatt cgtactaagt  12900
ttaaattcgc gaataaaatt aatgttacta ttaaaaacaa tcaagtaaca gttgaagata  12960
acggtcgtgg tattccacag gcaatggtta aaacacctac tggtgaagaa attcctggtc  13020
ctgttgctgc ctggactatt ccaaaagcag gtggtaactt cggtgatgat aaagaacgcg  13080
tcactggcgg tatgaacggt gttggttcta gtttaactaa tatttttttct gtgatgtttg  13140
tcggtgaaac tggcgatggt caaaataata ttgtagttcg ttgttcaaat ggcatggaaa  13200
ataaatcatg ggaagatatt cctggaaaat ggaaaggaac tcgcgttact ttcattcctg  13260
attttatgtc atttgaaact aatgatctat ctcaagttta tcttgacatt acattagatc  13320
gtctccagac acttgcagta gtttatcctg atattcaatt tacctttaat ggtaaaaagg  13380
ttcagggtaa ttttaagaaa tatgcacgcc aatatgatga gcatgctatt gttcaagaac  13440
aagaaaattg ttctattgcg gttggtcgtt caccggatgg ttttcgtcaa ttaacatacg  13500
tcaataacat tcatactaag aatggtggcc atcatattga ctgcgttatg gatgatattt  13560
gtgaagacct tattccacaa atcaaacgta agttcaaaat tgatgtaact aaagcacgtg  13620
ttaaagaatg tttgactatc gttatgtttg ttcgtgatat gaaaaacatg cgatttgatt  13680
ctcagactaa agagcgtttg acttctccat ttggtgaaat tcgtagtcat attcagcttg  13740
atgctaaaaa gatttcacgc gctattttaa acaatgaaga aattttaatg ccaattattg  13800
aagctgcctt ggctcgtaaa ttggcggcag aaaaggcagc agaaactaaa gcagctaaaa  13860
aggcttctaa agctaaggtt cataaacata ttaaagcgaa tctttgcggt aaagatgctg  13920
atactactct tttcttgact gagggtgatt ctgctatcgg atatcttatt gatgttcgtg  13980
ataaagaact tcatggtggt tatccattgc gtggtaaagt tcttaacagt tggggtatgt  14040
cttatgctga tatgcttaaa aacaaagaac tgtttgatat ttgcgcaatc actggattag  14100
ttcttggtga aaaagctgaa aacttgaatt atcataatat tgctattatg actgatgctg  14160
accacgatgg tctaggaagc atttatcctt ctctgctcgg attttttagt aattggccag  14220
aactgtttga acaaggaaga attcgcttcg tcaaaactcc tgtaatcatc gctcaggtcg  14280
gtaaaaaaca agaatggttt tatacagtcg ctgaatatga gagtgccaaa gatgctctac  14340
ctaaacatag catccgttat attaagggac ttggctcttt ggaaaaatct gaatatcgtg  14400
agatgattca aaacccagta tatgatgttg ttaaacttcc tgagaattgg aaagagcttt  14460
```

```
ttgaaatgct catgggagat aatgctgacc ttcgtaaaga atggatgagc caatagttta  14520
ctttaccaca aggatgtggt ataattaatt gggcaaatga ggatattgaa atgaaatcat  14580
ataaagtaaa tttagaactt tttgataaag cagttcatcg agaatataga atcattcaac  14640
gctttttcga tatgggagaa gccgaagagt ttaaaaaccg ctttaaggat attagagata  14700
aaattcaatc cgacaccgca actaaagatg aactactaga agttgccgaa gttattaaac  14760
gcaatatgaa ttaatgagga aattatgatt atcaccactg aaaaagaaac aattcttggt  14820
aatggttcta aatcaaaagc atttagcatc acagcatctc ctaaagtatt taaaattcta  14880
tcatctgatt tgtatacaaa caagattcgt gcagtagtcc gtgaattgat taccaatatg  14940
attgatgccc atgctcttaa tggaaatcct gaaaaattta tcattcaagt tccaggacga  15000
ttagatccgc gatttgtttg tcgagatttt ggtccaggta tgagcgattt tgatattcaa  15060
ggtgatgata attctcctgg gttgtataat tcatacttta gttcatctaa ggctgaatct  15120
aacgatttca ttggcggatt tggtttaggt tctaaatctc cgtttagtta tactgataca  15180
tttagtatta cttcatatca taaaggtgaa attcgtggtt atgtagctta tatggatggc  15240
gatggtccgc agattaaacc tacattcgta aaagaaatgg gtccagatga taaaactggt  15300
attgaaatcg tagttccagt tgaagaaaaa gactttagaa actttgctta tgaagtttct  15360
tatatcatgc gaccattcaa agatttggct atcattaatg gtcttgaccg cgaaattgat  15420
tattttccgg attttgatga ttattacggc gtaaatccag aaagatactg gccagatcgt  15480
ggtggattat atgccatcta tggtggtatt gtttatccta tcgatggtgt tattagagac  15540
cgtaactggt taagcatccg caatgaagtg aattacatta agtttccaat gggttcactt  15600
gatattgctc catcacgcga agctctttca ctagatgatc gtactcgtaa aaatattatt  15660
gagcgtgtta aagagcttag tgagaaagca ttcaatgaag atgtaaaacg atttaaagaa  15720
tctacatctc ctcgtcatac ataccgtgaa ttgatgaaga tgggatattc tgctcgagat  15780
tatatgatta gtaattcagt caaatttacg actaaaaatc tgtcatataa gaagatgcaa  15840
agcatgtttg aacctgacag taagttatgc aatgcaggag ttgtgtatga agtaaatctt  15900
gaccctcggc tgaaacgtat taagcaaagc catgaaactt cagccgttgc atcaagttat  15960
cgtttgtttg gtattaatac aacaaaaatc aatatcgtta ttgataatat taaaaatcgt  16020
gttaatattg tccgtggatt agcgcatgcg ttagatgata gtgaatttaa taacactttg  16080
aatattcatc ataatgagcg tcttctgttt attaatcctg aagtagaatc gcagattgat  16140
ttactccctg atattatggc aatgtttgaa agtgatgaag ttaacattca ttatttgtca  16200
gaaattgaag ctttagttaa aagttatatt ccgaaggcag ttaaaagtaa agctcctcgt  16260
cctaaagctg ctactgcgtt taagtttgaa attaaagacg gacgctggga aaaagaggaa  16320
ctgtttacac tcacatcaga agcagatgaa attactggtt atgtagcata catgcatcgt  16380
tctgatattt tttctatgga tggtactaca tcgctttgtc atccatctac gagtattttg  16440
actcgtatag ctaatcttat tggcattaat gaattttatg ttattcgtcc actttttgcag  16500
aaaaaggtaa aagaacttgg tcagtgccaa tgtatttttg aaactctgcg tgatttatat  16560
gtagatgctt ttgatgctgt agattatgat aagtatgtag gttattcaag ttcagctaaa  16620
cgatatattg ataaaattat taagtatcct gaactcgatt ttatgatgaa gtacttcagt  16680
gtagatgaag tttctgaaga atatactcgc cttggtaata tggttagttc attgcagggt  16740
atatatttca acggtggaaa aggtaccatc ggtcatgaca tctggacagt aactaatctt  16800
```

-continued

```
tttgatgtat tatcaaataa tgcttcaaaa aatagtgata aaatggttgc tgagtttacc  16860
aagaaattcc gtattgtttc cgacttcatc ggttatcgca gctctttgag tgatgatgaa  16920
gtttcccaaa tcgctaaaac tatgaaggcc cttgcggcct aataaggaaa attatgtaca  16980
atattaaatg cctgaccaaa aacgaacaag ctgaaattgt caaactgtat tcaagcggta  17040
attataccca gcaggaattg gctgattggc aaggtgtatc agtggacaca atccgtcgtg  17100
ttttgaaaaa tgctgaagaa gctgagcgct ctaaagttac cattagcggt gatattacag  17160
ttaaagttaa tagcaataca gctattgctc cagttgctaa atctgacatt atttggaatg  17220
catctaaaaa attcatttca attactgttg atggtgtaac ttataacgca actcctaata  17280
ctcattcaaa cttccaggaa attcttaatc tgcttgttgc agataaattg gaagaagcgg  17340
cacaaaaaat taatgttcgt cgcgctgttg aaaaatatat ttccggtgat gttcgaattg  17400
aaggtggaag cttgttctat caaaatattg aattgcggtc tggtttagtt gatcgtattc  17460
tcgattcgat ggaaaaaggc gaaaactttg aattttattt tccgttcttg gaaaatctgt  17520
tggaaaaccc gagccaaaaa gcggtatctc gactctttga tttcttggta gcaaacgata  17580
ttgaaattac agaagatggc tacttttatg cttggaaagt agttcgcagc aattactttg  17640
actgccattc aaatactttt gataacagtc ctggtaaagt agttaaaatg ccacgtactc  17700
gtgtgaacga cgatgataca caaacttgtt ctcgtggtct gcatgtatgt tctaaatctt  17760
atattcgtca ctttggcagt tcaaccagcc gagttgtaaa agttaaagta catcctcgcg  17820
atgtagtatc aattccgatt gattacaacg atgctaaaat gcgtacctgc caatacgaag  17880
tagttgaaga cgttactgaa caatttaaat aagggcttcg gcccttaact aaggaaaatt  17940
atgttaggtt atcaagcacg agtaaaagaa gaatacgatc aattaatgct caaaattaat  18000
gcactgagca aatttttaga aagcacaaag tttctatcag ttaatgaagt tgagcaagaa  18060
ttactgcttt cacagttcat ctcaatgaaa tcttacgcag actgtttaga aaaaagaatt  18120
gcacaattca aataaataag ggcttcggc cctttttgttt taaggaaaaa ttatgattta  18180
ttgtatgaat atcggtgatt ccgacataaa agagattaaa ctgcacggaa atcatcacgc  18240
taatattgtg tactgcaata aatttgagtt tggtcacgaa aaacttgggt ttctttactg  18300
caatgatgtt atagtcatgg ataaaaagga actcgatgaa cttgaccatg agtctttaga  18360
tgaaaatgac cgaatttatt acggcactct taaagtatat aacgcttatc tcagcggtaa  18420
aaaggaaagt ctaaatgcag aaaacgaatc cgggtttaca gagactattt cagattccga  18480
catttaccct atcgaacagt gacttgacta gcgaaatgaa ggtcaaaatt gctgatacag  18540
caagatactc tttaaaacaa aatccaaatc aggataaagc agaagttatt gaaagatgtc  18600
gtatcgcggt gtacgcagaa ttttttgtag cagattggct aagtgggtat gttaacaaag  18660
gccaagaaga tgttaatgac ccgtatacat atgcatggga tgtattggcg catccaagat  18720
actgcgggct tcgtgtagaa gttaagacac atcaaactga ctcacgttgg atttctgtaa  18780
caacaggatg cagcggagag tatccatatg gttctggaat aaatctaggg cccattctga  18840
atcatcaggt cgctgactgt ataattatat tcaacactaa agaaattcac ccaggtgtca  18900
tccagtacac tccgaagttc atcggtgata gagaagacct tcgtaaggtt gtaagaaaaa  18960
gcaactacaa cggatggtat ctttccattt aaaaaaaatt ttcacaaaac ggtttacata  19020
ccacaaggac tgtggtacta tacaactatc aactgatacg gatttggaga ataaaatgtt  19080
tactacagct gaattaaaac gagcaaaagc taagaaaggg caaggaaaat ataaagctga  19140
attagttaaa gaacttcagt ttgctgaggc tgaattgaat tcaatgatta ttcaaaatgc  19200
```

```
tccagaaact gaaattgctc ttaaacgtat tgcgaataag tgtcttcatg atacaatcgt  19260
cgatctttta gcggattatt gagtaaaatg aaaatcgttg agattgaact atgagttcat  19320
tatggtggtg ttttgtttgg ttagttagta ttccattaat ttgtttaaca tttacttttg  19380
taatgaggtt attatgaaaa ttttgaattc tgtgcttatt gcttgtgcgt ggtgggttgc  19440
acaagtttca gcggtagtag ttggtattca catttattac gaatattttt aaaaaagttg  19500
tttacaagac tgttcctctg tggtattatt accctatcaa ctacggagga acagaaaatg  19560
aaaaagattg ttaaagctat atggaatgta gttataatac tagtagtttt gagtatattc  19620
ccaatcgttt taatgattga tgtattaaac gcttactttg gatttatgtg aggaaaatat  19680
gaagcgtaaa cgcagtgctt ttacatttat tgaatggttt ttcgataata tttttccggc  19740
tttattcatt ttcatgctga tttttgcctt aggttcagtt gtagttggaa tctatttgat  19800
ggcggtagtc ggaatggata ttcatcaaaa tggtttaaaa tccgtagttg aaacaatttg  19860
gaatggtgta aaatgatgaa tttactaaac atttggtttt atattcttat gttttacatt  19920
ggcgcaaatt tcccatattg gatgggatgg tcaacaactg catttggatt ttatactcct  19980
tgaggtgaat tatgaaaagt tttaaagatg taaaagttgg tgaaattttc tgtttagata  20040
atggtgatca gttaattcgt atttcacctc ttaagagcac tagcgagaaa ccgacagtta  20100
atgctacttt agcaaataat agtaatgaac gtttctgtat tgaaaatgat actgaaactt  20160
acaccgtaga agaattctgg gaattgagcg tcgactgcga cgattaattt aatggccgcg  20220
tgtattcatg cggccttgga gtagaaaata attagaggaa attaaaatga aatacatgac  20280
tgttactgat ctgaacaacg caggcgctac tgttattggt acaatcaagg gtggtgagtg  20340
gtttttggga actccgcata aagatatttt atctaaacct ggattttact ttttagtaaa  20400
tgaattcgat ggttcatgcg tatccgcacg attttatgtg ggtaatcagc gttctaagca  20460
aggattcagc gcagttctaa gtcatattcg tcaacgccgg tctcagcttg cgcgtactat  20520
tgcaaataac aatatggcat acactgtatt ttatcttcct gcttctaaga tgaaacctct  20580
gacgacggga tttggtaaag gtcagttagc tttggcgttt actcgtaatc atcattctga  20640
gtatcaaaca cttgaagaaa tgaaccgtat gttggctgat aactttaaat ttgttttgca  20700
ggcatattaa tgagtaattt ccataacgaa catgtgatgc agttttatcg taacaatctt  20760
aaaactaaag gcgtcttcgg acgccagtga ggaaaatatg aatatcgcaa aattattagg  20820
agttatttca tttatttgtt ggatagtagc atgtgtttta actatctgta ttgatgccag  20880
cagtgtgttt tcacaagctt tagcccaggg tatgtgtgca tatttaacat ttgtgttgtt  20940
atctactaat gattaagaaa atcttgggct attcactagc ccttgctact ttattggtag  21000
cactatatta tggagtaatg ttcggattaa ttcaagtcgt gcttttcatt tctgatgtta  21060
ttatggcact acattcacta gtatggtaaa tttatgcaac tgaataatcg cgatttaaaa  21120
agtatcattg ataatgaagc attggcttat gctatgtaca cggttgaaaa tcgtgctatc  21180
ccaaatatga ttgacggatt taagccagtc caacgatttg ttattgctcg agctcttgat  21240
ttggcacgag gaaataaaga taagtttcac aaacttgctt ctattgcagg tggtgtagct  21300
gaccttggat atcatcatgg tgaaaactct gcacaagatg caggtgcttt gatggctaac  21360
acttggaata ataattttcc tctgttagat ggtcaaggaa actttggttc tcgtaccgtc  21420
caaaaagcag cagcaagtcg ttatattttt gctcgtgtaa gtaaaaattt ctataacgta  21480
tataaagata ctgaatatgc tccggtacat caagataaag aacacattcc gcctgctttc  21540
```

```
tatttgccta ttattcctac tgttcttctt aatggcgttt ccggtattgc aactggttat  21600
gcaacttaca ttcttcctca tagcgtttct tctgttaaga aagctgtatt acaagctctt  21660
caaggaaaga aagtaactaa accgaaggta gaattcccag aatttcgtgg tgaagtcgtt  21720
gaaattgatg ggcaatatga aattcgtgga acatataagt ttacttcacg aactcaaatg  21780
catatcactg agattccgta taagtatgat cgtgaaactt atgtgagtaa aatcttagac  21840
ccgcttgaag ataaaggctt cattacgtgg gatgatgctt gtggtgagca tggctttggc  21900
tttaaagtta aattccgtaa agaatacgct ttgagcgata acgaagaaga acgtcacgcg  21960
aaaattatga aagacttcgg gttgattgag cgtcgttccc agaatattac tgttattaat  22020
gagaaaggaa agctgcaagt ttacgataac gtagttgatt taatcaaaga cttcgttgat  22080
gttcgtaaaa cttatgtcca aaaacgaatt aataacaaaa tcaaagaaac tgaatcagca  22140
tttcgtttag cctttgccaa ggcacatttc attaagaaag taatttcagg tgaaattgtt  22200
gtacaaggta aaactcgtaa agaactgacc gaagaacttt ctaaaattga tatgtattct  22260
tcttatgttg ataaactagt tggaatgaac atttttcata tgacttccga cgaagcaaag  22320
aaacttgctg aagaagctaa agctaaaaaa gaagaaaacg aatattggaa aactactgat  22380
gtagttacag aatacaccaa agatttagag gaaatcaaat gagtccattc ataggtatta  22440
caagcgctgc attagtatcc ggtagcattt tactggcggg tttaggtgtt gttccagccg  22500
tagcaggagg tcttcttgcg ttcggcattc aacgtgttat catgacagtt atcacagtca  22560
tgcagtaatt ttagggagag ccgaggctct cccttttta tttcaaaaat tttttcacaa  22620
aacggtttac aaccaaagca tactgtggta ctatacaact atcaactact gatacagaat  22680
tacggagatt agaaaatgtc taaagtaact tacatcatca aagcttctaa cgatgttctg  22740
aatgaaaaaa ccgctgcgat tttaattacc attgctaaga aagatttcat tacagctgca  22800
gaagttcgtg aggtgcatcc agatttaggt aatgcagtag ttaatagtaa tattggggta  22860
ttgattaaaa aaggcctggt ggagaaatct ggtgatggat taatcattac aggcgaagct  22920
caggatatta tttcaaatgc agcaacttta tatgcgcagg aaaatgctcc tgaactactg  22980
aaaaaacgag caactcgtaa agctcgtgag attacttccg atatggaaga agataaagac  23040
ttcatgataa aacttttaga tgaaaatgga tttgttctta aaaaggttga aacttaccgc  23100
agtaactatc ttgctatttt agaaaaacgc actcacggaa ttcgtaattt tgaaattaac  23160
aacaatggaa atatgcgaat tttggatac aaaatgatgg aacatcatat tcagaaattt  23220
actgacatcg gaatgtcatg taaaatcgct aaaaacggta atgtgtatct tgacattaaa  23280
cgctcagtag aaaacattga agcagtaatc actgtagcat ctgaactgtg aggaataaat  23340
aatgaacaag ttagaaattg ttaatgaact tcgtcgttgc gcagaaccta ctcaagaggg  23400
ttgggatatt tggtaccatg gagcttatct tggaactatc gtaaagatta agactggtaa  23460
atacatgatt attcgtgaaa gtaaagatgc tccagtaggt attcgcaata attttatggc  23520
agcgataagt tcatttacgg atgcagctta cgaaatttac cttgccgatt ataaagaatt  23580
ccaggaatct caaccggtta ttcgctcaat tggtgctaac aaagctcagc agaaaacttt  23640
gtggcaacgt attaaaggat ggtttaaatg aacccattta tcaatcgttt aaaaatgctg  23700
aatgttcctt tatctcgtga gactccagaa agtcttgttg aaaaatttaa agcgcatggt  23760
tataaatgca cagaagaaga tattctgaaa gaagttcctg aaatctgttg gcagactgca  23820
tattgggatg aaaaccaaaa gtatcaacga cgaattgtct gtgcagctaa tcgttttaaa  23880
ttaaaagatg gacgaactct tattattcca ggtgctcgtc attattctaa ggatatggca  23940
```

```
gaagttttag atgtagttaa acctcaatta gttactcaac aagtttgtga tgatgaccaa  24000
gggtttattg accaatatag taattattgg acacgtgaag aagcaatgat tattgcaact  24060
tacgctggac aagtacgtat tgaacgcggc ggtagtgaaa aagaacttta ctctgaggac  24120
ctttactaat gaatattaaa aagtttcaaa ttgatggaat tacgaatcaa atccaggcgc  24180
tggaatatgc caataaaatg atgtcaacta attggggaat ttatgccaat gaaccggcat  24240
ttcagttctg tgatatggaa ttcgctaaaa agctcgtagg aaaaaattat gtatgcccat  24300
ttagttctcc agtaaatgga atgctaaaac ccgctttacg cgatctttat attgcgatga  24360
acgaagaaat gataaaagaa ctaaaacgtc aactgaaggt gattcaattt gaccagggaa  24420
attaattcaa aatccgatta ttttaattct ctcaatgata aagataaaaa tttaatacgg  24480
cattttattg ttgagatggg atatactgac acacgtgatt taagagaaca tatatttgaa  24540
tgtggtgtag ctaaaaagtt ttcattcaca tgcaaatgtt tgagagaggt aattcagcac  24600
tatgaacaat ttagtcgcaa aacataattt taataaagct tctgtccata aggataagaa  24660
gaaagcgttt aaagaatcta atcgcaaaca gaaacataag gggaaggtct atgattattg  24720
attctcagtc tgtggttcaa tacacaatca aaattgatat tctagaaaag ctatataagt  24780
ttttaccaaa tttataccac tcaattgtta atgaattagt tgaagaactg catcttgaga  24840
ataatgattt cttggttgga acttataaag acctctcaaa agcaggatat ttttacgtaa  24900
ttccagctcc aggaaaaagt attgatgatg tattaaaaac tataatgatt tatgtccatg  24960
attatgaaat tgaagattat ttcgaatgag tcataatctt gaaaaggtaa tcgagcataa  25020
tgtagctcag gaacgtaagt cgttcaagga attcgtagaa aaaatttttg aagaaaatac  25080
cacagaccag tttacaaatc aagcgtctga tgatattata acaaagtcaa ctaattgagt  25140
ggtatagtta atgaataaaa atattgatac agttcgtgaa attattactg ttgcgtctat  25200
tttgattaaa ttttccagag aagatattgt tgagaatcgc gctaatttta ttgcatttct  25260
gaatgagatt ggagtaacgc atgaaggtag aaagttaaat cagaattcat tccgtaaaat  25320
tgtttctgaa ttaactcaag aagataagaa aaccctcatc gacgaattca acgagggttt  25380
tgagggtgta tatcgatatc tagagatgta tacaaacaaa taattattta gcccttccta  25440
atattctggc cgcctgagca catattgatt caaggcggtc attacttata tgatcatttc  25500
tataccagta catggttatt gttccagcat agatattatc caaattgaaa tatggacaac  25560
tgtacatgta atttatttcg ggagtaggct ttttagtcgg taaaaaagca aattttgagt  25620
tggaataata atgacgtcca tttaaatgaa ctgcatattc atccatagtt ttatcaacag  25680
gatatcctcc aagtgatttt tcacttatcg ttgaaggtaa ttttccttca tatgctataa  25740
tatcaacaaa atagtttaag tttttagggc ggaaagaata caccgcacta aagtctgcct  25800
cagatgatat atgaactatc tggagttgtt ccagggcgac agattcaaag cgtgcatttc  25860
tttcctttc aataatttca ctgtatgttt catactttga ttgcttatag tactcaaaga  25920
aactatctcc cctataccaa acaatcgcca ttataaacaa aagaattacg acagctaccc  25980
gggaagcaag aactttcccg gtagcgttat ctttgaacaa gcgatctaga acacccaaca  26040
gaatatcaga gggcgaaaat gatattctag gtgctgccat agaccctcct tttaaggata  26100
tttattcaaa ttatactctt ggaccatata ttgctccaac attttgccat gtcggtgtag  26160
accctatgac ggcataacca gcagcaccgc cgtcatattc tgtaccggta ccgtgagtat  26220
tacatctacc tcctgcggag ccaacttcac cgccattccc gcctgtatat gcactaagag  26280
```

-continued

```
acccctcacc gacagatcct gcacccggag cgtaaatagt gccgctggtt gcaccagcac  26340
tcatatgaga ggaagaccca ccagcgccaa atggacgacc gcctccgccg ccaaaggata  26400
gtctacccct gttgccgccg ccgccgccgc cgccgcctcc agcaatagct ccgccattat  26460
taattcttag tctcccacca atatcgtttt gaatacaatg acctccagct gaaccaggac  26520
tattgctacc gccattaccg ccacgtccat acatcgttac gccgtgtatg ttcagttgaa  26580
catattcatt cggtgtatct ccgtacatga agaataaagg aacatctcta gaatatgata  26640
ctaaatctcc agtgatatta aacactatag gtgcactacc tgcctcaaaa catctatctc  26700
ggaaccattg accgttgaag ttatggtctg ctccaagcgt gtgaattatt tcaacagatc  26760
gacctatcat attactcatc caaaatggag cacccattct taatcgttgg gccgcgccac  26820
ccatccaatt ttgtcctgta ttaactactg cagacgatcc tacccacggt cctgttactg  26880
ccatataaac ctccaagggg ccgaagcccc tcttattatt ttaacaatga tttaactaat  26940
gctttaagtt cttcgatttc tgatttaagt tctgcaattt ctgcggtatg ctcattgatt  27000
gcagctgtat ttaaaccaat tacaccgtta tagttcaaac gaagtaaagc ttcaccatca  27060
gggtcacctt caactaattc tggtaaaata gcttgaactt cttgagcaat taaaccggcg  27120
ttaggttccc atttctgatt accttcctca tccaggcctc gcttctgcat ataagtgtaa  27180
ccattaattt tggaaagctt ctcagaagca ttttcaaatt taacaaggtc tttttttaacg  27240
cgaatatcag aacggacata aacatcacgg acaaacgttg aataactatc atttgcctga  27300
acgagatgcc cataagaaac gatagctctt ccaacttctg tccaaaaagc accggttgaa  27360
tcccaaagcc caggatgaga ttgatagcct gcgccccagc ttgcaatatg tataccattg  27420
gcaaccatat tgattcggcc gtcactacca tgaactaatc cggtatcatt atcaccgata  27480
gcgatagatg ctccacccca taccggaatt gtgccgacgc ccaagttaac accagcgcga  27540
agtccagccg gagctttaaa atcaccattt atcccaaact catatattgc attaggatga  27600
ctgctatctc cgctttctgc ggaaccaacg cgaattactg catttcccca agtagcattt  27660
ccgcctaatc gaataatacc aaaatctgct tttgttgcat atccttcgtt aatgatttgg  27720
cttcttcctt taattatagg catatagcta tctttcggaa cagattcacc aaagtcaacg  27780
aagaatgggg cttctgtttg ccattgctga ttatatccgt gaccttgggt agctgtccac  27840
tgtcttccgt ttaaatataa acgataaaaa tttaatgaag ctgcagtagc ttgattttta  27900
acattaaagt caatatcgcc tacattatta agaataattc ctgccgtagt cttaaaatta  27960
taaaatgaag cagtgtcatc tgccccgcct ttaccgatgt accatgaatt cgctccacct  28020
gatgttccaa gtaaataagc agaatcattt tcatcggcag caatgttaat agcgtcagat  28080
cctcttttaa cgattaattt accagtcatc gtatcgcctt ctttagcaac acgagtagca  28140
atggcatcgc gaatattagt tacgtcgcct gctgaagtaa atgttttcca gatgtcagac  28200
cagatgttac cattgcgagc aatagtagct tcaccgccgc cgacagaaac gttatctggg  28260
aagttaacag taccgtcttg attaaaacga gacgtatggc cttgtgaacc atcttctttc  28320
agatgatgaa taacgaatgt acccgaatta atttcagtac ctaaagacca aacagcttta  28380
ccgtttaaaa acttctgctt aacaatagga taatatttgc ttatagcatc atcatcgatt  28440
tcctgaaaaa taggagctgc ttgaacatac tgaatatcat aaccgccagc accagcgccg  28500
tgaccgccga atttaatata accatttgcg gcaaaagaag cataacttaa atctaaatca  28560
ggaataacga ccttacctgt atctaaagcc atactaaatg ggcgaagtgg accgatatcg  28620
ccatttttgc cttcaccata agcggtcgga ataatgtgaa gactgccttc tgaacgtcta  28680
```

```
aaaatgactc cataatctgc attccaaatg cgaagcgcat tcacggcccc agatgaaatt  28740
tcacccgttg tgtgaactcc tctatttcca gcagtaacac cagatgattc aaatgaaccg  28800
ttaacgttca tttctacttc accggtagta agtctttgaa tatagctcat ccaactagtt  28860
gcatcagaaa tttccatgac atttttacga ttacctacac taggattagt aaacgtgtta  28920
ccccatacgg aaattgtcat attatcaact gaactactac cagttgtgtt acctctaaac  28980
atcaatgtag aagaattatt tctaccatcg atattaacag aaccaccaat aacatcaata  29040
ttaccaggag taactaataa tcctccagcg gtattaatat tagttgttcc tcttccacgg  29100
aaataatgat gatatctacc accttgataa tatcctaaaa gagtctgacc atctccaaac  29160
gcgttattat catgatatgt aacgacagta gcgagagcat agttttcagt aggaggagta  29220
gttaaatcgg ttccgttagt agaatatcca gctacaaatt ttcttaggct agttgtttcg  29280
ctaggactaa ataaaaatgt tttcgttcca ttattgacgc taaaataata tccatcctga  29340
taccatttaa atccagtatc attatctcca agagcaattg aagcagtccc taattcagaa  29400
tatcctttag agccacccgg aagacctata gaaatagaat gacctgcttt caatccaccg  29460
gaccaggtaa acgaccaaag ataggcctcc aacccgtcac cggcgtacca agttatcccg  29520
tcattatctt taacttcgtg gaatatacca gatcctactg catttcgcat aacacgaagg  29580
tggttaatag cagtttcgct ttctgccaat ggagtgttat ttgctaatga atagatgtca  29640
taatcgcctg tcttcttccc atctgtaata actttatcag tcaaaatctg aggagttgac  29700
atagatttcc atgctgatac ttcaggtgaa gtaaataggc cattgcctga aaatgcataa  29760
gtgctttcgc caccagcggc gtagtcatga accctgatat taagtacttg tgtagttaat  29820
ccatcattag ccggtgaata aatgattcca cgttcgcggc tattgctatc gaaaaaacga  29880
acatgtgatg tacctgaact ttttgtaata agttccccac cttcagtcat aatctgcccg  29940
gcggcaataa tatcgcgagt tactcgagca ataccgatta aattaaaatt acctgtctga  30000
gtgaaggtgc catttaaagt ataatcacca gtttgattat agtttcctat atgaataaca  30060
ttcccgtcaa tgctaccgcc tttagcaaaa cccagatcaa taatatttcc ttggtcatct  30120
ttagtaaaaa gtacacggtc ttttaagttt atagccaatt caccttcggc taatactgaa  30180
gcggcaggac gtgctcctgc ggttttgctt cttttaaatt gtatttgttt taaagtagcc  30240
ataagtcctc ttaataatag ccgaaatctt gaacagaatc cttaataaca atttgatcaa  30300
atcgtggaac atgtgatggt tgagatgcag gattctgcga aaaaaggttt ggcgcggtta  30360
agttacctgt catagtatct ccagagcgta ataccctaga gtttgcgttt gctgtaacaa  30420
tatttattgc tccatcgaca taatctttcc gcgtgaggtc ataattattt actggagata  30480
atgaagttgc gcgtatttgc gatgcttcaa ttacgccctt tgagctaata tctccatttc  30540
gtgtgttaat tactacagtt ctacctgctg ttccttgtga tgatttaaaa ccaataccat  30600
accacgaaac aatatccata tttgtagtat catacgtggc attatcacca ggaccagcaa  30660
aaataccgtt gtcacctgac cctgcgccag gaacagtcat tcctttatta aaaattactt  30720
tatttaaata cgtaccgcca ttagctttag aaacgaaatc gttatcggca gcttgtggct  30780
tattatattc tgaatatatt ttaaatgatt tatagagtac atcgtcaccg gctggattca  30840
atggaaaatt tccttgatgc caaatgacag agcctccagt tgttgaacct acttttaaat  30900
cagccattgt atgccccttt attttaatag tatttataaa gaaaaaggga acccgaaggc  30960
tccctcaatt taaacttctc taaattcttg tccaaacact ttaccagttt tagacgatgc  31020
```

-continued

```
ttgtgtagga agtaccatta tatccggagg tgaagcagat tcacagacat aattaactcg  31080
aataccattg acgccaaatt cagcaggttt tgaaattcct ccatttcttg atacttcaga  31140
aaagcttaaa tttctcatgc caccttgacc tgcttgcgca gttctttgtg catatatcgt  31200
aaatcctact gcattttctg gaataactac ataatcttcc tttaattccc atgacccagc  31260
ttgtccagta aactcagcat gtgttgaaga aatatatcca ttcgattcat cataaaaacg  31320
gatagatata tttgtagttc caagcgcaag taaatcggca tcagcatata gctgtgcttt  31380
aagataaaga acatcgccag gaattaaatt ataatcagag agtttactta tcgcggatga  31440
agttggtaaa cgtgcaattt cgttattagt tccaccaacc gctgacataa attgctcaac  31500
gctttcgtat gttcttttag gaaatcctgt agctccaacg tcttctaaac tatcaaatac  31560
aacatctaaa atagtttgat agtcatctgt gctttttcta ttacttagtt taacatgttc  31620
caatgcaata gctcttttag aagaagtata aaaggcagca tatgatacgt caaatcttga  31680
caatacagaa tcagatggaa aagcagacgt tcctgcggtt cttatccaag atactacctc  31740
aggaggaaaa ttaacttttc cgttagttaa tatagcaaca agtctattat tcgtcaaaga  31800
gttcatgaaa ctaacaaaag cagctgatgt agtatcattt gaagtcgaaa aagcatatga  31860
cttactatca actaatgctc ctgtagaagg gtcaaaaact cttaaatgaa gtcctgcgct  31920
aaatgtttga cttccaacag gattatcctg aaatttaacg tatggtcctt ctgcagtaga  31980
aagcgggcaa gaacccgcta tacttatttt atatcttact gaattgcttt ccgataaaaa  32040
tggcgtttgg acatatcctt gtccaaactc tgccataaat ttttccataa tacctcttat  32100
tcaacccatt caaatttaac cgttttattc actgggtcag gaataatgcg aacattacca  32160
attcgtaaga aatcacgaat agtaagattc cccattatag cattatcaga tggtaaagca  32220
ccgatatcag atggctgagg agggttacca ccatcaaata cctgaacaaa acttgaccaa  32280
gagtttttgg ttttctgcca tgtacgcgtc cagcgagtgg tgcgcgcttc tggggacgtt  32340
ggataagtaa tccaatcttg gtaaagtgaa tcgagtgtgt taccaaactg agtcaatgta  32400
ccaggagatt taacctcttc gccacgttct aagtatggaa gcccagtcac ttcattagtt  32460
ttttcaacca tttcaaaata acccgggaac tggttataag tggctgaatc attaatatcg  32520
attgaccaga atcctacagt atcagatgtt ggcgcacggg tatataaatc agaggtttta  32580
gtaccctgag aacgaattct cgagttaaca gtcaaaccac ctgaatttat agtagcacct  32640
ttggcaatga ttaagctttc accaatcgtt acttgaccag atgcattatt aatagttaat  32700
ggacgtaatc cattaaatcc accagtctga tcgcccgatg cagtaagcat aaaataggtg  32760
ttagcagcat cattacgaat aaagaatcca taatcaccgt ttattgctct aaaagcattc  32820
gacgatttac tgataaattc gccattagca gtaactgaac taccgaatgt tgcaacgcca  32880
ttcgcattca atgttcctga agcattcaca tttatcggtg ttactgtacc attgatatta  32940
aatgttatat taccagcttt attgcgctga gaataaaagt gactagacgt ttcatcacta  33000
acttcaaata cggtagaacg tgttgtgtcc gattcaccac tgaattgatt tccccacact  33060
ctgactgtca tcgtttgagc cggattcgtt ccagtttgag gtcctttctc aaaaatcaga  33120
cgagttgctg ttccagtatt agaaatggtt agtgtactat ttgctgaaac tgatccaccg  33180
aacgtagcag tactagatga tacaagaggg gcactcagat tcgtttgttg ggttaaggtt  33240
agtgaaccat taaccgtttg tgcaatatcc ctacgaatga actgagatga atctagacca  33300
tccagtaaat tactatctac agcttttgct tttaacggca aataatttgc taatacacgg  33360
tttaattcgt atggcgatac tgcataacta tttttctcgt acaattctaa tgactgtgtt  33420
```

```
gaaccaactg tatcattacc aacgaatgta attgaaccag atgaagtttt aacaaaacct  33480
cttaccagag tagtagctgc ccaagtaggt tcactctgca caatccattt taaatttttt  33540
ggagatacag cagtatttgc tgacgttcca gacacagttt cagactgcgt tgcaacttta  33600
ataacacctt cttgcgattc ggtagattta gtacctaaaa gctttttagg agttattaaa  33660
acattatcta atgttcctgc agcagcttca acttgtgtag ctacacgaag cgtaccacgc  33720
tgtgtctcat ttgcttcaag aatattaagg gtataatggt cccagagagt tcctgattca  33780
actaatccag atagagcaac aacagaagta cgatcagtac tatcaaatct agttttaatt  33840
tttaatggtg tagagatacg agtatcgtcg acgcctgcgt cgaattcaac ttgtgtagca  33900
atttcagcta taccacttaa actttcagtt gctttacggt catttaaagt tttaggagtg  33960
actgcacgag tataatcagt tcctgtatta acttcatttt gcgtagcaat ttcaattaaa  34020
ccaattcttg catcagttga tgtcttttta tgtaacgttt ctggtgttac aaccgcattt  34080
gcccatcctt cttggctttg tccagcaatt acttcacttt caactgctaa aattactgca  34140
ccttgttgcg ttggagtagc tttatactga tccaaagctt taggcgaaac aactaaatta  34200
ttagtgtttt tattataaac atttgtacca tttaattcac gactagaagc tggagtagct  34260
cctgcagtag atacaaaggt tacaatacca gataatgatt cagaaccttg tcgagcttga  34320
agctttttag gagtgatgat tgtagtatca tcagtacctg tattagtttc ttgctgtgtg  34380
gcaatttcag cgacacctct acgagtttct gtagcagttc tttcattcag ctttttagga  34440
gtgatgataa tatcgtcagc aaaagagaat gtagtatcct gattcacttg ggcggtagtt  34500
gctattcttg cgatacctct acgagtttct gtagcagtac ggttagctaa tgtttctggg  34560
gtaattgcta attctttttg tggagaattt tctaaatcga cgttagcttg agcttgtgta  34620
gctaaagcaa ttacgcctaa tcttgctcta gtagaattat ttaaagaatc gactctttca  34680
actgttggaa cgttttgctg tacaacccag tattttccgt cagaatcttc gatataagca  34740
agttgtaaaa ctggaacata attagtttca ccgttaaaaa ctaattcttg aacagtcacc  34800
cattcagctt caggtggata ttctgaacgt tttgggaatt gcagcaattg aactgaagaa  34860
gcaattttat cttcaccggc agctttgatt ttaactgttt ggccttttct catgtaattc  34920
atggaaattt taacagtatc accaatggaa atatcggttg gaagctgaag ttcaattgtt  34980
tgagttgttc cgttattcgc accaaatacc ataacttctt catttggacg aatactagaa  35040
ttagttgtta taatacgtaa acgtgcttta ctatccccgt caaacaatct ccacaatttt  35100
tcattatcat catacatcaa gaaaccgtca atcgatgtac gtccttcaat agaatgagtt  35160
ccatcttctt gtattgaagt agtttcgtcg tatgtagtaa caattgtatg ataaagtgga  35220
tttaatttat ctaaatcgac gaaattaata atatcgccat gattagcaaa tctcggaagt  35280
ttaatattaa tcggcgcagc ggaagtaaat ctgcgcacga taaaatcgtt agattgcgcc  35340
tgataaaaac ttgccggtgt tacaactaca gcttctctgc tataatcagc aacatacatt  35400
tgccacagac gattactaaa aattaaaact atctgtgatt ttggatgagt cattagtact  35460
gatcgtactt gctgacctct aaaatttaca atgctttgca ctggagctgt aattaaaact  35520
tggttaactc cgggttttcc accaatatct tgaagaacga tagtatctcc atcaattgga  35580
gaagttggca aagtaaatgt gatatcattt cctgctgcag tattaactga aattgattca  35640
cctgacttta attgataagg tcctgacgaa acagttgtcc agtttgcatc agtacgtaat  35700
gctctccagc gcacgctatt aaaagctcct gccggttttg gaatatcatt tatagcagcc  35760
```

```
caaaagcggt tatcataaat gattacaaaa tcttttaaat atccacgagt tggatcatat  35820
tgttgaactg tgttttcttg aattaggtaa tcaacgttaa caccgtcagt tcctacggca  35880
cgatcagcta aagctacgtt gattatttta tcgccacctg cgtccagacc atcttctgct  35940
ctgaactttc ttttaatctc ggccattctc ccgggctcct attgtgtttt caataataag  36000
tatttatact tgtttacttt aagatttgga tagtatataa tagaaatctc actaattgaa  36060
cgaggttcat atggatttag aaatgatgct ggatgaagat tacaaagaag gaatttgctt  36120
aattgacttt agtcagattg cgctttcaac cgctttagta aacttcccag ataaagaaaa  36180
aattaattta tcgatggttc gtcatttgat attgaactca attaagttta atgtcaaaaa  36240
agcaaaaact cttggataca ctaaaattgt actgtgtata gataacgcaa aatccggata  36300
ttggcgccgt gatttcgctt attattataa gaaaaaccgt ggaaaagcgc gagaagaatc  36360
tacttgggac tgggaaggtt attttgaatc cagccataaa gttatagatg aattaaaagc  36420
ttatatgcca tacattgtta tggatattga taagtatgaa gcagatgacc acattgctgt  36480
gcttgttaaa aagttctctt tagaaggaca caagatttta atcatttcat cggatggtga  36540
ctttactcaa cttcataagt atccaaatgt taagcagtgg tcaccgatgc acaagaaatg  36600
ggttaaaatt aaaagcggtt ctgctgaaat tgactgtatg actaaaatcc ttaaaggtga  36660
caaaaaggat aacgttgctt cagttaaagt acgatctgac ttttggttta ccagagttga  36720
aggtgaacga actccttcaa tgaaaacctc tattgttgaa gctattgcta atgaccgcga  36780
gcaagctaag gtgcttctca cagaatctga atataatcgt tataaagaaa atttagttct  36840
aattgatttt gattatattc ctgataatat tgcttcaaac attgtgaatt actataattc  36900
atataaatta ccaccgcgtg gcaaaattta ttcatatttt gtaaaagcgg gtctttctaa  36960
attaactaat agcattaatg aattttgagg tgaataatgg ctaaaaaaga aatggttgaa  37020
tttgatgaag ctatccatgg cgaagactta gctaaattta tcaaagaagc atctgatcat  37080
aaactgaaaa tttctggtta taatgaattg attaaagata ttcgaattcg cgccaaagat  37140
gaacttggcg ttgatggtaa gatgtttaat cgtcttttag ctttgtatca taaagataac  37200
cgtgatgtgt ttgaagctga aactgaagag gtagttgaac tttatgacac agttttctct  37260
aaatgatatt cgtccggtcg atgagaccgg tctttcagaa aaagaacttt caattaagaa  37320
agaaaaggat gaaattgcaa agcttcttga ccgtcaagaa aatggattta ttattgaaaa  37380
aatggtagaa gagtttggaa tgagttatct tgaagctaca acagcattct tggaagaaaa  37440
ttctattcct gaaactcaat ttgctaaatt tattccttcg ggtataattg aaaaaattca  37500
gtcagaagct attgacgaaa atcttttacg tccttctgtt gttcgttgtg aaaaaactaa  37560
tacattagat tttctactat gattaaactc cgcatgcctg ctggtggtga aagatatatt  37620
gatggtaaat cagtttataa attatactta atgataaaac aacatatgaa cggaaagtat  37680
gatgtaatta agtataattg gtgcatgcgg gtgtctgatg ccgcttatca aaagcgaagg  37740
gataagtatt ttttccagaa gttatcagaa aaatataaat taaaggaact tgctttaatc  37800
tttataagca atcttgttgc taaccaagat gcttggattg gtgacatctc tgacgctgat  37860
gcacttgtgt tttatcgtga atatatcgga cgcttaaagc aaattaaatt taagtttgaa  37920
gaagatattc gcaacattta ttattttagt aaaaaagttg aagtttctgc ttttaaagaa  37980
atctttgagt ataatccaaa agttcaatca agttatattt ttaaactact tcaatcgaat  38040
ataatttcgt ttgagacgtt tatcttgctt gattcgtttt taaatataat tgataaacat  38100
gatgaacaga ctgataattt agtctggaat aattattcta taaagttaaa ggcttataga  38160
```

```
aaaattttaa atattgattc acagaaagct aaaagtgttt tcattgaaac tgtgaaatct  38220
tgcaagtatt gatatgaata tagtatattg gtttacattt gaagaccgtg tcaaaaataa  38280
gactccacca tactactata tcggtagtaa attaaattgc tcatttgaga acggaataat  38340
atatgactct tccggaaagg aatactggag ctcatgtaaa caaaaaagat ttttgaatgc  38400
gctaatgctt caaaaaccga gcgttaaaat aattcaaatt gatgatgact tggatgttat  38460
tgaagcagaa cgaaaatacc aacttgaagt aaatgccaga gataatccag actattttaa  38520
tctggtatat gctggtggtg gatttggtgt gagtggtgaa actcatccag ccaaagaccc  38580
ggaagttaga gagcatatga gattggctaa ttatatgaac cgtgacgatt ttagaccttg  38640
gaaaacatca cgagctaata tagagtcttg gaaattatct catattgctt atgagaatta  38700
tgtgttatta ttatcctcta atctgtacgg taaaactcct ggatggcgaa gagttaaagg  38760
taatataaat ataactgata caactgctaa atcgatggta aagtatttca actcaggttg  38820
gatacctctc gaagacccag agtattgcaa attatgccag ctatgaggta aagtgtcata  38880
gcaccaactg ttaattaaat taagttaaaa aggaaataaa atgtttaaac gtaaatctac  38940
tgctgaactt gctgcgcaaa tggctaaact gaatggcaat aaaggttttt cttctgaaga  39000
taaaggcgag tggaaaccga aactcgataa tgcgggtaac ggtcaagcag taattcgttt  39060
tcttccgtct aaaaatgatg aacaagcacc attcgcaatt cttgtaaatc acggtttcaa  39120
gaaaaatggt aaatggtata ttgaaacatg ttcatctacc cacggtgatt acgattcttg  39180
tccagtatgt cagtacatca gtaaaaatga tttgtacaac actgacaata aagagtacag  39240
tcttgttaaa cgtaaaactt cttactgggc taacattctt gtagtaaaag acccagctgc  39300
tccagaaaat gaaggtaaag tatttaaata tcgtttcggt aagaaaatct gggataaaat  39360
caatgcaatg attgcagttg atgttgaaat gggtgaaact ccggttgatg taacttgtcc  39420
gtgggaaggt gctaactttg tactgaaagt taaacaagtt tctggattta gtaactacga  39480
tgaatctaaa ttcctgaatc aatctgcgat tccaaacatt gacgatgaat ctttccagaa  39540
agaactgttc gaacaaatgg ttgacctttc tgaaatgact tctaaagata aattcaaatc  39600
gtttgaagaa ctgaacacta agttcagtca agttatggga actgctgcta tgggtggtgc  39660
cgcagcaact gccgctaaga aagctgataa agttgctgat gatttggatg cattcaatgt  39720
tgatgacttc aaaacaaaaa ctgaagatga ttttatgagc tcaagctctg gcagttcatc  39780
tagtgctgat gacacggacc tggatgacct tttgaatgac ctttaataga ttatattact  39840
aattaattgg ggaccctaga ggtccccttt ttttatttca aaaatttttt cacaaaatgg  39900
tttacatccc tgttcttcta tggtactata caactatcgg caatactgct gacgattaaa  39960
gaggaaaaca atatggctaa agttgatatt gacatcgttg attttgaata tattgaagag  40020
attattcgta atcgttatcc tgaacttagt atcacaaatg tacaagattc taagttttgg  40080
agtattcaaa tcgttattga aggtcctctt gaagacctca cccgctttat ggctaatgaa  40140
tactgtgatg gcatggattc tgaagacgca gaattttaca tgggactgat cgaacaataa  40200
ttattaaggg gctatcaagc ccctattaaa atgaggaaac attatgtata ctggtagaaa  40260
gtatgaactt gttccaagac ttattgatac atttattaat tatagcccac gttctaattc  40320
atcaatagtt aaagctattc gagataatgg cggatggttt gaagttaaag aagtttccgt  40380
cgctaatgga tataaagcag taaaacacat tgaatgcgca aatggaaaac atttttacct  40440
caaagataga cttttagaaa tttgtgaaga cgaatttcat tgttttcgtg agtataaaga  40500
```

```
accgacttct gaagaagatg aagtcgaaga caagatttct ggcgtaacaa aaattcactg  40560
cattgttgac gaaaacaatg tagatgaaat cattgaactt ttgcgaaaaa ctttcaaaaa  40620
gtagtttaca gaagggtagt agtgtgatac tattacccta tcaattaagg agaataaaat  40680
gagattacaa cgccagagca tcaaagattc agaagttaga ggtaaatggt attttaatat  40740
catcggtaaa gattctgaac tcgttgaaaa agctgaacat cttttacgtg atatgggatg  40800
ggaagatgaa tgcgatggat gccctcttta tgaggatgga gaaagcgcag gattctggat  40860
ttatcattct gacgtcgatc agtttaaagc tgattggaaa attgtgaaaa agtctgtttg  40920
aggaaaataa tatgattttt gtatttgaat ttatgaatga tgaattcgat tatgcaattt  40980
ttaacgcatt gcataatcct gatttaaatg aatttaaaga aatgttttct gacgctttaa  41040
gtatgtcaga agaatactgt ggagaatgtc aacgtgtttg tgtgacagtt tttgaaaaca  41100
aagaaaagac atatgaagaa ttattctttg atgctaataa agccactgaa tggtttattg  41160
aaagggggt tttgagtaat gattaaattg gtattcgctt attctccaac taaatcggtt  41220
gaaggcttta atgaattagc attcggttta ggtgatggtt taccatgggg acgagttaaa  41280
aaggaccttc agaattttaa agctcgtact gaaggtacaa ttatgattat gggtgctaaa  41340
acgttccagt cattgcctac attacttcca ggtcgtagtc atattgtggt atgtgacctt  41400
gcgcgtgatt atcctgtaac caaagatggt aatttagcac atttctatat tacttgggag  41460
caatatatag attacatttc tggcgacgaa attcaagtgt caatttctgg cgcgccattc  41520
gagactgtgc ttgatcagaa ttccaaagta agtgtaattg gaggacccgc tctactatat  41580
gctgcgttac cttatgcgga tgaagtagtt gtttctcgta tcgttaaaaa gcatcgtgtt  41640
aattcaacag ttcaattaga tgcaagtttt cttgatgata taagcaaacg tgaaatggtt  41700
gaaactcatt ggtataaaat agatgaagta acaaccctta cggaatcagt atataaatga  41760
gcaataaatt aaaagttaag gatgttccta atgctatggc ccttttttatt tgtcggcaga  41820
tgcatcaagg gcctatgaca ccaaaacaat atcttaaagg tgagcgttct ttaggattta  41880
ctcgcaaagc aaaacaaatg gttaaattag gatataagcc taactttgcc aaatatcctt  41940
ctacatattc ttggatgaac taatgaaaca ataccaattt ttaattaaag atatcctgga  42000
aaacggttat gaaaccgatg accgaacagg cacaggaaca attgctttgt tcggtactaa  42060
attacgctgg gatttaacta aaggttttcc tgcagtaacg actaagaagc tcgcctggaa  42120
agcttgtatt gctgagctaa tatggttttt atcgggaagc acgaatgtca atgatttacg  42180
attaattcaa catgattcat taattcaagg caaaacagtc tgggatgaaa attacgaaaa  42240
tcaagcaaaa gatttaggat atcatagtgg tgaacttggt ccaatttatg gaaaacaatg  42300
gcgtgatttt ggtggtgtag accaaattgt agaagttatt gatcgtatta aaaaactgcc  42360
gaatgatagg agacaaattg tttctgcgtg gaatccagct gaacttaaat atatggcatt  42420
acctccttgt catatgtttt atcagtttaa tgtgcgtaat ggctatttgg atttgcagtg  42480
gtatcagcga tcagtagatg ttttcttggg ttaattgagg cctgagtata aggtgactta  42540
tacttgtaat ctatctaaac ggggaacctc tctagtagac aatcccgtgc taaattgtag  42600
gactgccctt taataaatac ttctatattt aaagaggtat ttatgaaaag tggaatttat  42660
cagattaaaa atactttaaa caataaagta tatgtaggaa gtgctaaaga ttttgaaaag  42720
agatggaaga ggcattttaa agatttagaa aaaggatgcc attcttctat aaaacttcaa  42780
aggtctttta acaaacatgg taatgtgttt gaatgctcta ttttggaaga aattccatat  42840
gagaaagatt tgattattga acgagaaaat ttttggatta aagagcttaa ttctaaaatt  42900
```

```
aatggataca atattgctga tgcaacgttt ggtgatacat attctgtaca tccattaaaa  42960
gaagaaatta ttaagaaacg ctctgaaact gttaaagcta agatgcttaa gcttggctct  43020
gatggtcgga aaactcttta cggtaaaccc ggaagcaaaa atgggcgttg gaatccagaa  43080
acccataagt tttgtgaatg tggtgttcgt atacaaactt ctgcttatac ttgtagtaaa  43140
tgcagaaatc gttcaggtga aaataattca ttctttaatc ataagcattc agacaaaact  43200
aaatctaaaa tatcagaaaa gatgaaaggt aaaaagccta gtaatattaa aaagatttca  43260
tgtgatggga ttatttttga atgtgcagcc gatgcggcta gacattttga aatttcatca  43320
ggattagtta cttatcgtgt aaaatctgat aaatggaatt ggttctacat aaatgcctaa  43380
cgactatccc tttagggagt agggtcaagt gactcgaaac gatagacaac ttgctttaac  43440
aagttggaga tatagtctga tctgcatggt gacatgcagc tggatataat tccggggtaa  43500
gattaacgac cttatctgaa cataatgcta ccgttcaaca ttgcatcata tgctgcgtta  43560
gttcatattg tagctaagat gtgtaatctt attccgggag atttgatatt ttccggtggt  43620
aatactcata tctatatgaa tcacgtagaa caatgtaaag aaattttacg tcgtgaacct  43680
atggatttat gcgaattgca attaaaattt ccagatgaat ttgatgaatg ggacacagaa  43740
tcgcaggtat tttggttgag tcaattcgca aagccgcata attttgttct taacaactat  43800
gaatcacacc ctcctattaa aggaaagatg gcggtgtaat tttaatttaa ttgcgaggat  43860
atatgatttt acgatttaaa gatacttctg gtgtagttct ttttacactt cctaatccaa  43920
gtgagttaga agttccagga ccagaacaac ctattatcat ttatggtaaa aagtattata  43980
ctcataaaat gactcgtgag tattttgata ataaaatttc cacagttaaa acttcttctg  44040
attgttatta tgatattact gttttaacgg aaaaacaata tgaagaatgt agaactttag  44100
cagtataaat atgattccca acaatctaga gcacatcttt tagatataag ttttctgctt  44160
attccggttt gacgcacagc ttctgctatt gttggatatt ctaccccatc tatacttact  44220
cttagatggg gtttcttttt acctctttgt gagtcagaaa ttcgttttct aacttcattg  44280
gtatgtgtct gtccataata tggattattg atgcctttca tattaagcgc agcgtttctt  44340
tcttggaact ttttgcttag ttctatagca cgatctaacc catagtgttc ttctatagtt  44400
ttacctttga tatctttagg tctaccatgt ttttgcttaa gttcttctgg tgataatttt  44460
gaattattat ttttaattgc atttgaaatt ttattaagga tttcttgctt tcttgggtga  44520
tgagataagg tatccccaaa cgatgcgtct gctatattat acccattttc ctttgagtca  44580
tattcatgta tccaataatt ttcacgttca ataatgatag atttttcgta tggaagttct  44640
tctatgattt tacatacgaa agcatctttc ccatgcttat tataagaacg ctgcagcttt  44700
attgaatgat gatttccatt atctaaatct ttaaagtgtc gtttccatcg ttcttcaaaa  44760
ttaattgcac ttcctatata gtgcttattg gttttagtgt ttataatagc atatattcca  44820
gatttcatta tattctccta tataaaatta tatttatatg gggtaactta ctacagagga  44880
cttatgcaat taattaatgt tatcaaaagt agtggtgttt ctcagagctt tgacccgcaa  44940
aaaattatta aagttttatc ttgggcagct gaaggaacat ctgtagatcc ttatgaatta  45000
tatgaaaata ttaaatcata tctccgtgat ggaatgacaa ctgatgacat tcaaactatt  45060
gtaattaagg ctgctgcgaa ttctatttca gttgaagagc ctgattacca atatgtagct  45120
gcacgctgtt taatgttcgc tcttcgtaag catgtttatg ggcagtatga accacgttca  45180
tttattgacc atatttctta ctgtgtaaat gaaggtaaat atgaccctga attgttgtca  45240
```

```
aaatattcag cagaagaaat tacattttta gaatcaaaaa ttaagcacga acgggatatg  45300
gaatttactt attccggggc gatgcaatta aaagaaaaat atctagttaa agataaaacc  45360
actggtcaaa tttatgaaac tccacagttt gcatttatga ctattggaat ggcactgcat  45420
caagatgaac ctgttgatag attaaaacat gttatccgtt tttatgaagc agtatctact  45480
cgacagattt cattgccaac tcctattatg gctggttgtc gtactcctac tcgacagttc  45540
agttcatgcg ttgttattga ggcaggagat tcattgaagt ctatcaataa ggcttccgct  45600
tcaattgttg aatatatctc taaacgcgct ggaattggta ttaacgttgg tatgattcgt  45660
gccgaaggtt ctaagattgg catgggtgaa gtacgccata ctggtgttat tcctttttgg  45720
aaacattttc agactgctgt taaatcatgc tcacagggtg gaattcgtgg cggcgctgct  45780
actgcttatt atcctatttg gcatttggaa gttgaaaatc ttctcgtttt gaaaaataac  45840
aaaggtgtag aagaaaaccg tatccgtcat atggattatg gcgttcaact gaatgaccta  45900
atgatggaac gattcggaaa gaatgattac attactttgt tcagtccgca tgaaatgggt  45960
ggcgaacttt actattctta ttttaaagac caagaccgtt tccgtgaatt atacgaagct  46020
gcagaaaaag accctaatat tcgtaaaaag cgtattaaag cccgtgaact gtttgaattg  46080
ctcatgactg aacgctcagg aacagcaagg atttatgtgc agttcattga taatacgaat  46140
aactatactc catttattcg tgaaaaggca cctattcgtc agagtaactt gtgctgtgaa  46200
attgctattc caacaaatga tgtgaatagc caacaaaccc gtttaatcaa aattaagaag  46260
tcggatgtag ctaagtttta tgaagctaat cctggcggta taattcaaag caaataaagt  46320
acacagaccg ttaataaata atccataaca agaggaaaag ttatggatta ttctaaaatt  46380
tacaataacc ttatttctaa agctaagaac agaaaattag attgctatac cgaatcacac  46440
catattatac ctctgtgtat tggtggttct gatacaaagg aaaacctggt agatttgaca  46500
cccgaagagc attacatagc tcatcaatta ttagtaaaga tatatccaga taatcataaa  46560
ttggtatttg ccgctaatat gatgtgtgtt tattctgaag ataatattga acgaaagaac  46620
accaataaac gccatgggtg gcttagaaga aaattggcta tttctgtatc tgaaaataat  46680
aaaggcaaac cagcttggaa caaaggtatt ccggtaactg acgagcatag agaaaaactt  46740
caaacaactt gggtatttac tttcccggac ggtcatgaag aaatccataa aggcctaaga  46800
gaattttgcg aactacattc actcaatgct tcggcaatgt cggccgtatg caaaggcaaa  46860
aggtctcaac ataaaggctt taagtgtcga aagcttgata atatctctga aaacgataat  46920
caagaatacg tcagtaaacc tcatccaaag ggattaaaac cccataactt aattgctgta  46980
aaaataaacg gtatagaata tcaatcaata catcgagcat ctaaagctct aggaatatct  47040
cgaaaaaagg tagaagaatt aaatgaatat tgattatgaa tttgtagatg aattttacga  47100
agatgatgag tatacaacaa tacaagttat tgaaaacaaa ggtgaagtgg gcctctgcac  47160
tctctctgca ttcgtactag ataattttga ctggcaagac caagataaaa ttaatgaatt  47220
ggcagaagtc caagttcgtg ctcttgataa tcttttggac taccaaggat atccagttcc  47280
tgaagcagaa aaagctaaaa agcgtcgaaa ccttggcgta ggtgttacta actatgcagc  47340
ttggctggca agtaattttg cttcttatga agatgctaac gatttaacac atgaactatt  47400
tgagagatta cagtatggac tcattaaagc atccattaag ctcgccaaag aaaaaggacc  47460
ttgcgaatat tattcagaca ctcgttggtc tcgaggcgaa ttacctatcg actggtacaa  47520
taaaaagatt gaccaaatcg cagctccaaa atacgtttgt gactggtcgg cgctgcggga  47580
agaccttaag ctctttggca tccgtaatag cacattatca gcacttatgc catgtgagtc  47640
```

```
atcttcccaa gtttctaaca gtacaaacgg tatcgagcct ccacgtggac cagtctctgt  47700
taaagaatca aaagagggtt cctttaatca agtcgtgccc aatattgaac ataacataga  47760
cctatatgat tatacgtgga aattagctaa gaaaggtaat aaaccttatc ttacgcaggt  47820
agctattatg ctgaaatggg tatgtcaatc agcttcagcg aatacatatt atgacccgca  47880
gatttttcca aaaggaaagg ttccaatgtc tgtaatgatt gatgacatgc tatacggatg  47940
gtattatggc attaaaaact tctattatca taatactcgt gatggttccg gtactgatga  48000
ttacgaaata gaaactccaa aagctgaaga ttgttcatcc tgtaaattat gatataattt  48060
gactcacgga cgagtcacta tctattaact aagcggaaaa tttatgagca cagtttttaa  48120
tacaaatcca gttgatgttt taaaagaacc tatgttcttc ggttcaggtc ttggtattgc  48180
gcgttatgat attcaacgtc ataaagtttt tgaagattta accgaaaagc aattatcatt  48240
tttctggcgt cctgaagaag taaacttgat gatggatgct gcacaattta acaagcttcc  48300
tcagtatcag caagatattt ttactaataa cctgaagtat caatcacttc tagatagcat  48360
tcagggtcgt gcaccatctg ctgtacttat gtcattaatt tcagatccaa gccttgatac  48420
atgggttgct acatggactt ttagtgaaac tattcacagt cgttcatata ctcatatcat  48480
gcgaaatctt tatactgatc cgtcaaaggt atttgatgag attgtattag atgaagctat  48540
catgaaacgt gccgagtcca ttggtcgcta ttatgatgat gttctgatta aaacccgtga  48600
atgggaaaat gctaaagaat ttgtagaact agctaaagaa tctcctgatg ccgactttcg  48660
tttaaaccga gctattaaac aagaagccga agctaaacgt gctttaatga agtctcttta  48720
cctctgttta cacgttatta atgcattgga agctattcgt ttttatgtat ctttcgcgta  48780
aaatgcgcct ttaagcagta atgcttattg aaaactcctt taattgctgg aaaatccaga  48840
aatggaaaac tagcagccaa ggttttgctt gcacctttaa ttagtataat attataaata  48900
tgattatact tttaagagga tgcacaattg aattatagaa aaatttggat agatgctaac  48960
ggaccgatac ctaaagattc tgatggaaga acgtatgaaa tccatcataa agatggtaac  49020
cgtgaaaata atgatttaga taatttgatg tgtctttcta tacaggaaca ttatgatata  49080
catttagctc aaaaagatta ccaggcatgt cacgctataa agcttagaat gaaatattct  49140
cctgaagaaa tttctgaatt agcttctaaa gctgcaaaat ctagagaaat ccaggttttt  49200
aatatccctg aagtgagagc taaaaatatt gcctctatta aatctaagat agaaaacggt  49260
acatttcatc ttttaagtgg tgaaatacaa cgtaaatcta atttaaatcg ggttgcatta  49320
ggtatacata attttcaaca agctgagcat attacaaaag ttaaagaacg taatattgca  49380
gctataaaag aaggtactca tgcattttgc ggtggtaaaa tgcagtcaga aactcagtca  49440
aaacgagtaa atgacggttc acatcatttc ttatcagaag accataagaa aagaacatca  49500
gcaaaaacat tagaaatggt taagaacggg acccatcctg cacaaaaaga aatcacatgt  49560
gatttctgtg gtcacattgg taaaggtcct ggattttatc taaaacataa tgacagatgt  49620
aaattaaatc caaatagaat tcaattgaat tgtccatatt gtgataagaa agatttatca  49680
ccatcaacat ataaacgatg gcacggcgac aattgcaaaa caaggttcaa cgactagtct  49740
ttggacgtag ggtcaagcga ctcgaaatgg ggagaatccc tccgggattg tgatatagtc  49800
tggactgcat ggtaacatgc agcagttcat aagagaacgg gttgagaatt agcgagctca  49860
atcgaacata cggtactttt aacttccata agaacatgga aatcatggaa ggtaatgcca  49920
agattatgaa gttcattgca cgtgatgagc agcttcacct taaaggcacc caatatatta  49980
```

```
ttcgtcagct tcaatccggt actgatggtg atgaatgggt taaaattgct caagagtgtg  50040
aacaagaagc agttgatatt ttcatggaag ttaaccgtca agaaaaagac tgggcagttc  50100
atttatttaa agatggtgat gttcctggat taaatacaaa tagcatgtgg agctttattg  50160
attacttaac tgtatctcgt atgaaacagt gtggtcttcc atgcccaatt accgatgctc  50220
cggttaaaca tccgtatcct tggattcgtg aatatcttaa ttctgataat gttcaatccg  50280
cgccacaaga agtagaactg tcatcttacc ttgttgcaca gattgataat gatgttgatg  50340
ataaagttat gatgagtttt aaaaaatatt tttaaggagt gggccgcaag gcccatttta  50400
ttatgaaaga aattgcaaca gaatattcat ttattaaata tactgagcta gaattagacg  50460
acaatggaag tataaaacag ttatctattc caaacaagta taacgtaatt tatgctattg  50520
tcataaatga tgagcttgtt tatattggaa aaactaaaaa tttacgtaaa agaataaact  50580
attatagaac tgctattaac cgtaaagaca aaacgtctga ttctactaaa tctgcattaa  50640
ttcatgctgc gctaaaggaa ggaagcaaag ttgaatttta cgcccgccaa tgttttaatc  50700
tttctatgac aaatgagtta ggtacaatga caatcgcaac gattgaccta gaggagccac  50760
tattcattaa actgtttaac ccgccttgga atattcaaca caagaaaaaa tgatgcttcc  50820
acatggagtg tggtactata ttcaaaacac aaaagaggat acacaatgca agaacttttt  50880
aacaatttaa tggaactatg taaggactca cagcgtaagt ttttttactc ggatgatgta  50940
agtgcatctg gaagaactta cagaattttc tcatataatt acgcatctta ttctgattgg  51000
ttacttccag acgcattaga atgtcgtgga attatgtttg aaatggatgg agaaaaaccg  51060
gtaagaatcg cttctcgtcc tatggaaaag tttttttaact tgaatgaaaa tccattcacg  51120
atgaatatcg atttaaatga tgttgattac attctaacaa aagaagatgg gtctttggta  51180
tcaacatatt tagatggtga tgaaattctg ttcaaatcaa agggttcaat caaatccgaa  51240
caggctttaa tggctaatgg gattttgatg aatattaatc atcatcagtt gcgcgacaga  51300
cttaaaaaat tagccgaaga tggatttact gctaactttg aattcgttgc tccgacgaat  51360
agaatcgttc ttgcttatca agagatgaaa atcattttat tgaatattcg tgaaaatgaa  51420
acaggcgaat acatttcata tgatgacatt tataaagatg ctgctcttcg tccatatcta  51480
gttgaacgat acgaaattga tagtcctaaa tgggttgaag aagctaaaaa tgcagaaaac  51540
atcgaaggct atgttgctgt gatgaaagat ggttctcatt ttaaaattaa gtctgactgg  51600
tatgtatctc ttcatagtac aaaaagttcg ttagataatc cagaaaaaatt gtttaagact  51660
attattgatg gtgcatcaga cgatcttaaa gcaatgtatg ctgatgatga atactcatat  51720
agaaaaattg aagcatttga aacgacttat ctgaagtact tagaccgagc tctgttttta  51780
gttcttgact gtcacaataa gcattgcggt aaagatagaa agacttacgc gatggaagcg  51840
caaggcgttg ctaaaggagc tggaatggaa catctgttcg gtatcatcat gagcctctat  51900
caagggtatg atagtcaaga gaaggtcatg tgtgaaatcg aacagaattt tttgaaaaat  51960
tataaaaaat ttatcccaga aggatactaa gctgtttaca agtccctcgt gttgtgttac  52020
agtagtctta ctgacataac atgaggactt tatgatggat ttgcagctta ttactactga  52080
gatggtcgtt gaagcatacg gtgatactac agatgggatt tctgtattta aaggaaatcg  52140
tcgagttgga tatatcaccg atcttaagaa agatttagct aagcaagtca agcggaaaac  52200
gaccattaaa gaatatcgaa atcgtcgtct tgagcaagct cgtgatatgc ttcctgatgc  52260
ggttgaggag atgaaagtct ttttagaaaa tcagcttgcg aaatatgatt gtgatgtatt  52320
cattaatcag actcaaccta atgttcatat taacaactgt aaatgctata tcatcgttaa  52380
```

```
tcctttaacg ggaaaacatc gtcttggaat tagtaatcca aatcgtagcg catcagatat  52440
ggcagaagat gttgaggcat gctttaaaat ttctaaatct ccggctgaac atcatatttt  52500
aattaacggt ctttctcaag acgatattat agaggttatt aaaactttat gcaattaagt  52560
aatacgacag caggtttgtt attaattgta attgcattgg gcggaacttc tttaatttta  52620
aaaagtaaaa ttgaaagatt agaaacgtct gttgtagaaa ttacaaaaac ggccaatgaa  52680
aacgctttag cattaaatga tttaaaaatt caatataatt atattgatgc gatgaataat  52740
aaaaatcgtg aggcaattgc tgctattgag cgtgaaaatg aaaaactgcg caaagacgca  52800
aagaaggcgg atgtggtggc tcataagcca ggattggttg aaaaacaaat caacaactcc  52860
tttaataagt tcgcagaaga catccaggac ctttctaaat gattaaacta tcagcagtaa  52920
tattatctat tggtcttcta gttggttgtt cgacaaagcc tctagaagta aagaaagaaa  52980
cagttcatcc taattggcct gtgcagataa agtcatatga tgaagctaaa ctatcctggc  53040
aagttaaagt tatcgatggt aaagcttggg tcggtatgcc atttgaagat tcccaggaat  53100
ttcgtatttg gcttaatgat gtaaaacgat atgtgcatga ccagaaaact atgatatgtt  53160
attatcgtca agagttaaaa gaggataaat gtaaatgatt tcatggcatc aatttgaaca  53220
tctcaaaggg ttgatttatg aatccgagat ggctgcaatg atttacggac gccagattca  53280
acgattagaa tctttgcctc caactaatga tgttttatta gctcaatctc gggctaatct  53340
taaaaatgaa tatcaaaata agtggggtaa agcatctaaa gacctgcatg attatattca  53400
atcattagtt gagaaaaata aatgaaaact ctgctagaac gttatattga atgctcagat  53460
cgttacattg atgcatgcca tggtgcagta tacatggatt tggaccgcgg aatagtatta  53520
aatgatgaag accctgcgaa agctttagat gatgctggta aagctctacg aaaagaagca  53580
aaagctcgtg gacttgatat gtatcagctt aaaaatcaca tgataaaatt tatttcatct  53640
aatgttcaga gcaaatcggt gaatcaatta acagctgaat tatataaaga gcggcgtgag  53700
cataatattc gtattcttga agttttctta ggaattaaat gatgaaaaag attattttga  53760
ctgttggatg tcctggttca ggtaagagca cttgggctcg tgaatttatt gctaaaaatc  53820
ctgggtttta taatatcaat cgtgatgatt atcgtcaatc catcatgggt catgaagaac  53880
gtgacgagta taagtatacc aaaaagaaag aaggtatcgt aactggtatg caatttgata  53940
cagctaaaag tattctgtac ggcggtgatt ctgttaaggg agtaatcatt tcagatacta  54000
acctgaatcc cgaacgtcgc ctggcatggg aaacttttgc caaagaatac ggctggaaag  54060
ttgaatataa agtgtttgat gttccttgga ctgaattggt taaacgtaac tcaaaacgtg  54120
gaactaaagc agtaccgatt gatgttttac gctcaatgta taaaagcatg cgagagtatc  54180
tcggtcttcc ggtatacaaa gggactcctg gtaaaccaaa agcagttatt tttgatgttg  54240
atggcacatt agcaaaaatg aatggtcgcg gtccttatga ccttgaaaaa tgtgatactg  54300
atgttgtcaa tcctatggtt attgaactag ctaagatgta cgataagcaa ggatattaca  54360
tcgtagtcgt ttcaggccgt gaaagtggaa ccgaagaaga cccaacgaaa tattatcgta  54420
tgacccgtaa atgggttgag gatattgctg gcgttccatt agttatgcaa tgtcaacgcg  54480
aacaaggtga tacccgtaaa gatgatgtag ttaaagaaga aattttctgg aaacacatcg  54540
caccgcattt tgatgtgaaa ttagctattg atgaccgtaa ccaagtcgtt gagatgtggc  54600
gtcgtatcgg tgttgaatgc tggcaagttg cttatggaga tttttaatgg cgtggcatca  54660
tgaaacttgg tctattgtta ttgtaaatag tggtttagtt ggtactagta atgggcaatt  54720
```

```
ttgtgtattc actagtgaaa tcagagcttg ggaggaatgc cttaaattaa gagaaaagaa  54780
tcctgatgtt gaactaacag taaagaaaac taaactgcct ttaccatgga aaacttatga  54840
ataacataga aaagatttat caactttgcg ataaaattga aaaagaaaag aaatatctat  54900
tttgtttatg gcctattgtt gatggaagaa tagacttaga tattcttgat tatgaaacag  54960
aagacatagt agatggttca acttttgata atgcgttgga tgttattaat tggcttgaag  55020
aaaattatgt gaggtaaata tgtttccgac ttattctaaa atcgtagaaa tagtgtttag  55080
ccaaattatc gctaataata tgtttgaaaa gcttgataac gcagctgagc ttcgaattca  55140
tgctcaagtg actcatgtat tgaacacttt gcttccagac caggtggatt ctattgcaat  55200
tacgctgtat ccgggttccg cgcatatcat tgtcgtattt ggtcttgatg ctgagctagt  55260
catcaaaggc gatattcgct ttgaatcaca gacatcagaa ttcaaggcaa tttaatagtt  55320
tactttttgg tagagttgtg atattatagc tctaccaaaa caaatgagga aaacaaaatg  55380
ctaagtgaaa aaccaattac tgttaaagaa ttccaagaaa aagttaaact atttgcacag  55440
gaattggtaa ataaggtttc tgaacgattt ccagaaacat cggttcgtgt tattaccgaa  55500
actcctcgtt cagtattagt aattgtgaat ccaggtgatg gcgatcaaat atcgcatctt  55560
aaactggatt ttgatggatt agttgaagca caaagggtgt atggcgtact atgatgaatt  55620
taactgatat aattgataat tgtcttgaaa atgatactgg cgatcataga gcgcttgatt  55680
ctgaaacagc acagttcatt agaataactt taatgaacga tactctggtg aatagtattc  55740
atccttctgt gtatgatgct attattgtga cgaagtatcc agttgagctt cacaaaaaga  55800
tggctggtgc aattttcatt gataagaaaa accgctttaa agatgggcag aatataatta  55860
gttctgttat taaaagtata actaaacttc gtcacgaaat ttatcgtgtt gaaactgcta  55920
aatctgctta tctggtgatt atgaaatgaa agcgagtaca gtacttcaaa ttgcatattt  55980
agtatcacaa gaatcaaaat gttgctcctg gaaggtagga gcagtaattg aaaagaatgg  56040
acgtattatt tctactgggt ataatggttc gcctgcaggt ggtgtgaatt gctgtgatta  56100
tgctgctgag caaggttggt tgctgaataa gcttaaacat actatcattc aaggtcataa  56160
gcccgaatgt gtatcatttg gttcaactga tcgttttgtc ttagcgaaag aacatcgtag  56220
tgctcactct gaatggtcgt ctaaaaatga aattcatgct gaactaaatg caattttgtt  56280
tgctgcacga aacggttctt caattgaagg tgctactatg tatgtaacac tttctccttg  56340
tccggattgt gcaaaagcga tagctcaatc tggtattaaa aagctggttt attgtgaaac  56400
atatgataaa aataaacctg gctgggatga tattctgcga aatgcaggta ttgaagtgtt  56460
taatgttcct aagaaaaact tgaataagtt aaactgggaa aatatcaacg aattctgtgg  56520
tgaataatga aatttcgttt ggtacaactc acagcaatta gttcttattc caacgagaac  56580
atttcatttg ctgtagagta taagaagtat tttttctcta aatggaagca gtattataag  56640
tcaaactggg tttgtattga taggccgtat agttggaaat ctgatttaga aaaatgccaa  56700
aagttgcttt ccactcttaa agaacgtgga acaactcata ttaaaactgt aataggtaaa  56760
taaatgaaat tgacgactga acaaaaagta gcaattcgtg aaattttgaa aactaaattg  56820
tccatgggta tttcaaacgt agtttttgaa aagtctgatg gtactattcg tactatgaaa  56880
ggtactcgtg atgccgattt tatgccaacc atgcaaactg gtaaattgac tgaatctgcc  56940
cggaaagaat ctactgatat gattccagta tttgatgttg agcttggcga gtggcgaggt  57000
ttttctatta acaaattgat ttccgttaat ggtatgaaag ttgagcattt gcttcaattt  57060
attggtaaat aaatgcttta agaattattt gttattatta attcatctgt taacaaaaag  57120
```

```
gaaaaacgat gtctgaagta caacagctac caattcgtgc tgtcggtgaa tatgttattt  57180
tagtttctga acctgcacaa gccggtgatg aagaagttac agaatcagga cttattatcg  57240
gtaaacgtgt tcaaggtgaa gttcctgaac tgtgtgtagt tcactctgtt ggtcctgatg  57300
ttcctgaagg tttctgcgaa gttggtgatt tgacttctct tccagttggt caaattcgaa  57360
acgttccgca tccttttgta gctctgggtc ttaagcagcc aaaagaaatt aagcaaaaat  57420
tcgttacctg tcactataaa gctattccgt gtctttataa gtgatataaa taataatacg  57480
aattgggtgt cggaataata agttaaccga acaattctat gtggtagtct acaactgaga  57540
gatctgtcga aagaagatga aattcagaag aacgtgacta ccgagtttta atctctaacg  57600
agaattttta aatgattaaa caattacaac acgctcttga actgcaacga aacgcatgga  57660
ataatggtca cgaaaactat ggcgcatcta ttgatgttga agccgaagct cttgaaatcc  57720
tgcgttattt caaacatctg aatcctgctc aaactgcatt agctgctgag cttcaggaaa  57780
aagatgaact taagtatgct aagcctttgg cttctgctgc acgaaaagca gttcgtcact  57840
ttgtggtaac actgaagtaa ttatgccgtg gttggtagtt atcctggcgt taacgatgta  57900
aaactaccaa atttcagtta gtatcgagga gccgtcgaac tgtctgatta atgatttgcg  57960
aatcattata gttttaagac cccggcagtt ttacggtgta cctcttgaat gttattctta  58020
tagcggcaag tgcatgctac cccgaggtga tggccaatcg ggagtacgcc tcaaggccta  58080
tatatccatc agtatatatc ttatcctcga gaaatcgaac ccggaacctt taagctaacg  58140
gtgtgcaaca gataagagct ataaggtatg atgacgggtt tatggttatc ctggtcgtta  58200
aatatccaaa aacctatgtt ccccttgagg gcttgcgcag gcaatgccaa taagtcctgc  58260
attttcattt aaaagagaat ttataatggc aaaacaagct aaagcaaaga aagcagttga  58320
aaagaaagtt ggtgattcta aacgcgctgg ttacaagcgt gggtcgaact ctcgtatcaa  58380
tcaaactgtt gagaagatca tgcgccgagc acgtgcggtt cttcgagatg atgcttctcg  58440
ttttggtaag cagaaagcat aagttgagga ctccttcggg agtccttttt tattttccaa  58500
agattgcata aagttgttta cagtatggtt cctttgtgat agtattatct tacacaaaca  58560
aaggagaata aaatgaaaac gattaatctg aacgctgcag ttaaaactaa atgcttcaat  58620
ggtaaatatg atgaaactat gtggttctta atggcagttg aaggtgatat tattgaagta  58680
gaaacaacag aaggtatggg aacagatttc acctttacaa ttcaagttca taatttcttt  58740
actggttgga tttatgaatt gaatacagta atcgttggaa aaattgaaca aaatgaatta  58800
ggtgaatggt attatgttac agctcgccaa cgtgccgaac gcttaattga gaagatgaaa  58860
aaagttggta aacttgatat gcagcattgg aaagtagtaa aataattgtt tactttggta  58920
caggatatga tattatatac ctgtaccgca attaaacatc ttggagaata aaatgaacta  58980
catcaacttt gaacgtaaat atgtttctaa tggtattgca ggttctattg atactatttg  59040
cctttggaaa catcaaaatg gatcagtatg cgaaattgaa cagtatatga ctcctaacta  59100
cgtttatatg cgatttgaaa acggtatcac ggtttcaatc acaatggaag gttccaactt  59160
caaaatcgct ctggatgatg atttccgtga acgcgattta gggactcatc cttgctggaa  59220
tggcgttaat cgcaagcttt tggttaaaac ttggattcgt catattctga gtaacagagc  59280
taaacctgag catcttgaag caatctttga tgtagttctt aacgaatttg atatttaaaa  59340
taaatgaggg gctttggccc cttactgagg aaaatgttat gtttatgact acttattttg  59400
atacccgtaa aaacttctgc gaagtagttt tctcaaaggc gcctaaagac cttcctgcac  59460
```

```
atttgcaacc taccagtgaa tcgattaaaa actacgttaa tgtagtctgc cctttagagt  59520
tccgtactgt aaatgggcgc gatactttag ctatcactaa actcaatcgc gaaattgaca  59580
ttgatccctc aattgcacgt gaaattaata gttctgatat taatggcggt aatgttaaat  59640
cgcacggttt tcagatgagg ttttaatgaa attcttttta ggtcaaactg ttgaattaaa  59700
gggagttggt atacctggat taatttctaa ggttctacct ccgtttaaat ggagtggtat  59760
tcaaataaaa gaggcttata ttgtttcttg ggtagatgga aatgaagacc ttcgtgtggg  59820
cgatgaatta tctcctatct acggattaaa ggaattagta tgaatataat taataagatt  59880
tttggaattc agtacattaa ggtcacatat aaagtaacag ataaaaatcc gtatactgat  59940
gaacacgaag aaccgcaagt taagtctatt atattagaaa aaggcagtga ctggccagtt  60000
gaatttcgtc taccaaacta tggtcattgg gctgatgttg aaattataag cattgaaaat  60060
gtctgagtta gagattagaa gcaattttag gtggccatca tgcgcattaa gtaatttcgc  60120
ccaatggcct ttcgttatgg atggcattca atttggaggt cttgaaggat tcctccaagg  60180
gtgcaaggtg aaaaatgttg aacaacaacg tcgtatattt gggttatccg ggcttgcagc  60240
ccaacaagct ggaaggtctt atgcaagagc tcaggaccgt gggaccctct tctggcttgg  60300
agttccattt tcaagatact ccccggcgtg gaaagaatta tacacaaatg catattttga  60360
agcagcgatc caaaacaagg gcttccgtga tgcattacaa gcctcgaaag gaaaagtttt  60420
gaagcacagc atggctagtg gtctaacaaa agatgatata atactaaccg aagctgaatt  60480
tattgatgtg ttaaacctat taagagactc tctatgaagc ctactatttt aactgatatt  60540
gatggagtat gtttaagctg gcaatcaggc cttccttatt ttgctcagaa atataatctt  60600
ccgttagaac atattttaaa aatgatccag gatgagaaat ttatttctcc tggtaaacta  60660
tttaattgcg atgaagaact tggcgttaag ctaattgaaa aatacaatcg ttcggatttt  60720
attcgatact tgtctccata taaagatgcc ctgtgtgtaa ttaacaaatt aaaagaagat  60780
tataattttg tagctgttac agcattgggt gattctattg acgctctgct gaatcgtcaa  60840
tttaatttga atgctctttt tcctggtgcc ttctcagaag tactgatgtg tggtcatgat  60900
tcttcaaaag aagagttgtt caaaaaggca aaagaaaaat ataacgtaat ttgttatatt  60960
gacgatctcg ctcaccattg cgatcatgcg agtgaaatat taaatgttcc tgtttattgg  61020
atggctcgag gggaacgtga cagtattcca aaaactgcac agcgagttta tacatggaat  61080
gatgtagaaa ataagctttt ttcaccaaag gaaaataaag aaagttttga tagtgaaaaa  61140
gctataaaag atgtaattga gaagatgatc aaaaacgatt cttttcgttg gaacactact  61200
tggagaactc ctggatttaa tccttataat ccatatcatc catattatac acactcacat  61260
cagatgcatc cattccatac gtggagttat attaagcctg gcgacgcagg gtattttaat  61320
agacttacta gtggtagtgg tgataatatt ttccaaggag cattctaatg tttgttgttc  61380
acactattta tgaaaatgaa ggtaatacta cacgtgatta cggtcacgta aatcaatttt  61440
ttagatgcaa tccagaattc cgagctcaaa aagacgaacg aatttttaaa aaatgtgtag  61500
agcaaggttt catttacgtc aagcactgga tgcaaggaaa taaagttaga accacgtacc  61560
acaggtcttt gactgagctt aatgatgaat tgatttataa tagagctgta aaccaaactc  61620
taaaggatga acaatgattc ttaaaattct gaacgaaata gcatctattg gttcaactaa  61680
gcagaagcaa gcaattcttg aaaagaataa agataatgaa ttgcttaaac gagtatatcg  61740
tctgacttat tctcgtgggt tacagtatta tatcaagaaa tggcctaaac ctggtattgc  61800
tacccagagt tttggaatgc tgactattac cgatatgctt gacttcattg aattcacgtt  61860
```

```
agctactcga aaattgactg gaaatgcggc aattgaggaa ttaactggat atattactga  61920
cggtaaaaaa gatgatgttg aagttttgcg tcgggtgatg atgcgagacc ttgaatgcgg  61980
tgcttcagta tctattgcaa acaaagtttg gccaggttta attcctgaac aacctcaaat  62040
gcttgcaagt tcttatgatg aaaaaggcat taataagaat atcaaatttc cagcctttgc  62100
ccagttaaaa gctgatggag ctcggtgttt tgctgaagtt agaggtgatg aattagatga  62160
tgttcgtctt ttatcacgag ctggtaatga atatctagga ttagatcttc ttaaggaaga  62220
gttaatcaaa atgactgcag aagctcgcca gattcatcca gaaggtgtgt taattgatgg  62280
cgaattggta taccatgagc aagttgaaaa ggagccagaa ggcctagatt ttctttttga  62340
tgcttatcct gaaattagta aagctaaaga attcgccgaa gtagctgaat cacgtactgc  62400
atctaatggc atcgccaata aatctttaaa gggaactatt tcagaaaaag aagcccaatg  62460
tatgaagttt caggtctggg attatgttcc gttggtagaa atatacggtc ttccggcgtt  62520
tcgtttaaaa tatgatgtac gtttttctaa actagaacaa atggcatcag gatatgataa  62580
agtaatttta attgaaaacc aagtagtaaa taacctagat gaagctaagg taatttataa  62640
aaaatatatt gaccaaggtc ttgaaggtat tattctcaaa aataccgatg gattgtggga  62700
aaatgctcgt tcaaaaaatc tctataaatt taaagaagta attgatgttg atttaaaaat  62760
tgtaggaatt tatcctcacc gtaaagaccc tactaaagcg ggtggattta ttcttgaatc  62820
agagtgtgga aaaattaaag taaatgcagg ttcaggctta aaagataaag ctggcgtaaa  62880
atcacatgaa cttgaccgta ctcgcattat ggaaaaccaa aattattata ttggaaaaat  62940
tctagagtgc gaatgcaatg gttggttaaa atctgatggc cgcactgatt acgttaaatt  63000
atttcttccg attgcgattc gtttacgtga agataaaact aaagctaata catttgagga  63060
tgtatttggt ggttttcatg aggtaactgg tctatgaaag cttacttaga aacaattgtc  63120
gtggctcaaa aagaaggtgg agatgtttct acttctgtat cacaaatcgt tctcgaattt  63180
gtagatgcat atgcttataa taaatttaca gaaacatttg atgcctacga aaaaggtcca  63240
aagtttgaaa tatatcgtac tctcttacca ctagattact aaaggccttc gggcctttaa  63300
ttttataaat agaataaaca ctagagagga tatgatggaa ctaattacag aattatttga  63360
cgaagatact actcttccga ttacaaactt aaatccaaag aagaaaatac cgcaaatttt  63420
ttcagttcat gttgatgacg caattgaaca accaggcttt cgtttatgta cctatacatc  63480
tggaggtgat actaatcgtg atttaaagat gggcgataaa atgatgcata ttgttccttt  63540
tacattaacc gctaaaggtt caattgctaa attgaaaggt cttggtccaa gcccaattaa  63600
ttatatcaat tcggttttta ctgttgcaat gcaaacaatg cgtcagtata aaattgatgc  63660
ctgcatgctt cgtattctta agtctaaaac cgccggtcaa gctcgacaaa ttcaagttat  63720
tgctgataga cttatccgta gtcgttcagg tggcagatac gtccttctta aggaactctg  63780
ggattatgat aaaaagtatg catatattct tatacatcgc aaaaatgtat cactagaaga  63840
cattccaggg gttccggaaa ttagtaccga gctctttact aaagttgaat cgaaggtcgg  63900
tgatgtttat atcaataaag atactggagc tcaagtaact aaaaatgagg caattgcagc  63960
atctattgca caagaaaatg ataaacgttc tgatcaagct gtaatcgtta aagttaaaat  64020
ttcccgtaga gcaattgcac aaagtcagtc gttggaatct tctagatttg aaacaccgat  64080
gtttcaaaaa tttgaggctt cagcggcaga attaaataaa ccagcggacg ctcctttaat  64140
ttctgattct aatgaattaa cggtaatttc tacttcagga tttgcactag agaatgctct  64200
```

```
tagcagtgtt acagctggga tggcattcag agaagcttct ataattcctg aagataaaga  64260
atccattatt aatgcagaaa taaaaaataa agctttagaa aaattacgaa aagaatctat  64320
tacttcaata aaaactttag aaactattgc ttctatcgtc gatgatactt tagaaaaata  64380
taaaggtgct tggtttgaaa gaaatattaa cagacattcg catttaaacc aagatgctgc  64440
aaatgagtta gtacaaaatt cttggaatgc aataaaaaca aagattattc gaagagaatt  64500
acgtggatat gctcttaccg ctggatggtc attacatcct atagtcgaaa ataaagattc  64560
atctaaatac acaccagcgc aaaaacgcgg aattcgtgaa tatgtaggtt caggatatgt  64620
agacatgaat aatgctcttt tgggattata taatccagat gagcgtacaa gtattttaac  64680
agcacctgaa atagaacaag ccattgataa tttagattca gcctttaaaa atggtgaacg  64740
attaccaaaa ggtattactt tgtatcgttc acaacgaatg ttaccttcaa tatacgaagc  64800
aatggtaaaa aatcgagttt tttattttag aaactttgtg tcaacatcat tatatccaaa  64860
tatttttggt acttggatga ctgattcatc tgtgggtgtt ttaccagacg aaaagcgttt  64920
aagtgtttct attgataaaa ctgatgaagg acttgtaaat tctagcgata atttagttgg  64980
aattggatgg gttattactg gggctgataa ggtcaatgtt gttttacccg gtggaagttt  65040
agcgccttca aatgaaatgg aagtcatttt gccacgtgga ttaatggtca aagttaataa  65100
aataactgat gcatcttaca acgatggaac agttagaact aacaacaagc ttattcaagc  65160
tgaagttatg accacagaag aactcaccga atcggtaatt tatgacggtg accgtttaat  65220
ggaaactggt gaattggtta caatgacagg tgatatagaa gatagagttg actttgcatc  65280
atttgtttca tcaaatgtta aacagaaagt agaatcatct cttggaatta ttgcgtcttg  65340
catagatatt gcaaacatgc cttacaagtt cgttcaagga taaatcatgg aacttattac  65400
agaattattt gacggcgctt cggcgccggt tgttaactta aatcctaagc ataaaatacc  65460
acaaattttt gctattcaag ccggcgaaga aagcgtgctt cctggattta gattttgtac  65520
atacacctct ggcggtgata cgaataaaac gttaagccgg gcgataaaat gatgcatatc  65580
gtaatgatag gtgttaatga gaaactatca ttagttaagc ttaaaaactt gggtggaaat  65640
ccaattggtg tcattaatgc tgtttttgat actgctcttc aaacaatgaa acagtataaa  65700
atcgacgcat gcctattacg cgtactaaaa agttcaaaat gtagtttaca agtccctcgt  65760
gttgtgttac agtagtctta ctgacataac atgaggaaca caaaatgaaa tcttctttac  65820
gctttttagg tcaagaactt gtagttgaag gcgttattcc tgctgataat gcttttaatg  65880
aagcagttta tgatgaattt atcaaaattt tcggaacaga taaaaagttt ggaatttttc  65940
cttctgaaaa tttttcaaag ccagaacaga ctgaaagtat ttttcagggt gtagtaacag  66000
gtaaatttga gtcagaagct ccggtaaaaa ttgaagttta tattgaagac agtttagttg  66060
cttcagttgc tgctttcatt tcattccgta aataaaaata tggggaccga aaggtcccca  66120
ttgttatatt actcctaata ttttactttg cgaattgaca atccctgcca tagtattaat  66180
gtttgaaatg cttcccgcag ttcctcctaa tctactaagt cgtgaaagcg aattagataa  66240
tccagtaacg cctccgctat ttccgagaac gctttgaatg ccatttatag cagcagattc  66300
aagccactca agcgcagctt gtctatcaac cgacccagcc tgcatgactc tatatgcaaa  66360
agtaacatca aatgtagtta tttggttatc tccatcatat gataactcag gagcgctcac  66420
tgacactgga atgcatccgg tgaacatcac ggcagtatga ggtaatccat tacgagcatg  66480
aagattaacc tgaatatctg cctcgacatc ttgcggcaaa gcacgcagtc cagttactgg  66540
gtcttgaaca gcgttaaccc agtcttgcat cgcacgatag ttacaagctt ctgaatccat  66600
```

```
tctaaatgaa ataaccaaag ggtctaattc tctcccagtt atacgaatat taggagaatt  66660
atagttccag tcagtttcat aggataatct attctctggc atttttacag agtatatcat  66720
caatccagat gagttatatg ccatgttaaa gaagtcaatt aaatatgtac caactgtaaa  66780
tgagcccaat aaactttgaa ctgtacgttg actcatggca ccaataagat atttactaac  66840
tcctgatttt cttatcagtt tttgtgtgcc agcagtaatt agcgtggtaa ttccctgatt  66900
aatatcgcct tgagtcaatc ctaaccaatc tgaatttaaa cccaagttat tataagaaaa  66960
gttgctaatt gaacttatca acgaagagct tttagttgat ggagttgtcg caaaaacgca  67020
gctaaacata ttattacgtt ggaaatctgc gtttattgct tgattattaa attcctctaa  67080
agaatacatt aaaaagtccc cgcatataaa gaagcacggt ttaacgtgat aatttctctc  67140
atagtaatct cgagagtaaa tgtactaggg aggtttggag caatagctaa tccgttaaag  67200
ttaccattag gtgttttatc aaatctgata ctctgtattt ggcatgggcc aaatatttcc  67260
gtttttccat caaacttaga tgttgcacca aagtttttca ccatccaaat tgtcgggttt  67320
gaaactacta gaacgttagt taaactcgat gtcattttct caaatagtgt tttattttta  67380
gctgcgtctt ccggagataa aggttcaatt aatgtagaac gataccaatc atctaaatat  67440
ccctttattt cagcagcata ttgagattta cccgtttcac cataagaaaa atagttaaaa  67500
tattgataga tattaataat agccattaaa tcttctgtgg aacgtggagt caaatcccat  67560
gtaaacactt tagttctatt ctcagcacca ccatacatac ttctggctgt cgtataaatc  67620
tgttcattat tatcagccat tataccttgt gttatacttt ccagtgctcc aaatactgca  67680
gttgaagcaa tattacttag cacaccagta gcagttcctc cgcctctact gataagactt  67740
tcttgaacat cattaaatct atgtgatgat gtatcaacgt cagatttaga tctcggtaaa  67800
agaatgtttg ccacaggagc tttacttatt gttcctgaat tattatctga tattaatcca  67860
tttgacagtt ttgatactgt actactaata gtgtttctag ctgtacttaa aatactcgaa  67920
gatgaagaag agtagttaga tctcatcgat ctaagacttc cagaatccct agatgacata  67980
ttgtatgcag taaataataa tccattctta tatagatctg ttacctggaa gtcccctgta  68040
gtgtcattac cactagcacg cccagttgga aactgggcag tgtatgtttt agttgctact  68100
tctgatttag tactctgtcc ggctgaaatt ttctcaccgg actttttaat taaatcagca  68160
gttatttctt taacaattgc catattattc cttaattaac tccagtcgcg ccaaatacac  68220
caggagcagt cgtgctcgtt acgggtgtca tattatgaac gacagtattt ttcttaataa  68280
cattattagt attattgatc gaaggagatg cttgttgaac aggagcttgc tgtgctttgt  68340
tcttttctat tacctggact tgttttgctt ctggcgattt agcagaagtt tcaggtttgg  68400
cattaggctg atttttcttg agctcttgat aagtagcatc aattttagaa aatctagcag  68460
caagttcttt tttaactgcc ggtgaattat ttaaatccgg gtcatccatc cgtttttttaa  68520
ggtcttcata ggcagcttca actgatttaa ctgttgagtc tttactcata tcagctgaat  68580
cggcatattt ttcaaaacga atcatcgcgg cgcgtgcttc attagctttc attaaagcat  68640
tttttctttc ttccggtgaa agttgcttta atttttcttc ttctgctgca cgttcttcat  68700
ctgttgtcaa tgattcttta ttatcaacac cacgaatcca gttagatgca cgagttttcc  68760
agttcgcaat tttgtctagt ccttctgcta tcggaccaag gtctccattc attcgtttat  68820
cttgataatt cgcaactttt tcctggtctt ctttattgag agatgctcca gtagaatttt  68880
ggaaattttc tagtgctctt ccttctactt catcagcagt atccttcatt ccaggaatga  68940
```

```
ctcgaagaat tgcagcagat aatttagcca ttccaagctg aataagttct cctaaattat  69000
aaagaacctt tccaagccct tctacaatag ctaccgtcaa accgccccaa tctccctctt  69060
cccagaattt tttaatttca tcgatagaac taaagatgct ctgtaataaa ggaccccatg  69120
ttccggtttc gctagagaat ttagtaaagt ctgtactaaa taaatcccaa gcctgcgaaa  69180
atttatctga ccaatattta aagtgaacca tcagcagatc tattccaaca acaacagcca  69240
atatcattgc agtcatttta gcagcttcaa tagcagcact gacggtatac ttaaataaca  69300
tgctcgatat tttatcagta attgaaatgg acttcttaaa tccaaaatca acagtcttcg  69360
ttaatttatc taaagcttga gataatttta agttaaatgc gtcttttttc tgtttttctt  69420
ctggcgattc ttgtttgggc tcaactggct gaggggtagg gaaaaaatca gcatcaggat  69480
cattattaac tgcttcagga gctggtaata aaggacccac agattcagct gtatcgtcct  69540
caacaacttt aacaggaata gcgctttcaa ctgtagctaa actagttcca gtttgttgaa  69600
ttccagctgt ctggattttt tgctctagta aactcgttaa tttatctaat ttacttccga  69660
gtgattcacc gatttcttta ttaatattgt tgccaatttc gacagtttca gcaattaact  69720
cagaaccagc agtagtatca ctcactgcgt tttctacgtt gtcaattgct ccaattattt  69780
cattcgattt ttcttcgaca gtttgagcaa ttaattcaga agcagcttga gcatcatcca  69840
atttcgtaga tatatcgtta agtccagata aagtgttgga agcggattta gccgcttcct  69900
gtgttggttt attatctgaa ataacttttc tacgcatcgt ttgcatttct tgtggctttt  69960
tcattcaaat aatccaataa tattaccaat tccagttatt ggaccattag ggccaggaat  70020
tgctaaagtt gtaaaaatat catttgccca ttttaaaacg aatgctggca tctcaagaaa  70080
attaatttct ttaacttcat cattgacctt aagcaagcat ttggataaca tatcgctcac  70140
tgttaaaaat tgttcaaatt ttccaggagg tctaaaataa aatatatttc cttggtattg  70200
aaattctaat ctttggcata cataaacatc attaatgtca taagtatagc catctatttc  70260
tttgcgagat ttaatctttc cattaaattc caataaatga atagaaacga aatcaacttc  70320
tgccggtgat aaattcggac aaatagaatc gatcaaaagt tttaaatttt catcaggacc  70380
tttaacatcc tttaaaatgt tataatgttt aagacccatt ttaggaatag aaacttcttt  70440
attgcttatt ggaagaacta ctttcttcag tggtagtatc agatttaaat tcatttttaa  70500
ccttaactgg gtctattgtt tccagtttcg ttgcattagt gaacatatat agatgagtta  70560
ttgaattatt attggataat tcatggataa cttcatcaac gtaaaattct gttttaaatt  70620
ggtttttact atcattaaaa ataattttaa cgccaggagt caagttaaaa ttaccgacag  70680
tagaacattt agcatagcca tcgtattgcg ccatagtttg aagacgaata gcttcttcat  70740
atccattcct ataagtcatt tcagaataag cacctgacct tgacactaca atagagtttt  70800
cgccctttcc tgtagtaatc attggcaatg aagaatctaa aaatgaatgc gcatagatag  70860
tagcgttttt cattgggtca cgtttgtgag gattcgattt agtcaaccaa acgaaatcat  70920
atgctaatgg atattttaat tcttggatga attgacctat taaagatggc tcaccgacaa  70980
tcattggata tggttcttga tttatcatca tatcatagtc catcatgtta actcccatga  71040
tgtcttgcca tacaaataca aatttgtcac ttcctacagc tagagcaact tctctgacat  71100
acgacaaata gttttcaaat gtgctagtcc atggaatatc aggaacataa gcatttatag  71160
catttattgc tggagttaat aatgtgcgat cctgataaat gacaccaagc atttccttta  71220
tagattcacc tacatcagag aaaaacggtc tgccaaattt aagattttct atggaatgaa  71280
tagttcccaa ttcaatagca atgatgttat cgccctttga atctacagat acagaaaaat  71340
```

gcttacatcc ataaattcgt gttttaacat tattaatatc gtttgcatta gctacagaaa 71400
tctgaattat ttcatttcca tccatttttg tatggatatt tttagaatca taaaactgca 71460
acattccttc atttcggcca taaagagaat cccgcatagt taatgtggta atagtagcag 71520
ctaattcaac aaatctatta ttactccaag cgtcgtagct atcaaataat ttaacgctga 71580
gatttggata tccagggcgt tgcaacatac tcattattgt ttatccttct caatcagttt 71640
taatacgaat ccgcgctcag caggaatcat tttcattatt gaatttaagc tataattact 71700
ttttacgagt gtgtgattaa tttgataaaa agtaaatatt tcatctgggt taactaatag 71760
cttaaacaca tctactatat cggtgtattt tttaatgtac ttattacagc atgacatatg 71820
tagagttaaa ttaataggat tcattgcatc gagaattttt tctagtgttt ctatctcgat 71880
ggcgtcaact agttctattt gacttgattc actaatttcc ttccaatcat accaaatttc 71940
atctacttga acagaatgaa tattttcagt aatcatcttt gctttatttt cataaaactc 72000
agaaggaaac tttaatttaa ttttaacatt agctacatca aaaacaggtt cctttaattc 72060
tttttgatat atttcaaatg gaactgtctt ttctttttta cattttggac atacgaatgt 72120
gactggtact ttagttttac ctattgaccc tacaaatacc tgcaaaaata taaatggttg 72180
ccaagtcttc ggatagtctc caaaataatc atcaattaaa tcagtaatta tttctttttg 72240
ttcttgtggt gaccgatgtt ctatatcgtt tcgaactaac aaaaaatctc gataatcttc 72300
taccgtaaat ggtttaaaac gatgaacacc atctggtaat ttacaacgaa taatgtttgc 72360
catagatgct ccttttattc tatttataaa tatgataaat aaaggagcta aatatgtatg 72420
aatacaaatt tgacgtgaga gttggttcta aaataatcaa ctgtcgcgca tttactctta 72480
aagaatatct agaacttatt actgctaaaa agaacggttc agtagaagag atcgttaaaa 72540
agctaatcaa agactgtaca aatgcaaaag atttaaaccg ccaagaatca gaactcttgt 72600
tgattcattt atgggcacat tctcttggag aagttaatca tgaaaactcc tggaagtgca 72660
cctgtggaac tgaaatacca acccatataa atctattaca tacacagata gatgcaccag 72720
aagacctctg gtatacactg ggtgacatta aaattaagtt ccattaccct aaaatttttg 72780
atgataaaaa tatagcccac atgatagtat catgcataga aacgattcat gctaacgggg 72840
aaagcattcc agttgaagac ttaaatgaaa aagagttgga agatttatat tctatcatca 72900
cagagtcaga tattgtagct ataaaagata tgcttttaaa gcctactgtt tatttggctg 72960
ttccaattaa gtgtccagag tgtggaaaaa ctcacgctca tgtaataaga ggactcaaag 73020
aattctttga gctattgtaa tggcaaatat taataagctt tattctgaca ttgacccaga 73080
aatgaaaatg gattgggaca aagacgtttc cagatccctt ggattaaggt caattaaaaa 73140 tagccttta ggaattatta caactagaaa agggtcaagg ccatttgacc cagaatttgg 73200
atgcgattta tctgatcagc tttttgagaa tatgactcct cttactgctg atactgttga 73260
gcgtaacatt gaaagcgcag taagaaacta cgagccacgt attgataaat tagcagttaa 73320
tgtaatacca gtttatgatg attatactct gatagtagaa atacgctttt cggtcatcga 73380
taaccctgat gatattgagc agataaaact gcaactggct tccagtaata gagtataatg 73440
cttcacgtat aaacgtggta taatgaatct aagtccatcc aataacaatt gaatagagaa 73500
caatatgaaa ttagaagatc ttcaagaaga attgaagaaa gatgtgttta tagattcgac 73560
taaattacag tatgaagcag ctaataatgt gatgttatat agtaaatggc tcaataagca 73620
ttcaagtatt aaaaaggaaa tgcttagaat tgaagcgcag aaaaaagttg ctcttaaagc 73680

```
taaattagac tactactcgg gacgaggaga tggtgatgaa tttagtatgg atcgttatga  73740
aaaatcagaa atgaagacag ttctatcagc tgataaggat gttttaaaag ttgatacttc  73800
attacaatat tggggaattt tattggattt ctgtagcgga gctcttgatg ctattaaatc  73860
acgtggattt gctattaagc atattcaaga catgcgagca tttgaggctg gaaaataatg  73920
aaatatagca ttgatgatgc ttttaattat gaagaagaat tcgaaacgga aattcaattt  73980
ttaatgaaaa agtataatct caagcgtcag gatattcgta tcctggccga ccacccatgc  74040
ggtgaagatg tactttatgt taaaggaaaa tttgccggat atcttgatga atatttttat  74100
tccaaagata tgggcattga tatgcatatg agagttatat aaatagatat ataatttaga  74160
ggagacaatc atgtcagata agatttgtgt tgtctgtaaa actccaatcg attctgcatt  74220
ggttgttgaa acagacaaag gtcctgtaca tcctgggcct tgctataatt acattaaaga  74280
actaccagtt tcagaaagtt ctgaagaaca attaaatgaa acacaacttt tgctatagtg  74340
tgacctttag tctatagttt tggcccttcc tttttggttg ggcctttttt aatttaaaaa  74400
ctttcttcta cttcatcgtc tgaatcttct aattcagctc tttttcctgc caaagcatct  74460
ctcacagaga tgtcatcagt atcttttaat tcagtttctt taactctttt cttataataa  74520
gcttcaagtt cttctagacc ttctatcgtt tgacaagagg caattttacc cataaattca  74580
tcaatagaag cttcataaag aaattgttta aattctagta acatcttttt ctccaaaggg  74640
ccgaagccct tataaattaa ctgtttttct aagtattctt agtttgtaca ttgataatcc  74700
agtagcttta gaagcatctt tcatgcattt atacttaaca ccatttactt ctataggttt  74760
agcagctggg ttattagctc ctgaattatc tggcatgtta tctttaattt tctgaataga  74820
tttagcggaa tgtttccttc catacatgcc attattttta cctgattgat tgatagaatg  74880
caatctttta gcttcttcag tccattttgt tgggttcatt cttttagttt tactaatttt  74940
acttccccac gtaattggac gatttttcat gagttttgac atatattgtt tatgttcttc  75000
cgtgtggtgt tttccgtaaa atggattacc ttcacctgat tgaagttctg ccattttacg  75060
acgttcccag gcgtaagatt tattaacgtg tctttcatga gtctttgaat tcatccccat  75120
acatataacg gctttaatta taccgtaatg gtttggatga attttagcta aaagtttatg  75180
agctataaaa tgctcttcag ctgttagttc taccaaatta cacttatcat ctgtaccgcc  75240
catacatcta ggaattatat gatgagtttc agtgtatcca ttaaggcgag cccgattctg  75300
ggctctatta attaaattat cgtatattaa tttataattc aaagtttaac ctctttcatc  75360
acataattaa acttctcatc agcataacgc tgaatacgat caagtccatg ttttaaaaga  75420
tagtttaaat gcgagtattt tttagaagat gtttttgatt tagaaactac gcccgcgtca  75480
tctatgaggt cccagaccgt tgcgattgtt ttagaaccat gcttacgtaa tacgcgaccg  75540
attgtttgca atacaataat tttagattta acaccgtgcg ctaaaacaac gtgatgcaga  75600
tttttaactg aaataccagt agaaaataca ccataactag ctactataat tattccttta  75660
ccgttttcag ctaatgtttt cattacgtta cgtgtttcgg tatcaacttc ccctgatacg  75720
taataaactt tatcgtattc atttttaatt aaatcgaaaa tagctttacc atgtgataca  75780
tgcttaaaca tgacaaaagc gttttcatct ttttgtgcaa gtttaatagc taatttagca  75840
atccatttat ttcttttact gagcccagta ataattttta tttcttcttg gtaagttttt  75900
ccctttaatt tagtagtgaa ctcatcagga tagcgaagaa aaatactatt aatttttaac  75960
tcagttactt gtccatcttc cattaattta gaagtcgtta ctggcttaaa tatttcacca  76020
aacattccaa catactgcat gatattagct ttgccatcac gtaatgaacc tgatagacca  76080
```

```
aatttgaaca tgcagttatt taaacctgat atgatagatg aaatactttt tcctgtggca  76140
agatggcatt catcattcat catcattcca aactgtgaga accattcttt tggttgtttt  76200
actacagttt gccatgtacc aacaattacc ggtgcatcat ttttatattt atcatctttt  76260
gatgctccgc cgccaatttt ctttatcatt gcatgactga ataaacgata gtcaacaaag  76320
tcatcagcca tctgagttgt cagagcagtt gttggaacaa tgataagaat tttaccttca  76380
taattttcca aataataacg tgcaagcaaa gcttgaatta aggatttacc tgcggatgtt  76440
ggaagattaa gaattctacg acgattaact aatccttcga acactgcatc tttttgatac  76500
cagtgtggtt caattctttt atttcctgaa tagatttcta acttagaaag ccattcatca  76560
aaatcttttc ttgataattc ttctttttcg ttaatttgcg ggtcaatcca agctttatag  76620
ccaaagttat cgcagaactt tttaatttgc ccgactaagc cgaatggaag aagacgatta  76680
taatctaaaa gacggattcg tccatcccag ttgccatatc tgaagcgagg attaaaccta  76740
tatccatcgg cctcaaacga aaagaaatct cttaattcgt ggaacgtgct ctcttcacaa  76800
tcgatgcgta catgactgaa gtcgtgaaaa tgtactttaa tatccataat tatgccttac  76860
taaatttgcc tttagaatct cttttcatga gacgaccttt aataaatccg tcgggaataa  76920
taccgtctgg ttgtattaat ttatttattg cgccattatt aacccaaaaa gttcctgttg  76980
tagtcggttt gactttgcat ccttttctgg actttctatt aggatgaacc atccctttta  77040
caaatccttc tggaacaagt tctccaggct taataaaaat atttttagtt ccattagtgt  77100
aacaagttgt acctaatact gtaccaggtg agttttcaaa tctcttagcg gaagattctt  77160
tcatctttgc tataacctct gtagtcataa caattccacc aattccacca ggtttcatat  77220
tataataatt tttgcttttt attagttcag gagttataat ttcttcttca tacatgtacg  77280
cttcttcgga agttttaaac tcttttagta tttttctaga gaaattgttt tcaccatatt  77340
tctttatagc ctgctgaatt gccttaccgg aaccaaggta gccatcattc aggtcgtcag  77400
tagagtgctt tcctatatac tttttaccat ttattagatt tgttgtttca tatacaaagt  77460
ggtacatact attttccgag taataaatat atctatattt atactgagga aatattatga  77520
tagataaaga ttatattgca gagctgaagg ctcttgatga taataaagaa gctaaagcta  77580
aattagctga atatgctgaa cagtttggta taaaggtcaa aaagaataaa tcttttgata  77640
atatcgttgt tgatattgaa gaagccctcc agaagctcgc tagtgaacct atgccagaga  77700
ctgatgggtt atctattaaa gacttaatca atgctgctga tgctgcagag ggattaaaat  77760
atgacgatga agaagtcaat ccagaggcag cacttctgat tgattctccg gttaaatctg  77820
atattaaaat tgaagtagtc gaaacggata aaattcctga aaataccgat gttttgattg  77880
aagatactcc ttttgttgaa gaaaaattcg aacaggctgt agttgagatt attgaatctg  77940
aaaagccgtc tgtatttact cttccggaaa actttagtcc gaatcttcag ctgattggaa  78000
aaaatccagg attctgcact gttccttggt ggatttacca gtggattgct gaaactccgg  78060
attggaaatc tcacccaact agttttgaac acgcgtcggc acatcaaact ttatttagct  78120
taatttacta cattaaccgt gacggatcag ttctaattcg tgaaacacgc aactcttctt  78180
tcgtaacatt aaaataagga taacttatgg cttttacagt tgatataact cctaaaacac  78240
ctactggagt tatagatcag actcagcagt ttactgctac acccagtggt gaaactggag  78300
gtggaactat tacctatgct tggactgtag acgatgttcc acaggatgga gctgaagcaa  78360
cttttagtta tgtactaaaa ggacctgccg gtcaaaagac tattaaagta gttgcaacaa  78420
```

```
acacagttcc agatactgat gctgaaacag cagaagctac tacaactatc gcagttcaaa  78480
ataagacaca gacaactacc ttagctgtaa ctcctgatag tcctgctgct ggagtgattg  78540
gaactcctgt tgaatttact gctgctttag cttctcaacc atcaggcgca tctgctacat  78600
atcagtggca tgtagatgat tctcctgtta gtgaagcaac ttccgctaca tttagctata  78660
ctccaactac aagtggagta aaaagaatta aatgcgtagc tcaagtaaca gcgacagatt  78720
atgatgcaaa ggaagttact tctaatgaag tatcattaac agttaataag aaaacaatga  78780
atccacaggt tacattgact cctccttcta ttaatgttca gcaagatgct tcggctacat  78840
ttactgctaa cgttacggat gctccggaag aagcacaaat tacttattca tggaagaaag  78900
attcttctcc tgtggaaggg tcaactaacg tatacaccgt tgacacctca tctattggaa  78960
gtcaaactat tgaagttact gctgtcgtta cagcaactga ctatgacagt aaaacagtta  79020
aagcaacagg ccaagttcag gtgactgata aagttgctcc ggaaccagaa ggtgaattgc  79080
cttatgttca tcctcttcca catcgtactt cagcttatat ctggtgcggt tggtgggtta  79140
tggatgaaat ccaaaaaatg actgaagaag gtaaagattg gaaaactgaa gatccagata  79200
gtaaatacta cctgcatcgt tacactcttc agaagatgat gaaagactat ccagaagttg  79260
atgttcaaga atcgcgcaat ggatacatca ttcataaaac tgctttagaa actggtatca  79320
tctataccta tccataatct taggggcttc ggcccctttc ttcattttga aagcacacaa  79380
accacaatca gaaaacgatg tatataatgg caccaactcg ataacatgag attgattatg  79440
agaactgagg ttgtggtgtt tactcttcat gagtctggaa agtcattcat tgaaattgct  79500
cgtgaattga acttacaggc aaaggaagtg gctgtattat gggctcgagc tatgactgct  79560
aagaataaat ttgagactcg agaaaaagtt gtctatagaa aaagacatat taataaaaag  79620
gtgaaaaatg gaacagtatg atctttatga aaatgaatct tttgctaatc aattacgcga  79680
aaaagcgctt aaaagtaaac agtttaaact agagtgtttt attaaagatt tttcggaact  79740
tgctaataaa gcagctgaac aaggtaaaac atattttagt tattattgta ctgctcgcga  79800
taaattgatt actgaagaaa ttggtgattg gctgagaaaa gaaggattta gctttaaagt  79860
caatagtgat cagcgtgatg gtgattggtt agaaattaca ttttgaggat taattatgtt  79920
taaaaagtat agcagtcttg aaaatcatta caattctaaa ttcattgaaa aactttatag  79980
tttaggattg actggcggcg aatgggtagc tcgtgaaaag attcatggta caaatttctc  80040
gttgattatt gagcgcgata aagcaacttg tgctaaacgt actggaccga ttcttcctgc  80100
tgaagatttc tttgggtatg aaattatttt aaagaattat gctgattcca ttaaagcagt  80160
acaagatatt atggaaactt cagcagttgt atcttatcaa gtcttcggtg aatttgctgg  80220
acctggcatt cagaagaatg tcgattatgg cgataaagat tttatgtat ttgacattat  80280
tgttactacc gaaagtggtg atgtgactta tgtcgatgat tatatgatgg aatcattctg  80340
taatacattt aaatttaaaa tggctccact tttgggtcgt ggtaaatttg aagagcttat  80400
taaattgcca aatgatttag attctgtcgt ccaagattat aattttacag tagaccatgc  80460
tggattagtt gatgcaaata aatgcgtttg gaatgccgaa gcaaaaggcg aagtatttac  80520
cgctgaaggt tatgtattga aaccttgtta tccttcttgg atgcctaatg gcaatcgcgt  80580
agcgattaaa tgcaagaatt ctaaatttag tgaaaagaaa aagtctgata agcctattaa  80640
agctaaagtt gaactgtcag aagctgataa caaattggtg ggaattttag cttgttacgt  80700
tacactgaac cgagtaaata acgttatttc taaaattggc gaaattggtc caaaagattt  80760
tggaaaggtg atgggactaa ctgttcaaga tattttggaa gaaacttctc gtgaaggtat  80820
```

```
tactctaact caagcagata atccttcttt ggttaaaaag gaattagtta aaatggtaca  80880
agatgtactt cgtccggctt ggattgaatt ggtaagttaa ataaaaaggg accgaaaggt  80940
ccctttgttt tattcatcaa caataatttt tggtagctta acacctaata aaacagacaa  81000
atctgaacga cccgccattt tatccatgtc tccaccatca attattcttg cttctttttc  81060
atcttttgct acagtgtaag gatttgcaga taaagcatat ctaactaata aaccgataga  81120
tggctgcaaa ctttctggat caactacaac tttaaatgca cctacatgtt cagggtcatc  81180
taagtccaga ccttctgtat acggggcata gaaaattgat ccaacaattt ctttttcgcc  81240
aatattttct accacgccaa cgattacata atctaatggg ctgttagtat cgcaataaag  81300
cggtaaacca ttagctaaga acccgtaggc attttgtgaa agatatttgt catcttctgg  81360
tttatgtttt aaccaacctg atgcagcaag aatcgcagcg gcacgagctg aagcaacaca  81420
gaacgttgca gtataagttg attctttttg gatatgcgaa accatttcac ataccattcg  81480
gtataatgaa cgaccagctt caggtgcaga tgcataactc aaatcaatga atccggtatc  81540
agtaattcct gtaactttat agcgttttga tactgtaatc aaagactgta gaatatcttt  81600
attgatttca tccgccattt cagttgcaag caaatcttcc aagaaattag gagcatcgaa  81660
tccatttgct tctaaatctt gcgctaattc aactgtgatt ccagttttaa gtttacgaga  81720
tttaactgcg gtttgccatt tattaatctg gaatctagca tccgcaattt cgctatcaga  81780
gctttcaaat ttgcttgtta ctgcagcatc agaaaataga cgaaccttta aaagaacaat  81840
tgcaatctga agagctaatt ctaaatcgct ttcttcaatg gtagcaaatg gtgtatcttc  81900
taatacttta taaacgatat tattatattt gaataaatcg cctttattga gagttaattt  81960
agactcttct gttaattctg tgatttgttc tcggtctaca tacccagctt caccagcgta  82020
agtagcacca gttttaaatg taaattcgtt atccgggtta aggtatttga taccataaaa  82080
agcagcaaca ggttgattag ttctttgcgt tgctacaatg tcagaatata ttaatttagt  82140
ggtagcgcga gtcaaagcaa cgagatttgg gcgaccgatt gagttgctat tcgttgtggt  82200
tgattcgcgc agaagttcgt tgattttagc cattgcgctt tccttttggt ttatatgatt  82260
tatttatacc ataaaaacaa ctaaagggac ccgaaggtcc cttaaatcgt caaagattag  82320
atacctttaa catatacacg gcggaagtaa gcgtttttac caaggctatt cagaatagaa  82380
ggcataccgc tctggatgcg agaagccgga gcttgagtag cggattctgc aaatgggttg  82440
ataccgatac cgtaacgagt tttgaatccc attaccggtt ggaagttctt cggatcggaa  82500
ccacgcagcg gagtcagagc tacatatgga gcatagtaaa taccagcatc catttcgttc  82560
ggacctttat aacctacagt gaaataatcc tgtttagcat actggtcgat atatacacgg  82620
tatttaccac ccagaacacc tgcaaatact gacttagtag tatcagtatt aaaaccggtt  82680
gccaaacctt gagcagcata agaaatgcca gtatcaacag aagccagtac gttaactacg  82740
ttacgagaag cgataatgaa gttaccttcg ccgcgaccgg tttgacgagc aatttcaact  82800
gcttctttgt caatctggaa caacagagct ttaaaggatt cacccgccca gcgagcacca  82860
cgaatatcaa tcggatcctg gaagtcaaat acaccagctt tagaacccgg agtcagggtc  82920
ataccagatt taccaacctg agcggagtag ttaatccaat caacaacttc acggttgatt  82980
tccagcatga tttcggtagc cagaatacca gacagttcag catcagcatc cataccgtga  83040
acagcgcgga ggtcttgtgc taattcgata gagtaagcag ctttcagctg gcgagattta  83100
gcttcgataa cttgtttatc gatacggaag cccatttcat tccatgggtt atcagtagaa  83160
```

```
ccattgaaac cttcctgaag ttcagcgata gaagtagcca taccttcagc gatttctacc  83220
agtacaccag cttccatttg tttcttaatt tcagcatcta atttagctgc atcatcagca  83280
cttgaactaa ttgttactac agaggaagct tgcagatata cagtaccagt ttcctggaag  83340
aaataagtat agatgtcacc tttgacagta gtagcgccag cagttaaagc agtgaatttc  83400
ttagcagcac cctgaccaga gaacattgca tctggaccat acattgggtg gaatgcttct  83460
ttagcgccgg aagcgattgg atctttacca tatactgcgc gcagcgcgaa tacctggcca  83520
gtcgggctgt tcattggctg aacaccacaa atatcgaaag caatcaggtt aggaatagca  83580
cgacgtacca tacccataac agctgggcca atctgagtta ctgcgccaga agtctgacct  83640
gcggcgatgt tggtagcatt gtaaccgtgg tcaccaccga tttcagcttc tgttaagaaa  83700
gaaccgaatg cctgagcaat tttttcgtct ttatattccg gagctgtctg gaaatctttt  83760
tcctggtttt caaagatttt agcgataatc gcttgtttgc tattagcaat ttccggtaaa  83820
ccttcacctt ccagtaatgg cttccatttg ttcaaaagtt cagctttagt tttgatagtc  83880
atttgtgtta acctttaaaa ttagaaacga gatgcgactt tcgcatatac acttacaata  83940
tcttctgcac cttgtgcaga tttatcttct acagcttcag tgacgaaatt cagtccggct  84000
gcttcagtat caggagtatt tatactctca gtaatagtgc tttcatcttt attagatttc  84060
ttcaccattt ctacgattgc actcaattta cttgagaatg catctgaata atccatacct  84120
tcgaccagag cagagacttt ttctttttga gactcagtca gatctttagt actttcgctc  84180
aatgccactt cacgctgcac ataattgata tatgcgtcac gcttattgag ttcttcgaac  84240
agacgagctg attcttcttt atgttcttgc agctcttctt ccatttcagc tacaacatca  84300
actgattctt ctggaacaac aacgttgtgt tcaacaaaga gctcttttaa tccaccaagc  84360
atggattcaa acagttcggc tttgatgcct ttatcaactg ctaatttatt ttcagcgagc  84420
cattctttcg caagatggtc gatgaattta gaagcttgct cagcaatttt cttctcagct  84480
ttttcttcgg cttcttcttt attttttttct acttcttctt ctgctttttc agcaatttta  84540
gcgatatgag attcagctaa tttaacggcg tgctgcttga cggtagcttc gaatacagtg  84600
ccgaaagttt cttttgcttc cggagaaata ttaactgatt cgaaaatact atcaagagca  84660
acggaagcat caattttttg cgattcagca atcagttgtt ctttaagcat tttgtagtcc  84720
tgttgtttag ataataatat ttataacgct tttttcatgg cctctgcgag agccatatag  84780
gcgtcatcgg cacttgtatc ggcttccgcc gtctgtgatt cggtaatttc cttaggagtt  84840
acccatgcat ccggagcact tggaccccat actgcatcaa cacctacagt taatttgaat  84900
ccttcgttta cgatacgata acctttattt gtgtcagtca atgaacctaa tccacgagaa  84960
gaaactcctg gaatccatcc ggcacgaata ttagctgcta atttatctcc aggaccgtgg  85020
tcaccttcaa taacacgagc tcgtccgtat acgtcatttc ctttccacca catatcttct  85080
ataatgatag cggcttgcat cgggtcaaca ttagcgcgtg gaggatgatt taattctccg  85140
agagcttgtt tagttaaaac ttgctcattg atatagtctt ttaccgcttt ttctaatatg  85200
cgttttggat aaagacgttt atttctattg acgacttccg cttgcatgaa tattccttcg  85260
atgtataaac caggttttaa acctaggtct tttccatcat gagattcaag cattggcaca  85320
ccatcaataa tttcgccagg ttgaccccaa gtttcaatta gtaattgggg ttcattcatt  85380
agcttaatcc taatgcttta cggcgtttaa gagctttttt acgcttacgc tgagcacgag  85440
attgacctgc tggattggca atcttcgttt tggtagcttt gcgagcaatt tgtctacgct  85500
ttgctttaga cagcccggtg gtttgaaatg cattacgttc acgcgttttg cggtctttgg  85560
```

```
tacgtgtaat ttcaccacga gcagaaacat gtttaacgat gaattcattt agcggcatat  85620
cttcattaat agaagctaat gcaatcgcta aatcagtttc atcatcaagc atattctcga  85680
caattgtatt tatatcgtct ttatttaaag cagaagacaa ttcgtcaaag cgaccctgtg  85740
cttcaggaat aagtgcttcg acattctcga gaactaattc atgagtttca gggatcagaa  85800
gcattattca tcatcctcgt cttcgtcatc ttcgtcagag tctttgtctt ttttgtcgtc  85860
tttatcatcg ctatcttcat catcctcgtc ttcgtcatca tcctcatcat caggttcttc  85920
accttcgatt aagaaattgc gagcgatagc gatttttttct tctttaatta aatcaatcgt  85980
tcttgcagcc atggcttcag caaagaattt acgagcggct acgaggtcgt ttgatttaat  86040
agcttcaatt aaaccttcca ttaaaaatcc tcttgttctt ggtcggggtc ttggaaacga  86100
gcctctttag actcttcttc aatttgcttg gcttcttgtt ctatttcttc atcagtcatc  86160
tgcaaaatat ctttcatagc agttctgtga gaaatatatt taccaataaa tggttctgcc  86220
atggttagca tattaattct tcgttccaaa atttctgctt ctttgagttc agtaaagtag  86280
ctatcccgat gaaattctat cttaatatta tttatttcat cattccactc atcttctgtg  86340
attatacctt taagcaacag atttgtttta agcggatcca ggaaaacttc ttcaaactta  86400
tgctgtaact cacgaataaa tttagcaaac gttaattcat cacgtgtaat gctagttcca  86460
gaatcaaaca tcacaccgcc ttgttggtct tgcgggatgc gtgaaagagg aacacgtaat  86520
gccatataaa gagcttgtct aaaccaacga acatcttcca tattaccagt attatcggca  86580
ccaggaagag tatcaacttc tgtcacagct ttaccatcgc ggcgctgtaa ccaatagtct  86640
tcggtcatag acatattatg ctgttgattt tttattttac ctgttgatgc atcatatact  86700
acacggtttt tcatcgtgtt catgacatgt tgcatgtgct cggcagcttt acgagcaggc  86760
atattacctg tgtctacata ccaaacacga cggtcaggag cacgagtaat acgataaatg  86820
actacagcat cttctaataa ttttaattgg ttagcaggtt taacagcacg atgcaaatac  86880
ccgatgatat ttttaccaca gcaatcgact aatccagaat gggcataaac gatggcagct  86940
ttaggaattt ttatttttgt gccagcttca tacattctac catcacatgc atatgattcg  87000
tgtgcagtat catatataaa atactctttg taacctttaa ctatttttgt gccagcttca  87060
gtttctgtta taatttcacg aacatactga acttgacgtg ggtctaatct acgtaattcc  87120
tttatgcctt cttttggacg ttttggatca ataattttat gaaagaaaat tcttgaatcg  87180
acataccaac gtctaaaatg atcagaacct tttcgttgaa atgatagatg atttaataca  87240
tcgctaaatt catctaacat catattttta atttttgggc taaatttaga tttatccaaa  87300
tttaacgcta cgacttcagt atcatcttca tagacgatag cgtctgaaac gatttctgaa  87360
actgcattat ctacttcata gttattcatg agattacgat atgtatcaat aagctcacga  87420
gtagttttca ttcctggttc atatgaacca aaaattgttt ggaatgcagc attataagga  87480
gaagcagctt cattcgagct tacttcaaat tctcttgctc catcatcaag ctttggggct  87540
gtaatggaaa caagatcttc tttttcttgg tctttaaaat ttcgttcgtc cattttagcc  87600
catggagcaa acaaacttaa tacattaaat ttcattgtat tctccaaatg ggaattatag  87660
ttatatttat aatggacttc tctgctttaa gcaggatggg gatttctccc cattcatttt  87720
attcccaata atcgagagca agagttactt caaaggtttg gatttcattg tttgaatccc  87780
aatctaattg aagttcaccc acgttagtag gccacaggcc tttaatttcg acttcttttg  87840
ttacagtttt agcatcacga gcatattggc gaacaacagc actcttttta tactctgctg  87900
```

```
gttttccacc agtaatttcg ttcccttgcc cagcagcaat gctttgccaa tcaacaaact  87960
tctggcgagc atcatgtgcc tcatcgttca ttactgtaac agtccagtca tcgaatgtac  88020
gatcgcctgc tacgttaatt ttacggttca taaaaccgac tggaattttt tctacaatac  88080
cagctggtaa agcagtggct ttacattgaa acgtaaaatt ttgtccaaga taagaaattt  88140
ctacttggaa taagttaggt cgagcaaaat caccagattc aaacgctcgt gttacatcat  88200
ctacaaacat attagcctct gtagtattta tatccctatg tttaacctag ggcatataga  88260
attaaagaat taaggatata gtgtatttat atggcctgcc gaaacaggcc tttagaatgc  88320
accgtattaa cctgcaagac cagttaactc atcgaaatct gcaccagtag cagttgctac  88380
gaagtttaag gtaatgtagt taatgcttct agccggttgg atgtagaatg ttgcaacaaa  88440
ctcatttcta tcaattactg acggagtgtt atttgttgta tcgcaaacta cacgatattc  88500
ataaattcca ccgagagctt taattccctg caagtactgg gaagtttctg tgcggaacga  88560
tgaacgagta aacgcgttgt ttaattcgaa caaacgatat tttgaactac gtccgatatt  88620
cgttttcaac atattaaaca gacgacgaac gttaatacga tcaaatggag aaggaacaga  88680
agtagctgtt ttatcaccat acaatacgta accatcacca cctgtaccag ttactgggtt  88740
gatagcttct tggtataaac gatcgcgctg cgcctggcga gtttcaatag caagtttaat  88800
aacgttaaga atctggccgc gattataacc agctggggac atccaagtct gagaaacgtt  88860
atctgttctc gcgcataaac cagcaatatc agctgctaat ggaacccaac gattcacatc  88920
attatatttg tcatactgat acttgtagtt accatcaatt gctgcataag ttgaactgat  88980
attaaagtta ttatcagtgt atgaacctgc tgcggttctc cagttgacta agttatcaac  89040
agcgcgagtt acaggaattc caactacagt ttcgcgcggc ggtgagcaca gtactaagca  89100
atcttggcga gcatccccaa ttgaaacgac gtgtttttgg acagtagatg ctgtttctaa  89160
agattcaccg gcacaagaac ccgcaataaa caactgaaca tcaacagatt cacggtcagc  89220
aaagaaatcc caagcttcca tcaaatctcc tgctgttact tcagcatttg atgataatcc  89280
accagacaga gttaaaattc cagagaagcc ttctggccag ttttgtgcag ttgcaaaaat  89340
atattctgaa ccaccttttg cgaaaaagtc atcgatatag atgttactat cgtaaatatc  89400
tttttcaccg cgcttagttg aaagaacaac gctttgaaca atagcatcat tacgacgaac  89460
tataatagcg tattgcgaat cagtttgtgg tccatatcca aacaccgctt tggcagtaga  89520
tgcgcgtgtt ccgccacctg gataaattgg gagtaatgca gaagctcctt ttgcgtagtc  89580
agctttagat acaatttcga tttcaatttt atcgcctaac tcgcctggat aaagagctac  89640
tactcctgga attccatatt tttcgagatt tgcttgaaat tcaaccgctg tcacagcagc  89700
ttcagcattt tcaatttcag ctaataaaat accggaatca gtaataattt ttccaagagt  89760
tattactgca gctaaaccag aggaagacga agaaatttcc gcggtccagt tagaacctaa  89820
tgctggatat tcaccgactt ctttcgcttt agcgataatt tttgcggtag gaatattaat  89880
tttcttaatt tttccatcag catctacttc ggtaatttta ccatctgttt caacattttc  89940
tgaaacatac ttaaccgtga ttttatctcc aaccgcgtag ttactacctg gggctgaaat  90000
agtgtattca atattaccgg caatcggaga tgagttttta gcggtatctc tatcgacagc  90060
acgcacaact cgcaaatcat ttccgtattg taagaaattc attgcagaca taaaatagtc  90120
agcagtttca gctgtaggtt gaccaaaagt attaactaaa tctacttcat ttgtaacctg  90180
tttaatttga aaagcaggac cccactggaa tttaccggcc aaagctgctg taccagtaga  90240
gttattaacc acggtgcttt gaaccgtagt ttctttgagc tcaatgcccg gagataataa  90300
```

```
agtcattttt aatcctcttt aatatgcttt aatatattta taccattgac ataccatgag  90360
atactggaac atactcagca gaatgaaccg aatcaacaaa tataactgga gcgtattcat  90420
cacccatatc ttggagttct tttgaaaaca cttcagacgc taatcgcatg tcatctttgt  90480
cagcataatc aataaatttt gattgcgttg ataaccatcc aaaaatcact aaagacatta  90540
ctaaatcgtc gtgataacct tcttcagccg cccaagacac gcctttttca ctaaacgttc  90600
taaactcttg aatagttgca cggtgatgaa taataagctt atctttttca ataaggtctt  90660
ttaatgtaga gcatcctact gctttcgttc gtttagtttg cttcattcct aaatcagtat  90720
atgaatcgca aataacgcct tcgtattcta aatccatata aagtgatttc gcaactgaca  90780
caccagtact atttaattca atataaactg ggcattcatt atattctact aaataacgca  90840
taacgatgtc aggcagaatt aaatgagaaa tggtgtttga atgtaaaaca ccaacctgtt  90900
cccacacatc atcggtaaca tcaataatat gtaaagcgtg ataatcttgc ccacgacctt  90960
ctgaacagtc taaagttgca atatattttc tatctggttc aggactttta aatcgatgaa  91020
aaccgtgatc gtctggagtt acttcaatga aatccataac agctaatttc attcctgaaa  91080
ttaatgtacc agaagtccct tcaaacgctg cggtgtgttc ttgacgaaat tgagctaaag  91140
tagaaccatt aatggtttgt atgctccatt gccatccatc gtcaaaaata tcttcatcgt  91200
tataaagacg ctctttaact gaattccaaa tagcagtgta tggttcaaac cctgatttac  91260
cttcaacagc agcagtccaa atatcataaa aatgatttaa tccattagga gtcgtagtaa  91320
taataatttt cgaacgacga ccagatgaaa taactggttg aatagcaagc caggaatcat  91380
ggaaatttgg aataaacgcg cattcgtcaa tataaatcat tgcgaacgag ttaccacgaa  91440
ctgcgtcagg agaggaagca taggctccga ttgaggaacc attatcaagt tcaattgaac  91500
ccttattcca ttcaacaatt cctggttgta aaaagtcagg aagcagttca attgcttgct  91560
tagtacggtc taaaacttcc gcagacattg agcctttgtg agcaagaata cctacagctt  91620
tatccttgtt aaaacataca aagtgtgcaa ggaaaatagc tactaccgtt gttttaccga  91680
gctggcgcga tagattacaa acagtcatac gtttagatga cattattttg agcatatcac  91740
gctgataatc acgtaattga acctttatga caccatagtc aatatgagta atagcacagt  91800
atgtttctgc aaaataaaca atatcgtctc ggcatttttt ccattcctca accatttcac  91860
gagtccattg tgttttaata ttagctcgtt tcaagttagg aagacccata taccgagatc  91920
ttttattatt cttatcttta taagtttgaa ataattcagg cttatcagag ttatttggaa  91980
tttttactat tttgtgtaga cgaaggtaat cactgaattt ttcaggatac cattttccat  92040
cccactgaga ttttatccaa tgaattccat cttcatcttt tctttccgct aagcttgggt  92100
gttttattaa aatttttcca gcttcattta acggatggaa atcatttaat gcattaatcg  92160
gttgttccat ttatcacctt ctcacgagct tcttgagcct cgtaagcatc accaatttcg  92220
tccattaatt ctgttggtga acccatgaat actgtcgcat tctgaatatt catttgacct  92280
gtaggaacag cgcctttggt gccaacctgc tcagatgtaa tatctttcat atctttatga  92340
agcttcagta tttctctgtt cgtcgtagtc atttgcccca taagagttgc aaatacttcc  92400
atgtgacgag gagaatcagc attctttgct gtctcaagaa aaatcttggc cgcgtccatt  92460
agcatttgtt gttgaaaatg catatttcga cgaactacac cataatcatc ttctaagtca  92520
ggagtacggt tttgaggatt gcttttaact tctactaatt gcagaggttc atatacttta  92580
atttcctccc cgtcgattcc ggggaggtca gaaatatcta aaagtttgtt tatatcaaga  92640
```

```
ccttccataa taacctctat gttcttgggc caggaggttc tggcggtgtt ggtctattta  92700

cattgctagt gaaagtttgt tttactgttc catcccagtc ttctgggtta atatctcgag  92760

gaacaacttc gttatcgaca gattcaaaaa caccttcgcc atcaggcaaa tctcttgtat  92820

tggcgtgaaa atctgtataa gtagtacgaa ttaatccttc tgcatcatct accggaggat  92880

acatccatcc atttacttca aatgttagtg accattcaat tctacgacga gataaattat  92940

ctccatctat agattcgtct atagcagcag acatcagtac aattttaata tccctttttaa  93000

atggaatatc atttccaaac tgttcgtaca tagttgtatt aaaatgaggt tgaaaatatg  93060

gaagaatctg ttcaactatt tgaaacatat catcttcgta gcgagtaaag atactcaatt  93120

cataaatcat tttaatagga gatggattat actgcgatac tactgaagtt gcgccttttt  93180

gtagtaaatt ctgatttaaa atgtttgttt taaatggagc attatagcta aaatcaacta  93240

aatgtaaatt tatacgaggt agaatagttt caactttagc tacatcttct tgtgaattta  93300

tcgatgtcca tttattcaat ttcatcatga agtgttcctt tgatgcatac gtaataggaa  93360

cacgtataaa cttatcacca gattctaact gacgtttgat ttggatattt gaaaacaaat  93420

cgcccatcaa ggtagcatat cgtctaaaag acgaattata aaaataacca aacatgattt  93480

ctcctaatct gggctttaat tagtttataa tatttattaa tccatgaaat cattatcaaa  93540

tgggctagat tcgaaagatt tgcctctgtt attgacaaca acataaggtt caacatattc  93600

tttagcttca gaattaattt gatctacttc agcatactga tcaatattaa tatcatgaat  93660

accattaaga ttgcgaacag gatttaattc taattcactg aattctggaa tgttaattcc  93720

ttcatttttc tgtagaactg gattaatttc ttctccagaa taaatgaatt tacctgctgt  93780

aattttacga atagcgtttt ggcctaattg ataaaatgga tcatatggtt caacccagtt  93840

aatttcgaat aagctgttat ccataggaaa atatatcaaa tccccttcct tgggttcttt  93900

tccgttaact tggtgtttaa acaaatttgg attaatagac aaagttactt catcctgtac  93960

ttgcatacca aagttaccaa agaatgattt agctccttca tatccttcaa atgaatttaa  94020

atatgcagcg aatttccaag ctttagtaaa tttatttttt aagtcttcgc cgaatatcaa  94080

atcaggggaa acatactctc ttggaacata atagcattct acacctcgca tttgaatgct  94140

ttcagctact aatacatcag ctaatatttg gctgttttta taatgattga aatttacata  94200

aggatttagt atttcagttt cattagtctg agaataacca gtgcgatttt ctaatttagc  94260

aaaaagattt ttatcataag tagccatatt aacctaccaa aattccaaat ggaggatcga  94320

gcaagtataa ttcttcgcgt aatgcttctt tttctaatcg agcttcttct attaagcgtt  94380

gtccatcaat tgtaacaccg cctggaagca tcatgccttg gtgacgtgct aaaatttggc  94440

catttaattc tttagctaaa gctgtagcat agtctttcac ccaacgatta ttataagcac  94500

cttgcttaac atctgggtct tgacccacaa cacgacctac taaattatgg tctggattat  94560

tatatcgttc agataatgac caactatctt gcggaccaac tgttccatat cctactgtat  94620

ttccaaccat tttgtttgta tcaatgtatg atttagtcca gctttctacg ataatcaaat  94680

catatttttg gaagtttccc atgactttga gttgttcatt tgctgaattg aaccaaaagt  94740

ctggaatagg agaaagcata tcttgcatca ttcccatgta actggtaagc tgggtaaaat  94800

accctaaatc agctccaaag gcgtttggtc cataaaatct attacaagaa gtccccatgc  94860

caccattaat accagccatt cctaaaagaa agtcagtaaa ccatggatat gtagcgtttc  94920

cgtccattga cgttattgat ccaacatttg tacgtaaaat tcgagttact gcgaatacgt  94980

ttgaacctct taaatcgaag actccggtct tatatttttc ttcgtcatct cctacataaa  95040
```

```
atacatgaaa ccctttgtta agtccatcaa aatggtattc accgtataat tctagggcac  95100
gctggatgca atcatagatt tgatcgggtg ttaactcaac attaataatt ggagccccta  95160
aacgtcttag aatgacatct ttgagttcct ttggattttg agaattatat cctgacattt  95220
aaaaatcctt tggggccttg cggccccatg ttatgctggt gataaaaagg tagaaagtaa  95280
tacccattcg ccgtctttac gaacgtaagc ttgaccatct tttggagctt caggaatata  95340
acctgcttcc tgtaaagtct gaacatccgc ctgtaatgaa gatacattac ttttaatact  95400
acgcatttct tgattaatag aagaaatgtt agtttcatta gcttttattg aattagttaa  95460
tccacgttct tcgacagttg aaccatttgg atttgttcca tttactaatt tatttaatgt  95520
tacaacctgt cctttaattc cggaattgtt attaccaatt tcaacttgca agttttgaac  95580
atcattattc agtctattaa cggaagtttc aacagttgaa actctattta aaagagaccc  95640
aggaggagaa ggttgtccac cgctagaatc agttccaaca atttggttta accacgaaac  95700
gtttgctcgt agtccagatg aagtgttttc accaacaatt ccatttaaaa actcaataga  95760
tgttgtatta tctttaattt tacctttaat actagaagga atatcatctg agccaattga  95820
tgtttcaatg acagttaatc gctgtttaac acctccgctt ttatttagct catcagttaa  95880
agctgaaatt tctcgtgtat tagtgttaac atctgtgatt attgaagtat ttcctggata  95940
tccaatagaa gttttgatag atttaatttc ggaattaaga ttaatttgtg attgatctaa  96000
attatgcaca cgtgaatata tactttcact aaatgaaggt ggtctttgtc ctaattcctg  96060
tctaagattt cctacttcga ttgtaagcga acctacatca gattcaataa atttttcttc  96120
taaatcgctt agacgtattc cttgggaagt tatagcatct gtattattaa taatacgatg  96180
cttcattccc gtgctggtat ttcctacaac aggaagacca ttaatatctt gtccagcata  96240
ttgtcctagt tccctttttaa tccacaacaa atcatttcta atcgttctat aaactgaatt  96300
tgcttgcgaa ttaaatggac caatatcaga aagaatatta tcaaccgtag tatttgtacc  96360
atttaatata tcagtatgtt cacttgtgag cgtctttaaa cttgatatat catttttatt  96420
aacgctgatc tgtgatagcg cttctatatc tcctgataca tctaaaatgc cttgaatagt  96480
tttaatatct tcctgagatg tttcaatggc agttttaaga attcctacat tttcatcaag  96540
aatctcaaca tttttaaaca cggaaacagt tggtctattc attgatccat cgtttccata  96600
cttagtacta gctcctagta tttcttcacc atttttaatc catgaaatac gttcctgacc  96660
ttcgccagga acgctatcaa caaaaggtaa ctcttttaat tcaatcattt gtaatcctta  96720
gtaatgaatt ttaataatat agtttaatga tatattccat ggtctagttt cataaccaat  96780
taatccttca cgattaagtg taccaagggc atctctcggt ccacctaatt caaatccatc  96840
attagtgaag tatgaagcat tatcccagtc ggcatatttt ctagttccaa gatatccttg  96900
ataaacggac gcgccaaatg gagcttcatg tctttggtat tctccccagc caccagcatg  96960
tttatggtat gacatttgtt gtgcttgaac acctccaaca tgcattccgt cacatcctac  97020
gccaagtcta tcctttccat aaccatcttg tcctcgttga tttaaaatat gacctcctgt  97080
gccagctcct ctgacgaaaa gacctcgcat atcaggaatg ccagggttat tccaatcacc  97140
accaaatctc gttccaactg tgtttctata atcaggatat tgatctcctg acacggttcc  97200
accgtggcac ataatccaac ccggaggtgc agaatcaccc gcaaacatca taatagttcc  97260
aactggaacc ttttcagacg catatctttc agtggcaaca ggttgatcgc catttttcca  97320
cataccgccg cgtgaccaaa ttccatttgc tgtaagatgg tctaaattta aagaaccatt  97380
```

```
aatagtttgt ccaccgcgtg tattaattac atctgcgttc catgctaatg ctccagagcc  97440
atcaccctcg gggcaatac cggcttgcgt cgttaatttt actacaccgc gcatagaacc  97500
agtagctcct cgaccattta atgtttcgcc tgttactgca acatctccca aattactatt  97560
aatttccgac tgcgttccta aacgtataac acccttatat tcttgtgttg caacggaatt  97620
cataaaggta tatggggaaa ttgcatatcc ttcgcgaaga gttccttgac gagtttgagc  97680
gacagtagat aattgaacta cacctctaac agattctgat gctgtgtctt ctgaaggagc  97740
tatttgtgaa attaatttta ttgcaagttt ttgcgttttt aatggagtca ttgccgtagt  97800
atcatcaact ccagctaaag ctgcaggtgt agatgatatt ttaataaccc cgtttgatga  97860
ctcagacgaa tatctatttt ggaacacatc gtcagtatgg tatttcagtt tttgcggcgt  97920
tattgatgaa ttattatctg agccttctaa tgtttcttca tttgttgaat agcgcgttaa  97980
accatattta gtttcagtag catttggata caataatctt gttgctaatg tagcaggtgt  98040
aacgatttta gaattattag ttccatctaa aacctcttgc tctgacgcaa tcattgctat  98100
tcctttaact tccatagttg catcaggaat accatttacg ccaatattac ttatttttga  98160
taatgcagac tgcactgtcg tgacagtgtc aggaaaattc gatccagtag gatcgaattt  98220
aacatatttt gattcatttg atacgtgctg atatgtattg ttactcatgc tattctctca  98280
aaataataaa atactgtagg ttgtgtgtga ctatctagcg taacagtttg cgcacctaat  98340
aattgccaag ttccataccc aggtttagaa ggagaaatta tttcttgttt gaaagtaatt  98400
cctttatcag agtattgttc taagatatgt tcttggttat ctaaatactt aacttgtatt  98460
ttatttccta tggtaggatg gtcttcaaat gaatcaattg caataaattt tgcaaccatt  98520
tcctgtagag ctgttctaac ggcactggta aattcgattg aagtcattcc attagtagct  98580
ttaacaggaa tgccaaacat gttaacaata accgggtcac ctggtttggc tgaagtatca  98640
gtaacagttc cttcaaatga ccaatagtct gtttgttgca cgccagtagg agatacgccg  98700
cttatattaa ctaatacagc tccaacctgt tgctctgcca tatttctaac atcattgata  98760
gcagattcta catttgggtc ataaaaacct tttgctattt gtgaaattgt tacagcacct  98820
actggctgat tattcataac cgaaatatca tttttcttag ttctaaaacc aagaaaatct  98880
gctaagcggg aaataactcc cgctttatta ttaagtaaac tcattatgca atccttatcc  98940
aacggtatac agtaatagac ggttgaatat tactaatatt agcaggagga gtatgtgaag  99000
agtttgttgt tgcgtagtct tcacgatatt ttgtatatat aggaccagtt tcgtctgggt  99060
catattgaca tcctccaata ataactgatc cattttcgtc ttcaattaaa actctttcat  99120
cagttttagt cgcaggaaga tttgcgtttt caagcgttac tgatgttgta ccaactgttc  99180
caccggcggt atgcgaagga tttccgctag aatctaaatc attattgttt aatgcaaagt  99240
ttggatctgt aacatcatca ttccatccta ctaaaacctg ccctttacca aataatttcc  99300
atgaaccaaa tcccatataa gtcaccggat tatttgggtt tatagcattt tcataaattg  99360
aaccaacagg ataaatgctg tcgaaaatag atgatattga attatacgtt ctagtataag  99420
aatcaacttt ttcaacattt ggccaaccga ttttatcaaa atctgttaag gctacatcac  99480
cagtaacttc agtagatgat cctttactaa cataacggtc atcagttaat tcaataatgt  99540
catctttttc taaaagagtt cctaaatcat tattgaacca tgttataacg attatatcgc  99600
cggattcaaa ttttctatca aataaaagac taacaggttt tccatcttca tattctatag  99660
aataatctgt attcgattct ttccattcac cgccaagaga tatacatcct gcttgcgtat  99720
ctgaattagc accttcacac aaaaacagag gatatccggc tgttccagct tgttgttgta  99780
```

```
aaattccatt aaaacgaact tcaagagaat taggattaat aggttctcca ggaattaatc  99840
caaatgcaga gaatggaatt gatttcattg ttgataaatc agtaacgtaa atacttcctt  99900
ctaaagaagt ttttgacgtt aattttgaat ctaatacttt tatttggcgt cttgtatatg  99960
aacttctcca ttgtgataca ccatccataa atgtttcaat ttgaacggtg tcaccaatat 100020
tacaaggctg tcttaatcga atgttaaatc catcaagagg aatcaattct ccttcatttt 100080
ccccaggaga gccaaagtca ctgttttcac taaatacatc gccataatat aattcattac 100140
cgcggtgttt tactcggatg ttattaacat tatagctagt tccacggaaa acatctaaaa 100200
agtctgtttg tccttgaact tcgactaaaa attctttacg tgctacatta ctaatatctg 100260
aactaataat tttgtcaatt tgtttgtttt tgacatattc ccaacgtcct ggagcacaat 100320
aaactaattc taaatcgcta aattgaacat taatttcaac tgatgacgat gatcctttaa 100380
tagtatcacc agaagcggct actagagtaa ctggattaac attccatgtt gcaaatacat 100440
ccctagcttt aattacttta ttataatcat taacggttcc tttaggaagt tgtagagtta 100500
ctcttccaga tgaagtgtta atggcatatg attttcccca ttctgctgtt agtgtttgtc 100560
ctgatgaagc attataagtt ttccaggcac cagctgaata tggaacatca ccgtcaccaa 100620
gctcgtaata aagctcatca aagttttcat ttatttttat accaccttta cgcaggtagt 100680
caccggtacc atcatctaca acattaccga tattaatatt ttgtttcatt attgagccac 100740
cccgattttc tgcgtagcga taactttaac tgctgctctc atgccaacaa tagaagaact 100800
tacagtcgct gttacataat ttgttttaat actaaatgca atattagcga tttcgtcttc 100860
ttcggtttca tttccaaccc gcatgacagc atattcagaa gaaattacct ctgaattaac 100920
agtatctaca agaatattta tttctgctgt tttaattttt cttccatcta ccgattggca 100980
tgtaactagc aatttagcca tattgtattc agtacgatga aatagtggaa tatcaactga 101040
cccggatgta gaaatattcc atgtaccttc agctggcgat tccttttggc caaacatact 101100
ttcaatagaa taattccaaa cagacgtaga attatcagat gaaatacagc gtaaagttac 101160
tttactatat ggactagtta ctactaaatt acctgaaaca ccttttattg aatcaatcgc 101220
ttgaatcgtt aaaggattag taactgatat agatccattt gagttaataa attcaacgca 101280
gtcaccaagt tcgcctcttt caatgataac tttaacacct acagtagagg tatcaatatc 101340
atgcctagtg ccaactttta ctggagttgc gtactctgca atagagtgtt tttgataata 101400
tccagtagca tgaataattt ggccatctgc tccagtgcca tttgctactg ccattttacg 101460
ctgatcgcca aacgcattat aaattgcgtt aaaatcacta ttaattttat taccaccgtc 101520
gaataagata tcaccagtag aagcgttacc aatttcgccg gtatcaatca atttctttgg 101580
ttcttgaatg aacatagcgg tttccttatg agtttatagt atttataaag aaaaagggag 101640
cccatgggct cccttaattt aaaatgtaaa cagaatattg atttcttctg tttgatccat 101700
tgccatgata ataggtggcc tattttccat ataaatcatt tcgcccgaat gcctcattaa 101760
atcttccgga tcataataat ccttttcagc tttaacgttt gggtcatttg gatgaacttt 101820
agcttcaaga ggattggtga ttattgatat ttgtctaaat cctttatttc ccggtaatgc 101880
agcatcagga aagtaaactg aatctaaata tgctttaaaa cggatagtat ttgccttaac 101940
acggtaaatt aatccaaaat catcttgttg ccaagtgaga ttatcttcat acccccatct 102000
agcagggtct tcttttaatt cctcaggcca aggaactacg atatattcat tcgtgcatct 102060
atttatagat acatcaggcg gaatctcaaa aagatattcc caaacataac cgtcgccggg 102120
```

```
ttcgattgtt ccttcagcgt ctcctcgacc ttcaggagga gtcattgacc taacagaagg 102180
agtccatttt ccacccaact taagacattc atccttatta gttaaagatg ctattgaaca 102240
cgttccggta tcaggaacat ctaaacaacg atatactaac cagcctgcgc ctgattcagt 102300
agcattgtaa ggagctgagt tacacactac aatatcgtta attctaaatg tgtatggatc 102360
cggatatcta gtatctcccc aatctctacg aggaataact gcatcaagca tagacggaag 102420
aacctttaca gttcccatca tatgagtcca catgtcagtt acacctaata cagaatcagt 102480
tggataaggt ggagcaaagc ccacctcatt ttcatttgat gaccacggtt ctgatcttcc 102540
aaatgtgata aagatagtgt ttttatccgg accacttcca attgaattat aaaaattcaa 102600
catttttct gttctaaatt ttgaagtaac tatcgcacga tagataacac ttgaatcatt 102660
catctatttt aacctgtgtt ggattttcag ggtctcttgg atttcctata ttatctttta 102720
gacgtttatt aactaaatct ctaaattgcg caaatgttgt tccagatgcg tcaaatagag 102780
gactcattaa tttgcgtcgt tcagacggca attgaccttg aaatattgaa ttgttatttt 102840
cagtattata gtcatcagga agaggatatt ctacgccagc cattgggcca ggttcataaa 102900
ttgcttcgcc tgttaccgaa tcatgctcaa tttcaccagt cggagtcaat ttagctactc 102960
tatcagcata ttcagtaggc aatccagaat cccatttata gtttttgtat ttattaatta 103020
tagtctctgt atgtttaaga gttaaaccaa cattaataaa cattgttaaa agagtaattg 103080
ctataaatcc aaatcctact ggatgaacaa aacgaataac gtcagatttc cagcgggaag 103140
aaggcaaatt ggatttaatt ttcattacat aatatgatcg acttctatta atatagtcta 103200
tattattttg aagcaaatct tttcctttaa ccccgcgaat aatttcgcct tcgaaactag 103260
ggagtctttc tgctttaact tcttgaccgg caattaatct tcccaaaaga ttatgaatag 103320
ttacggtcca ttgcaattta ccattagaat agcttctttc tatataagta acattacatc 103380
ttcctgtagc tgtataaatc gtttgtccta ctaagtcttc ggtcaaagaa tcagattgaa 103440
cgattatatc atattcagta ccagccccag attcgatttc aatttcaact tcttcattat 103500
aaagaacttt aaaaagaaat ttgtatgatg cttcaattcc tttagtagaa taaaaatcat 103560
agctgcgtga ttcgaaaaat cttgcgacag catcacgttt gtcagcattt aaataaatgt 103620
ttcttttata tatctctgac cacaaatatt cccatgcatg ctcttctcgt ggatatttgt 103680
tacgaattaa atttcgtaaa ttgttatact gagttccata tccatcagaa agatattgaa 103740
tatatgcttc gcaaaatgct tcaaaattcg aatcctgcaa caaataagaa tcaggcatca 103800
ttgtgccaat taatggtctt aaatcaggat cagctaatcc atgctcttct tccggtgacc 103860
aaggagtttc acgctcttgg ttttgtaaaa atgcttttaa aaatattcca gttggcttcc 103920
aaattatttc aactgtgtct ctcactcgat agttaaaatc atagtaagaa attatttcac 103980
cagaagattt ataaaaaagc atcccagacg catatttttt aaatcccgtg aatttaacat 104040
ttggcattac tatcgtgcaa tcaccatcat cccagtattc atgaactaat ctatctggcg 104100
atgtttccgg aatattttct ataactttgg tgtattttaa atcagcataa actactacag 104160
ctctgtcaga gttgtttatc caacagcgtg tgttagattt tttagaccag ttaaagaatg 104220
gttctgcata gtatttcatc ggctgaggcg taaaagtttc ccaatcagat tttcatctg 104280
ctataaatgc catcatatga taatgcttat cagctagcca ttcacgagga aattcatatt 104340
taacagcacc gattaactga tacttcacca cagtttcaga gtcattaaca atattatcac 104400
ttaaaaattt aaaattactc gaagatagag aaactaattt accatcagtt gacatattcg 104460
catatcccgg ttgaatacgt cttctttctt cttcagtgtt accaaaaact cttttccatg 104520
```

-continued

```
ttttcgtgcc atgatttaaa acatatattc ctttatcagc agaatcaatt atttttgatg 104580
ttctaggatt agcatttaat gtttcaactt ctccaataat aagagcaaaa actttatcac 104640
caatagaatc cattttataa catactgctt taggatttcc ggttatagtc attatatcag 104700
gttcaaatag cctttccgaa tatgttggag ataatgggtc agaatctatg ggtgcattac 104760
tcgtttttat gtatctaact ttgtctctgg cgacaacgta aatgtaatca tcggtgcaag 104820
taatagcttc tgcaatgcgg tatacattag ctggcaaagt cgcgtaagtg gcaaaaattt 104880
ctacatcaaa tcctagatgt aattggtcgc caagtttagc aaatgttata tcctgcgaac 104940
taaatctgac atcgtcagct gaccatctga catcagtaga tttgcggcca tagaaaatct 105000
tgtcgtatcc tagaacgtat gttgtgttcg cagattggta atataccgtc ttagataaag 105060
gatatcctac acggtcattg aagagcttta cagctttcca agtttgtcct ttatcattgg 105120
atactttaac tacaggttga tagcgctcaa aaaggtataa aatcccttct gattccatca 105180
aataaactcg gttaatatcc ttacatactt gctgaataga accttgtatt tcatgatatt 105240
cattttcacc aataataaaa ttacttattg atgaaacgtc aacatatgat gggctgaatt 105300
ggaacgattc attcatcaat gcagccatta tagtgtcatt attaaaatta acatagttag 105360
aattattaag agtaaatttt tcctgaatga atttattagc taattgcatt tcaatcatat 105420
tttgaaatgt gtaagcattc gtagcaaaag tttcaaactc ttcggtataa atccaatcag 105480
actgctcaaa atcttgcgca gctgtagcta ctctaataat gtacgatgtc aatggattag 105540
cattatcaaa aaagaagctg ttatttgcag tatatcctaa gttaacccat ctgtattgat 105600
tactcgggag attttccccc gagtctgttt ttgtctcagc gatttctaca aaatagtaga 105660
aattagcacc aacgtcatcc cagcgtactt gcacctgatt tgcggataac ttggaaattc 105720
tgagactagt gactgaaggt gcttttactg tcattgtgat ataggctcca aatcgatagt 105780
taagtattgt ggacgtaagt cattttcaaa tacaatcagt gaaccatcgc gagtaaagat 105840
aacatcatcg gttggatcag aatataattc aatagtctga acttcaaatt tttcagatgt 105900
taaattaatt ttagcgatat tccaataaat cacatcagct ggataattta tttcaccgat 105960
aacatagtat ttgtcgcgtc catcagaatt tgctaatttg ttaaaatcgt tgcctgtata 106020
tggctgaatg ttttcatttt ctgtaacatc gccagaagca aatggaccaa taataacttt 106080
accaattcct ttagaatctc ggtctgttga tactatgcga acgtcatata atacatcttc 106140
ttctaaacca gtatcaggat ttacaacctt tcgtccagaa ttaaatgaaa acgtattaga 106200
ttccatagaa cgatctttta tttgattatt gtatttaata cctgcttcag gcgttttata 106260
gaagttttgt acttcacgaa caatttgaat tgtcgctgat gaaccaatga tagaatgatc 106320
tgcatcatct acatatgtca acatcttaga tttagcgaaa gatgagttaa aaatttctac 106380
atcttcggta taataacgat caattttatc aattatttga ccttcgagcc actgttcgga 106440
ttcttgcagc ttatttaaag catatgtgac ttttaaatta gtcttaataa aaagataatt 106500
aggagaaata attgacggtg taataggagc taaattatag tctttgagat aatttttaat 106560
atcttcgcgc tgtacagtag ttaaatatag ccctgattta ggtttagcag caataaatgc 106620
ataaccaggt ttagtagaat cagtgaaagt ctgaactgct tgaataatag aaccaaatct 106680
ctctgaaacg aatgtatcat aatccgtcgc agttacgcag cgttgctggg tctcgcgttt 106740
aatagtaccc aattcacgaa tacgttcaat atcttctgga tcaccgccgc catctgcccc 106800
aacaaaatct gggtcatcgt ttggattttc attaatattg atgacagtta tatttgttaa 106860
```

```
tgtatctgca tatgaaaatc cgactgcgcc attcgcatct gcgccgttag tactgatgta 106920
ctcaataaca atcgtagagt tctgggtagg tttaagacct ccaatataat tagcggttaa 106980
tgctccttct gcggcattaa cagaaatctc accttcacca aaataaaatt cggtattccc 107040
atcaatagtt tcacgcatgt agtaaattgt cgatgtagaa ccagcatgaa ccattgactt 107100
tcttgtccag ttaatccatt ctgctccatc aacgtatagt ttaacttggt ttctatctat 107160
atttttgtca taaatgataa taggtgttaa tttatcgtaa atgatttcag ttcttactat 107220
acgtccctgg gctaatttta aacgcggaaa atattggtta tttttatcgc gaatagcaat 107280
aacatcttcg gtagatacaa agttgtaagg attaacggaa gtatcttttg catatgctaa 107340
aaagcgagta ccacgaggaa tagtaatgta atttctattc aatgcgtctg tacaagttag 107400
cataatttca gtttgagcag ctgattttga agtaggtaaa tatccattat cttgtgcagc 107460
ttgaactact gaactacgca aattagcagt acgcataaag ctttcgtaca aggcagcatt 107520
accaaactgc tgaatgtata atgtattata agccaaaagg tcacacagaa cgtttaatct 107580
tgagccttca aaatcataat ccaaaaattc attttggcca ttaagccatt caatgaggtt 107640
ttgttttatt tcagcaaatg tacccccgac gaatatctcg ggaatagcat ttgctgttct 107700
tgttaattga taatttacag ggtatttgc cattttaaat cctatttaat gaatacttta 107760
gatgatgcct gagccacagt atcaccgcat gatattggat cagccatttg aacagctttc 107820
tttccagtga catatacctt agaagttcta ggttgtgtca ctccgccatg tgtttcatat 107880
ggctttttaa tttctgtatg ttctgtaatt ggatcacctg ctacgagaac agcaattcct 107940
ccagtgaata ctttactttg cgtagcattc acaactgttg gaggccatgc ttcatggccg 108000
gaagtaacac acttatcata acttaatcct gacatttatg gcctctcata cacatagctt 108060
ctcaatttat tagcccaacg actccaattt ccaactatag tttttgtgta atttttaaca 108120
agagtttttc ttattggagc tggaggattc gttggttcag tagtatcaga agatgaccta 108180
gaattactgc cagaacctcc agattcacct tgttcttggt agtcatatat taatgttact 108240
tcgtaagtga atgtcttctg gaggttctga ggagctttcc ataaatacaa ttgggtatta 108300
gaatcagttg gaaggtcttc ccatgaagca gcagttttaa attcattatc taaacgatat 108360
ttcaacgcat catttccaaa tccaaacaca gattcatacg ttccatataa acgattttct 108420
tctactaaaa ccccaggagt ttcttcgtaa ctagttatat ttatagatac taacgtttca 108480
cctgtttcta attgagcggt aaaggtgacg tcgatagaag aaccttccat ggattctcct 108540
aaatcagcgc tcattggaag tatattagcc aatgtcaatc ctcgatccat caattgtgta 108600
ttgaccagat gaaatagaac tcatagatgc catttttttct gtccaatcac caccaacgtc 108660
ccagtcaact gtcccagcaa ctttccaaga aagatttcca tttactgtat tagtctgatt 108720
tccttcaact aaagtggtag catctccttt aactgtaatg tcagcattac cttcaactac 108780
aatagtaaca ttacctttaa ctaggatagt tccattacct tcaaccgtct tagtttcatc 108840
gccacgcaca aatattgtat tgcttccatc tatttggtgg agacgattat ccatgttgta 108900
ataaatttct gatccaccga cgttagtctt tttatcgccg gctaccaaaa aattaccatc 108960
agcatttgtt atatcataca aattatcaac agtttttctt gttcttcttc ctgacggtga 109020
tacttcctca tacgttccag tcggatgaac taatctatat cgttcttgcc caggggtatc 109080
atcaaattcc tgaatatgac cgctttcagt ttccattgtg tgaacatacg gatattcgcc 109140
tttatatgaa gaaacaggtt ctttaaataa aattctcgaa tcatttggaa taggaggatc 109200
agctgggtca gaagactttg ctacagtagc agccattgct gacaaagacc tagccggtgt 109260
```

```
tttcacttca ataccgtatg attccaaatt acctgtaaga ataatcatgg taacacgaga 109320
tgcacggcct tttgtttgtt gataccacaa tgaatcacga ccagctttat atgccttttc 109380
ccaatctcct gctaacatag cagttaacat tgtgttaaat ttagctacac caccaacacc 109440
catctgaaat gccatatttt ctaatgccat ttgacgagaa cgattaactg cttgccaaac 109500
tgggccaact ttagaatgcg atttaatgtc acgttgcata tcagccaaat cacgttcaaa 109560
taaagttacc gcttcttcca ttgtaataga acctggattt ccggtaattt cacgaccaac 109620
ttgttttgat aaaactttat taatttgagt catatcacga actggctgct tcatgataag 109680
atgaccaatg ccaattgtcg gatatccttc agtatcccaa taaactttta gtcttaatcc 109740
ttcatcacgg cgaagcattt cagccattga catatttgga ttatcatcag ttggaatttc 109800
tgatagcggt ctatcatcag gatttatcgc agtatctaga ttactgtctt ggataatatt 109860
agaagacgaa tcatatccta cttctccgcc ttggtttaat acgttagtat catttcctag 109920
acgtctagga tactgtccag tcgggtcaga aaatccttca agtctattag gcttttcgcg 109980
aactattcca ccatacgtgc caaggacaat tccgttagtt ttccatttgt ccaaaaaatg 110040
accataaact ctagttcctt ctaccggacc agtaactgag cctccaattc cagacattgc 110100
tgcagaagtt ataggttgaa taactgacat ccatggtaat ttatcagttg gaatacccat 110160
tacgtcgcct tgtgctcttt gaggtggatg cagaccaacc acacgaacac gaacacgacc 110220
taattttaat gggtccattc tatcttcaac aacaccaaca aaccaattaa ggttattact 110280
tatcatttcc ataagatttc tccattatac gtataaggtc gttcataaat gaattgatgt 110340
ctgattttgc tattattttt atttgacgaa gtttttcatt ttcaagaaca gcagcttcat 110400
acgtatcgac cgcagcaagt gctccttcat attgaggata ttttctagct ttatcacctt 110460
tgtcatacca aacatatgga ttatcatcat atgatattaa attataaaat ttttcaccgt 110520
tctcattcac atgatatact atttggtctc cacctacgtt tttatatttt tgtatagatg 110580
cttgataagc agcttcttgc gaagtaatcc atccataata cggatcataa ttatcattac 110640
acatcaataa aacccaatac aactgcggat ttccatatat agcatttgct aattcttccg 110700
ggcgtggtga acctttaata taataagtgc gtaagcggta tcctgcaaga gcacgtttga 110760
aatagtcttt atagtttcta aaaatatctg tcataggaat agtcggcgcg tttttattca 110820
ccgttttggc cgcatattca atcggatcaa aaaatgtaaa gagcatgggc cctcctgttt 110880
ataaatatat tatctattta taaggagaat ccaatggcat attctggaaa atgggttcct 110940
aaaaatatat caaaatatag aggtgaccct aaaaaaatta cgtatagatc aaattgggaa 111000
aaattctttt ttgaatggtt agataaaaat ccagaaatta ttgcatgggg tagtgaaaca 111060
gcagtaattc cttatttttg taatgcagaa gggaaaaaac gtagatactt catggatatt 111120
tggatgaaag attcttctgg acaagaattt tttattgaaa taaagcctaa aaaagaaaca 111180
caaccaccag ttaaaccagc acatctaaca accgcagcga agaaaagatt tatgaatgaa 111240
atttatacat attcagttaa tactgacaaa tggaaagcag ctcaagcttt agctgaaaag 111300
cgtggaataa aatttagaat tttaacagaa gatggattac gagctcttgg ctttaagggg 111360
gcataatggc tatttttcaa ataattaatg aaagcactcc ccaagttcca aaggttaagc 111420
aatcattaaa cgaaaagaaa tggattcaga taggtcttga atacaaaaag gccaaagcaa 111480
aaggaatgac aggaaagcaa tttgctgaag aaagaggaat caaatactct acgtttactt 111540
cagcaatgtc aaaatatgct tcaggaatta aaacagccga aaagattcaa aagcttgaat 111600
```

```
caaaaccaat gaataaactc aataagcaag aaagacaact gcttatgata aattcattca 111660
ggcaaacatt gcgtgataaa attcgtaatg aaggcgcagc aattaataat aaaaccagaa 111720
agtggtttgc tgaaactatt aagcaagtaa aaggacataa agttgttcgc ccgcagccgg 111780
gacgaatata tgcttttgct tatgatgcta aacacaagga aactcttcct tactgggata 111840
aatttccttt gataatttat cttggtttag gtaaacataa tttaatgtac ggattgaact 111900
tgcactatat tccacctaaa gctcgtcagc aatttctaga agagctttta aagcaatatt 111960
caaatacacc tactattact aataaaacga aattaaaaat tgattggagt caagtgaaag 112020
gatttagggg tgcagaccaa atgattaagg catatatacc cggtaatatt atgggtagcc 112080
ttgttgaaat cgccccgaaa gactgggcga acgttgtgtt aatgccgctt cagcagttcg 112140
tttcaaaagg aaaacgtttc tctgcaaaca aagtctggtc aaatatctaa ttctattatc 112200
ttccattctt ttctattgtt tgttctaatt ggaattgaat ggaagggact tagacccatt 112260
ataccaccaa catttataaa gcattatgag gaatatatgt cgcaagcact gcaacaaatt 112320
tttaaccaag caaatacaac taactttgta gtatcaatac cacatagtaa tactacatct 112380
gcttttactt taaatgctca gtcagttcct attccaggaa ttagaatacc tgttactgat 112440
accgtgactg ggccgtttgg actaggcaga gcacaacgtc caggagttac atttgagtac 112500
gatccactca tcgtgagatt tatagttgac gaagagctta agtcgtggat aggaatgtat 112560
gaatggatgt taggaactag taactatctt acaggcgaaa atactgccca aaaaacaggt 112620
cctgaataca ttacgcttta cattttagat aatagtaaaa ctgaaatcgt gatgtcaata 112680
aatttttata agccctgggt ttctgacctg tctgaagtag aatttagcta cacggaagat 112740
tcagacccag ccttagtatg cacagcaacg attccttata cgtattttca agtagaaaaa 112800
gatggcaaaa ttatagcaga agtttaatgc ttcagtttca tgtgttataa tcttaactaa 112860
atttgaggag aaacatatga aactaatctt tttaagtggt gtaaagcgta gtggaaaaga 112920
tactactgca gattttatca tgaataatta ttctgcagtt aaatatcaac ttgctggtcc 112980
tattaaagat gcattggctt atgcatgggg cgtatttgca gcaaacactg actatccttg 113040
cttaactcgt aaagagtttg aaggaattga ctatgatcgt gagactaatt taaatctgac 113100
taaattagaa gtaattacga ttatggaaca agcattttgc tatcttaata gtaaaagccc 113160
aattaaaggt gtgtttgttt ttgatgacga aggaaaagaa tcagttaatt tcgtagcatt 113220
taacaagatt gctgacgtta taaatactat tgaagatcaa tggtcagtcc gtcgtctgat 113280
gcaagcccta ggtacggatt tgattgttaa taacttcgac cgcatgtatt gggtaaaatt 113340
atttgcttta gattatcttg ataaatttaa ctcaggttat gattattata tcgttcctga 113400
tactcgtcaa gatcatgaaa tggatgcggc tagggcgatg ggtgctacag taattcatgt 113460
agttcgtcct ggtcaaaaat ccaatgatac tcatattaca gaagctggat tgccaattcg 113520
tgatggcgat ttagtaatta caaacgatgg ttctcttgaa gaactttttt ctaaaattaa 113580
aaatacacta aaggtactat aatgtctgaa caaactattg aacaaaaact gtctgctgaa 113640
atcgtagctc tgaaatctcg tattcttgat acgcaggacc aggcggctcg tctgatggaa 113700
gaatccaaaa ttctgcaagg aactttggct gaaattgctc gcgcagtagg tattactggc 113760
gatactatca aagttgaaga aatcgttgaa gctgtcaaga atcttactgc tgaatctact 113820
gatgaagaat aatggaattt aaagactttt caacgggtct ttatgtagca gctaagtttt 113880
cagaattaac acttgatgcg ctggaagaac tccagcgctc tttacgtgtt cctaatccag 113940
ttcctagaga aaaaaattcat tcgaccatat gttattcaag agtaaatgtt ccgtatgtta 114000
```

```
catcaagcgg aagttttgaa gtagcttctt ctggacattt agaagtatgg aaaacacaag 114060
atggatcgac tcttgtactt gtgctagatt ctgaatatct gcgctgtaga cacatgtatg 114120
cgcgggcact aggtgctaca catgattttg atgattacac accgcatata acattgtctt 114180
ataatgttgg acccttatca tttagcggtg atgtacaaat tccggtcgta ttagatcgtg 114240
aatacaaaga gcctcttaaa ctcgattggg cagatgattt aaaataattt cacaaagttg 114300
tttacatgct gatgaggtag tgatactatt atctcatcaa aattaattag gaaaataaaa 114360
tgaaaacttt caaagagttt gctacaaaaa ctactatcac tgaatcttct cacggtatgg 114420
aagtaaagct tggaatggct ttagctgaag ctgaacgtct tttctctcgt attaaagaac 114480
ttgcagctgc agtcgatcct tcatctttta aaggagatca aactaaagtt aaagcacttt 114540
tagcgttatg ctccgatgca ggagaaattg ctaaaaatgg ttctaagatg aagaaacgat 114600
tagaagattt aaaataattt cacaaagttg tttacatagg gttttagttg tgatactatt 114660
accctatcaa ctaccgagga gaataaaatg aaacgttgtg aattaattcg aaatgttgct 114720
attgcaattt ctgcttctgc ttttagtttt tcaatgtttg ttggatttat atgcggatta 114780
ttgactacag cagaaaatgt gttttcactt gtagtagcat tttaattgg tttaattgct 114840
atcgttatgg ataaaatttc taaaggtgaa tagaatgtac aaagtgtatg cggattatca 114900
ggctaatcca tctgaaaagc caggttgtca aattggatgg gctcatgata ctttgcttga 114960
agcagtagat gctgctcaaa aattgggata taaatatgta gagattgttc aacttccatc 115020
aggaacagtt attactctcg aagagttcaa taatattaaa ccaaactttt tactttttgc 115080
aggtgataat tattatcctc gcggtggata tgctgattta atcgcgaaag ccgctaccga 115140
agatgaactc cgtgatatta tcaaagaaaa tgaaaacaaa ccgatgtatg gttctaatcg 115200
ctttgattgg tggcaaatcg taaatgccca tactcatact attgttgatg aaggttgata 115260
atgattcttt atgcgaaagt atcgtccatt gaaaatggat ataaatatga tcaagacgcg 115320
gctaaagcct tgattgatga ttatggcatt ttaacatgtt ttgaagttga aaaggtttac 115380
attgaccgtt catcttcaca agttaaatta gtgaaggaag accgtaaatt taatacagta 115440
aattttgatt tctttattga aacagaaaaa ggtcctcttg aatatgatat tttcaagaat 115500
cctttgggtc ttgaatgcat cgtaaatatg tatcatcata aatggtaaat atgctttaag 115560
aattatttgt tattattaac tcatatcgca ctgattaata ccctctatca tcaagggttc 115620
ttgcttgaga gcctttgtta ataattggga atcatattat ggatactaaa ttagctgaaa 115680
tttttgaagg aaaacatcca aattttagta caggaaagct gaaagacaaa ataataaaag 115740
aaaatatttt tccatatgag tgtgcaattt gtaaaatttc aaaatggcaa aataagcata 115800
ttgttctgca attagaccat attgatggaa ataacaaaaa tcatcttaaa tcaaatttaa 115860
gattattatg tccaaactgt cattcgcaaa ctgatacttt tgctggtaaa aatattaaaa 115920
ataataaaaa gcgttataat gttagtgatg aagaaatttt aaacgcatta ttaaattcgg 115980
ctactatatc atctgcaatt acttcattag gtttaagtaa aggcggaaac tataaaagat 116040
tcattaaaat tgctaatgat aacaaattat atcatttact ggtaaatatt aatgaaaaga 116100
ttttaactga tgaaatttac gaagaattag ttaaaatcga ttattctaaa tttggatggg 116160
ttagtaaagc tgctaaaata ataggtataa gcccacaaaa agctagaaaa tggatagaac 116220
gaaagtgtcc agaattgata gaacagtctt tttcacgtaa taaataatat agcgcgagaa 116280
tggtcaaatt ggtaaaggca cagcacttaa aatgctgcgg aatgatttcc ttgtgggttc 116340
```

```
gagtcccact tctcgtacca aagtttgcgg atatcgtata atggcattac ctcagacttc 116400
caatctgatg atgtgagttc gattctcatt atccgctcca atttaattta ctccgtgtag 116460
ctcagtttgg tagagcgtct gctttgggag cagaatgtcg caggttcaaa tcctgccgcg 116520
gagactggag gcgtggcaga gtggtttaat gcaccggtct tgaaaaccgg cagtcgctcc 116580
ggcgactcat aggttcaaat cctatcgcct ccgtaatttc gctgatttag ctcagtaggt 116640
agagcacctc acttgtaatg aggacgtcgg cggttcgatt ccgtcaatca gcatatcaag 116700
gccctgtagc tggaaggttc aagcaagcga ctcataatcg ccagatggtg gttcaattcc 116760
acccagggcc atattttgag aacataaata ctcttagaaa taggagatat ttatgttcca 116820
ttacatttat aaaataacaa ataaaattaa taataaaatc tatataggcg ctcattctac 116880
cgaaaattta gatgatggat atatgggttc tggtaaatta ttaaaaagag cccaagataa 116940
gtatggtata gaaaattttt ctaaagaaat attagagttc tttgacgata aaacctctat 117000
gtttgagtca gaaaagaata ttgtgactga agagttttta aagcgccctg atgtttataa 117060
tttgaaatta ggtggtgaag gtggatggga ccatataaat attcctggga tgctaaacca 117120
gaagaaagac gctagtttaa aaggagctaa atcgtttaag tcacgtttta aaaatgatat 117180
tttacttcaa gaaaaatatc gtaaacatgg ttcaaatgta tttaaacgct tgtggtcaac 117240
tcctgaatac agggaaaaat ttttaaataa tagcagattt ttaaataagc atcatactcc 117300
tgaaactatt aataaaatga aagaatctca cgccagaaat aaacatcaac agggcgaaaa 117360
gaattcccaa tttggtatga tgtggattca ttcattagat gaaaaagttt ctaaacgtat 117420
taagaaaact gacccaattc cagaaggatg gtttaaaggt cgaaaaatga aattttaatt 117480
acgaggcata gctcaattgt atagagcaac ggacttctaa tccgtaggtt gaaggttaga 117540
atccttctgc ctcgaccaaa caagaagccg ggtcgctacc ggtaagtcgt cggactgatg 117600
ttccctgggt aaggactggc attaacaaat ctttacgatc tgttaatgtc cccttacatc 117660
acagcagaaa cggcgcacag aattatcgat tcgaggaaat atctttgccg taagccgagt 117720
agcgtttttg acggaacgtt cggatatggt cgagatatgg ccttttaaaa atattgagta 117780
gcgtcaactg cttaataacc gggttcgaat cccggcgttt cgtacaaaca cttgccttag 117840
caggtggaac cccgacaagg ttgccgcaag gcttagcccc gaccgaaagg ttggggcttt 117900
ttagtataaa tatagtagta tattaaatcc acgaattaaa acaggaaata agatgaaatc 117960
atatgctcaa tttttaaatg aagcggtgtt aaatgaagca tctagcaccg aaattcaagc 118020
tgtcgcaaaa gcagccattg cagcgggtaa atattcctat aaagatgctt ctgacgaatc 118080
acgattccaa tttgctcgcg acatgaaagc agaaggattt acgggaaatg cagttagtat 118140
ggcctggaaa agtttagttg ctactggcgc tgcttttgca aaggcttcgg gtaaacctgc 118200
tcctaaagca gatcctaaag ctgcacaaga aaaaaatatc gttaaaggaa ttatctctaa 118260
atatgaagct atccttaaag agcttttagt aatcaaaacc gaaggccaaa agctagcccg 118320
tgcttatagt ttcaaagata atccgcatgt tcactctctt gagtatgttg aagacatcca 118380
aaaaattatt aaagaccgca tttggtctgc taaacagatc aaataacatt cttaacccca 118440
gccgaaaggt tggggctttt tggtatctag gcctttctgg acctctctag tcatcatttg 118500
gtttataccc tttataaatat attatcctat cttttaattg cccctccctg ccctagaatt 118560
ccctaaaact ttttaaaaaa tttttcacaa aacggtttac atctctgttc ttccatggta 118620
ctatacaact atcaactact gatacagaaa acaacttgga gaatgaaatg gataattacg 118680
gcgaactgtt caacttcttt atgaaatgcg tttcagaaga tttcggtcgt acagtgaatg 118740
```

atattaaagt tatcggtcct gatcatccga tgtttgaaac ttacgcagta atgggtaatg 118800
aagatggtca gtggtatact gtaaaagttg tgattaacat gttcactgct gaaggttatg 118860
ttaaactgtc ttctaaagtt taccatgata acgacgaaat cgcagaagaa tatttcaata 118920
atatgaaata agtttacaca ggctcatgat tgagatatta tgagcctgta acttgaggag 118980
aacataatga atattgaaga taaagaaatg cgagagttat ataattcatt aacacccgaa 119040
caacaaaaag ctgccaaaga attagagaaa gctcttagtt taagcttgac aaaaactgat 119100
tgggccgccg tgtatgaaga aaaaatgagg tcggaaaatg aagctatcga gagaaatgaa 119160
tggattgtgg ataccaagat tggagctgat ggttgttctg ttgaggtgtc agctgtagtt 119220
aaaggtactc atggcgaaaa atcatggggt tggcataatg aggcaaacaa atatattgtt 119280
ctctcaacat caaaaactta tggtcaaaag gttcctgtat ccaaagctat tattaagcaa 119340
gctcaatggg aagccaatga aatctgtctc gcaaaaatga aataacatgt ttacatttct 119400
caaataacag gatataattc tacacggatt ttaaatctta atcaacctaa ggaaatacta 119460
tgaacacact gaagaaaatt gttgagttta ttcgcactaa acttggttct gctatggcta 119520
aaaatttatc tgttgaagaa cagtatactg ctgcggcagc aaaactactt gataaaatta 119580
aagatctaaa aactgcttct gttaaatcta ttaatgaaga aaaacgtatt cgtgaactta 119640
ttgtcgaaaa gaatcgacag gctgaatcaa aagagcgtga aattcgtaaa cttctttccg 119700
aaggtcaaga tgtaacaatg catgctaaac tcggtttact atatcgtcga acagctgagc 119760
agttgactac taaagctgac ggttatgctg aaatgcgaat tgaaatcgcc aagaaagtag 119820
ttgagttaga tgatgctcgc caagaacttg cagttaaatt ggaatatatc cgtgaaactc 119880
gtgcagcaaa tgcccttgga attagtactg ccgatgatgt agttgaaatt gcagcactga 119940
ctaaggttga tattgaagat actcttgctc gagttgaaac ctttaacggt aatatttctg 120000
gggttgaaac tacctctgcc gatgttcagg aatacattaa ttctctgaaa taatgataag 120060
gggcttcggc ccctattact tggagtaaat aggaatgaaa atgcaaagtg atttcaattc 120120
aatgtttgaa gagttccaaa gacaggttga tgttccagac caattactaa atgctcttaa 120180
acgtatggca gaaggacgta attattattg gggtcttca tatgaaactg atgaaagtct 120240
ttctggattt tataaaggta aaaagtcttt aatacgtcct ggaatactta ttaacagtat 120300
tgaatcaatt catttattga cgtgtgattt tgatgttgaa tttactgatt ttgtttctcc 120360
tgaatggaca gtatgttatt taaacgacga ttatgattat ctcggcattt atagtttaag 120420
tgacgcatgg tttaaacgta acttacaaaa gtcaaattta ttctatattg atactacagt 120480
aaaatttcag ggaaagaaat atttctttac tcttatagtt gattctgaaa cgaagcatga 120540
aaataaacgt attcttagta aaaagaatat cttgactatt attgatgatc tttttgataa 120600
attcgtagaa aatcctaatt ttgaaagtga tttattatta gaaaaatttg ttaaggaatg 120660
tagagaatat gtcaaagcca tcactatacc ttccaagtaa acctttgaag tatgaactaa 120720
agcgccagat aatttctacc gatgtattaa taggtcctgt tatactcata tcatttgtaa 120780
ttctattgat tattggaggt gttttagatg ttatgactga tattgattct ggcgaaatac 120840
ttgtgttaat gctaattctt ccattaatag ttccactttt attagtacct ataaattggg 120900
taggatactg gtatcaagga agacattatc gtaaacgcgt acgtgattgg aaagcacagt 120960
gtaaaaagat taaaaaggaa catcagctta aacttgctgc atatgaattt gatgaaatta 121020
tgaaatttgt taaggaatca cgatgcaaaa gccaaaacta aataaagtca aatattcgtt 121080

```
ttctgagtca tttttaattt ttgctgtggc gttggctgca gctcttgcgg gtagtctttt 121140
tggattgtta attgactgtc ttattttaaa catcgacggc acagtaaata taacagaagt 121200
ttggagtgag ctttgttata ctaaaattat ttcattattt tcattctttg gtatcatttt 121260
atattttcat tatgataatt ttaaaataaa ttggcaaaga aaaaaggatt acaaaataca 121320
attaaaggaa tataatagct acatgtctta tattgaaaaa gaatcaatgg aagagtttgt 121380
gagtgattgc aggaaaatca gatgatttta aaaactcgct ggtatgactt agacgatggg 121440
gatgatggca ttccagttga tagagttgac tggaatggtt gttctgaaga tacaaagaaa 121500
cgattaatta gggagtttag aatgggatat caagcagcta agccatttac tgtaacagat 121560
gataaattcg tgtgtattca aaatggtcgc gctaagttaa cgaatgctga ttggttcaca 121620
gataagaagg ttcttctgtg gtatatcatt agtcttccta tatcatcgtt agtattttac 121680
tttttataa aaaatccaat ggacagaata ggagattggg ttcttttaac tatacttgtt 121740
aatattttta cagcagcagt attatcagga atatggcgca tgttcattga aatgccatgg 121800
cggttacgta ggcagcaaaa gatttttgat gaaaagaaat atactcaaaa tttaaataac 121860
tttatcactg aatgcaggaa attaaaatga aaacattatc agctggtatt atctttatga 121920
cagaagataa agatttattt atgggtcggg ttactggttc tcgtaagcct ggaatgatgg 121980
cacatcgctg ggatattcca aagggacgtg tagaaagttc tgatttgaat gcactggaag 122040
ctgcaaaaag agaatgctta gaagagaccg gttttagcaa ttataatcca gaccttctag 122100
aagacctagg tgtatttaaa tattctagta ataaagactt acagttattt tattatacga 122160
ttccagtaga gcatgagatg ttcagaaatt gccattgcga gtcttatttt gaaaataaag 122220
atggcgttat gattccagag atggacgctt ttgctcttat tcctcgtacc cagtggcaat 122280
atgtgatggg cccttcactt taccgaataa tgaacaacct cttttaattt ataaatacct 122340
tctataaata cttaggaggt attatgaata tatttgaaat gttacgtata gatgaaggtc 122400
ttagacttaa aatctataaa gacacagaag gttattacac tattggcatt ggtcatttgc 122460
ttactaaaag tccatcacta agcgttgcta aatctgaatt agataaagct attgggcgta 122520
attgcaatgg tgtaattaca aaagacgagg ctgaaaaact ctttaatcag gatgtcgatg 122580
ctgctgttcg cggaattctg agaaatgcta aattaaaacc agtttatgat tctcttgatg 122640
ctgttcgccg ctgtgcattg attaacatgg tcttccaaat gggggaaacc ggcgtagcag 122700
gatttactaa ttctttgcgc atgctccagc aaaaacgctg ggatgaagca gcagttaact 122760
tagctaaaag tagatggtat aatcaaacac ctaaccgtgc aaaacgagtt attgcaacgt 122820
ttagaaccgg aacttgggac gcgtataaaa atctataaag ttgtttactt tctcctagaa 122880
ttgtgatagt atattcacag ttacttggag ggataaaatg actcgtatta atttgacttt 122940
agtatctgaa cttgctgatc aacatttaat cgcagaatac cgtgaactgc cgcgtgtttt 123000
tggtatagtt cgtaaacatg ttgcaaatgg taagcgggtt aaagatttta aaatatcttc 123060
cgagtttatt ttaggttctg gtcatgtcac gttcttttac gataagttag aatttttgcg 123120
aaagcgtcaa tcagacatta taacggaatg cttaaaacgt gggtttagta taaaagatac 123180
tgaagttcct gacatcagcg atattccagt agaatggaaa aatgattata atccatgcaa 123240
atcagctatt aaattgagtc aacaacgact cgatgaaaaa attttaatga agccacactg 123300
gtataaatac tacggtaaaa atatttacat ttaaaggaaa cacatgaaaa catatcaaga 123360
atttatcact gaagcagcta ttaattctca aattattgct gaatctttta ctgatctttt 123420
gaaatttaaa aaaggtcaaa agatcactgc tgtattagat gatggtacag aagttgagat 123480
```

ggatgtacag ggatataatt atgcagtaga tggaaaactg tataataaat ctcacgctaa 123540
atttgattca tttgacgact ttgttaatac agttgaagat gaaaaaactc gtagatcaat 123600
ttcaactggc gatgctaagg ttcttatggc gcacggtcat gaacgtatcc gcgccaaaca 123660
gaataaaatg ggtgaagata atttcgcatt agttggttat caatctggta aacaaactta 123720
tggttatcag cgtactgcta ccatgtataa caaaaatggt aaaatagctt tcgtgaatag 123780
caaaggttct attcagtacg tcaaatcatt caaataagca aataagaaat atgggaacaa 123840
gctggacctc atgattctat gagggattcc cgccaacctg taataaggtc gagcccaagt 123900
gcggtaatgg gtaaatacag aaatggacaa ttcatgcgcc atggaatggc ccaaatttag 123960
agagaataaa atgagaacat ttttaactgg tccttatcta tccctgatga atgcttttac 124020
acaccattct gatgctagag tagaagaaat ttgcaatagt ggattttatg tacctgattc 124080
gtcgcattta tttaaagaat attgtacact tcgactagat ggtggacgtc aatctggtaa 124140
atcaactgct gtgactaact ttgctgctaa ttggctgtat gacggtggaa cagttattgt 124200
tctttctaat acttcagctt acgctaaaat ttctgcaggc cgcattaaaa aagaattttc 124260
tcgttattct agtgatgata ttcgattccg cttatttact gattctgtcc gtagttttat 124320
cggtaataaa ggaagcaagt tcagaggttt atcgctttcg cgaattttgt atataattga 124380
tgagcctgtt aaatctcctg atatggataa aatttacgat attcatattg aaactgtgca 124440
acactgttgt aatagtaaat gttgcattgg tggtattact cgtccgcagt ttttcgtaat 124500
cggaatgcaa tgatgacaga cacacagctt ttcgaatatc tttatttttc gccaaaaact 124560
attaaaaata aattggtgaa tcattttgaa attttggcaa ataacaacgt cttgagcgaa 124620
ttttatccta agcaatacaa attacaaaaa ggtgtattca aaggatgcag agttttgtgc 124680
actgctccta atgcaagatt aatgaataaa attccatatt ttaccatgga atttattgat 124740
ggacctttta aaggactaat cacccaaagt ttaatggcat atgattctga gccattttta 124800
attaaagaac agtcttggat aaatttattt tctaattgag gttatatgaa agcatatcaa 124860
attcttgaag gcacacataa aggtactatt tattttgaag atggtattca agcacgaatt 124920
attgtttcta aaacctttaa agaggactct tttgtagacc cagaaatttt ctacggtttg 124980
cacgcccgtg aaattgaaat tgaaccacag cctacagtta aaattgaagg tggtcaacac 125040
ctgaacgtta acgttctgcg tcgtgaaact ctggaagatg cagttaagca tccggaaaaa 125100
tacccgcagc tgaccatccg tgtatccggt tatgcagttc gctttaactc tctgactccg 125160
gaacagcagc gcgacgttat cgctcgtacc tttactgaga gcttgtaatg gcaaagataa 125220
ttattgaagg ttctaaagat gtgttaaatg ctttcgccga gtggtttagt aattcaggcg 125280
aacagcaatt taatgaagcg tggaccatgg gtgatattga tggaatttat cctacgacag 125340
aaatttctgt tcaaggatat ggcattcatg aacctattcg tttagttgaa tatgatttat 125400
gtactggtga ggaagtcaaa tatgattgaa gatattaaag gttataagcc acatactgaa 125460
gagaaaatcg gtaaagtgaa tgctatcaaa gatgctgaag ttcgtttagg acttatcttt 125520
gacgctttat atgacgaatt ctgggaagca ctagataatt gtgaagactg tgaattcgcg 125580
aagaattatg ctgaaagcct cgatcagtta actattgcta aaacgaaact caaagaagcc 125640
agtatgtggg cttgtcgtgc tgtgttccaa ccagaggaaa aatattaatg gctcaattaa 125700
gcgcagggtt tggttatgag tattatactg cccctcgtcg tgtatctgtt gctcctaaga 125760
aaattcaaag tcttgatgac ttccaggaag tagtccgtaa agctttccag gactatgcgc 125820

```
gttatcttaa agaagattca caggactgtc tcgaagaaga tgaaattgct tactatgagc 125880
aacgtcttga acagcttaaa aacctacatg aggttcgtgc agaagttaca aagtctatga 125940
ataaattgat tagatttaaa gaataactgt ttacttttcc tcttgactat ggtataattt 126000
ttctatcagt taagaggaga ataacatgac tatcaacaca gaagttttta tccgtcgaaa 126060
taaactccgt cgtcactttg agtcggagtt tcgtcaaatt aacaatgaga ttcgtgaggc 126120
atcaaaagca gcaggagtct catcgtttca tctaaaatat tctcagcatc ttcttgatcg 126180
tgcaattcag cgggagattg atgagacata tgtttttgaa ttattccaca aaataaaaga 126240
ccatgtttta gaagttaatg aattcctgag tatgcctcca cgccctgaca ttgacgagga 126300
ttttattgat ggggttgaat atcgtcctgg gcgtttagaa atcactgatg gaaatctttg 126360
gcttggattt acagtttgta aacctaatgc gaagttcaaa gacccgtcac ttcagtgcag 126420
gatggcaatt atcaacagtc gtcgtttacc aggaaaggct tctaaagcag taattaaaac 126480
tcaatgaggt aagcatgaga aaagcactac tcgctggtct attggccatt tcaatgatgg 126540
cacatagctc cgagcatact ttcagtaatg tccaactcga taacatgcgt tacgcgtatc 126600
aattcgggga acagttttct aaggatggaa aatataaaac acataaaaat atccacaaga 126660
gcggattagg tcatataatg gctgctattt tatggcaaga aagctctggc ggagttaatt 126720
taaaatctaa accaaagcat cacgcttatg gaatgttcca aaattatttg cctactatgc 126780
gagcaagagt taaggaactt ggttataata tgaccgatgc tgaaataaaa agaatgttga 126840
ataaacaatc caattcagct tcctgggcgt acattgaact ttcttattgg ttaaatatac 126900
ataagggcga tataagaaaa gcaatatcct cttataattc gggatggaat gttaaagcag 126960
gttctaaata tgcttctgaa gtcctagaaa aggctaatta ccttaaaaat aataaacttt 127020
tggaaatagt aaatgactaa aattttggtt ttatgtatag gattaatttc attttctgct 127080
tctgcgtcag cagatacatc atatactgaa attagagaat atgtaaaccg cactgcggca 127140
gattattgtg ggaaaaataa agcatgccaa gctgaatttg cacagaaatt aatatatgca 127200
tataaagacg gagaaagaga taaatcaagc agatacaaaa acgatacatt attaaaacga 127260
tatgctaaaa agtggaatac cttagaatgc tcagttgcgg aggagaaaga taaagccgct 127320
tgtcattcaa tggttgaccg tttggtagat tcttataatc gaggattgag tactagatga 127380
ttgtaaaata tatcaagggc gatattgtcg cccttttcgc tgaaggtaaa aatattgcgc 127440
atggatgcaa ttgttttcac gcgatgaaag ctggagtcgc aggtcaatta actaaagctt 127500
tccctaaaat tctagaagct gataaattac agactgaatg ggtgatgata actaaactcg 127560
gttcttactc agtctatgaa aagtacttta ggactcataa agcttactgc tttaatcttt 127620
atactcaatt tcaaccaggg ccaaattttg agtattccgc tttaatgaat tgtatgttag 127680
aattaaatga gtttggtgaa aataaactga ttaaacctac aatctatatg cctaggattg 127740
gtgcaggcat aggtaaaggg aactgggata ttattgaaga tattttagat acatattcct 127800
ctaaattaga aattgtgatt gttgattggg aaccgttatt atgaatatac attatccaca 127860
tccatatgac ccaaagaata aggcagtaat tattcgtcaa tgggaacgca tttgccgtac 127920
taaatgtcca attaatagtc cacatgatgt agataaagac tacattggaa cattcgttga 127980
atataccttt attgataaga aaggtcgtaa acaacatgta gaagaatact gcttaaaggt 128040
tacatggtta tgagccaaac tagtattctt aaaaatgccc actgtgaaaa gtgtaagtgg 128100
cctgttgttt ttgctttatg taatgatgaa atggcttgtg atttcgatta ttggtgctat 128160
tgttctaata aaggatgcat caatcataaa ggtgaaggat tttattcagg attttatcct 128220
```

```
tatcctgatt tcgttaaaga aggtaaacca aaatgaatag ttttgagtta caatatgaag 128280
tgttacgtga gcttgataat ttaattgaac tcgctgtcaa taaaggtttt gccattggaa 128340
tcggtcaaaa agatactgat catttaacta cggaaatatt taagcaaaag cgaattattt 128400
taaaactcct ggaaaatata tgagtctgag taaagaacaa aaagataaat tgtttgagct 128460
tatccatgaa cttctagatg agcatgcaga agcaaacacc ttttatgatg aatacggccc 128520
gctatctccc gaacaacaag aagaatttgc tgaccggttt gataagaaag aaaatgaatt 128580
aatagcttat gtgaatacgc tttaagaagg tgatatggcg agtttaattt ttacttatgc 128640
agcaatgaat gctggaaaat ctgcttctct tttgactgct gcgcataatt ataaagaacg 128700
cggaatgggt gtattagttc ttaaacctgc tattgatact cgcgattctg tctgtgaagt 128760
cgtttctcgc attggaatta aacaggaagc gaatattatt acggatgata tggatatttt 128820
tgagttctat aaatgggctg aagcacaaaa agatattcat tgtgtatttg tagatgaagc 128880
tcagttttta aaaactgaac aggtgcatca attaagccga attgttgata catataatgt 128940
tcctgttatg gcttatggac taaggactga tttcgctgga aaattatttg aaggttctaa 129000
agaacttttg gcgattgcag ataaacttat tgaactaaaa gcagtttgtc attgtggtaa 129060
aaaagcgatt atgacagctc gattaatgga agatggaacg ccagttaaag aaggtaatca 129120
aatctgtatt ggtgatgaaa tttatgtttc tttgtgtaga aaacattgga atgaattaac 129180
taaaaagctc ggttagtgca aaagttataa ataggtttat ctaactaaag ggtatatat 129240
gctacaatta actgaaaagc aacttcgcaa tcttactgtt cttcaattag atgaaattcg 129300
tagggaagtt ggaaatatca tttcagcttt gcgtcgagaa gtatcactca accaatctcc 129360
ggcagactat actagattgc gaaattttga aaaataccttt gataaagtta aggccgtgca 129420
tcggcataaa gtaaatacag gacaaaaatg ataggaggcc tttatggcct taaaagcaac 129480
ggcactattt gccatgctag gattagcgtt tgctttgtct ccaccaattg aagcgaatgt 129540
cgatcctcat tttgataaat ttatggaatc tggtattaga cacgtttata tgctttttga 129600
aaataaaagc gtagaatcat ctgaacagtt ctatagtttt atgcgaacga cttataaaaa 129660
tgacccgtgc tcttccgatt tcgaatgtat agagcgaggc gcggagatgg cacaatcata 129720
cgctagaatt atgaacatta aattggagac tgaatgaaat tcagcgactt ttcacaaagt 129780
ggaaaacctt caaaggcaga tgaatactta ggtttattaa tggctgcaca agcttatttt 129840
cattctgcgc attttgaaac taaaagttat gctagacaca aagcatacga ttttattttc 129900
tctgagttgc cagatttgat tgataaattt ggtgagcaat atttggggta ttctggtaga 129960
aaatacacac cttcaattcc agatgccagt aaacttccta ccgacacaat taaaatgatt 130020
gatcacatac tagaccaatc taacagcatt tataaagaaa tgcctccagc cattcaaagc 130080
acgatagatg atattactgg gatgttttat caaagtaagt atcttctttc cctcgaataa 130140
cattagtctc cttcgggaga cttttttcat tttaccggtt tactttccat ttgagctgtg 130200
atactataca accatcggat aaagaggaga acatcatgaa aattgaagca ctcaatcaag 130260
aaggaaatat ctacgtcatc attaatggtg attttttcgt caacatggat gacgttacta 130320
gtgaagaact tgtagaactt cttaagaaac gttatgatat gtgtgatgaa gctgcaactc 130380
acatggcgtg tgcaatattc tctctttcat atgtggtgga ataatgatta gcattgaaca 130440
agcagataaa attaaagaat tggtagcttt aattcgcaaa gcagatgagg aacttagtga 130500
ctttgcttgg ttttcgtcgg gcattgcaaa taaaggtgct gaagaacttg aagctaaagt 130560
```

```
tgataatgct gtagaagcgt tagatatgtt tcttgatgaa attatcgatc ataatacgag 130620
agtttaagta tgctaacacg tgaacagttt gaaaaaatca ttaaattagc acgtgatatt 130680
gaaatagatt cataccaatt ggcagttgag cattgtgaag gatattcata cgatggtata 130740
gaaacagcta aaaaggattt ggataaatct aaagctaagt tagttcaata tcttgaaatg 130800
attaggtgga ataatgaaaa ctgaaaagca gatgttttta atgaagctaa ttgaagaata 130860
tgctaatgca gtttctgact atgaatgttc ttctcgtgaa agaggtacag ctttcgctaa 130920
agaagaattg aaaatcatgg ttgatgctca tacaaagctt cagaatttta tcgaaaacgt 130980
catttaatgg tttacaagtt ggcaaggtta tggtatagta atcttgtcaa ctgccaggga 131040
gaagagaatg aaagttttgt ttgttgtgta tgtgatgatt caatataatt acccgatgtt 131100
tacttataat ctggtgaaca acattattga tattattcaa aggagtatgt aattgtgagt 131160
gagtcgaaga gaatcaatat gaaacgatta gtattagaag ttagtccgct ttttggtgaa 131220
ttggctatag aaaaagtaaa taacatgtat cgtttgacgc aagaagacga tatgctatat 131280
tttacgccta gtgaaatcat tcatttaatc aaaattgaat atccttatac tgataaaata 131340
gtaagcatca atgatgagca caaaattcat ttttattctt catgcctagg atttaatatt 131400
aaaagtgagt caatgtgttt atcagttatc cattgggata gttttatagc taagattaaa 131460
tatttttatt attctaatga aagaaaacat agtttaaaat ggctcaaaaa ttgcaatgct 131520
attattacta actcttacaa tcagaatgat gaaactcttt taaatgtatc aaaatgttat 131580
gaagaaggag atgtcttaac tattcgtcaa attgatgatt ttcgagcaca tattgtcaca 131640
tttaccaaag acgaagctat tgcgctaaag acttatcttg attctgtcat tccaactatg 131700
atttcaaagt gaggaaatat gtttatttca agtggaagtg gtttaattcg tgttgaattt 131760
aaaaatgaca tcttccttag tcaaggagat gatattatta aaatgagtta tgacgaaatc 131820
aagaaaattt gtcatgctct tgaaagccgt ggaaacgtaa atgctgttat tgatattggc 131880
gatttatggg tgacacttta tgaagtatcc gaaggattta acattgaaga tgaaaataac 131940
attttagcta ttgataaaag aactgatttg tttgatgtat taaaagccta tgagcagtca 132000
aatggcggaa gaaaagctgt attgatttat caaaaaccgc attcatgtgg aactgcttca 132060
atcatttcaa atattgaagg cgaagttgat acttatatgt gtgttttaaa agctggtggt 132120
gaccgtcatc cggattttat ttctattcgt caaaacaatg gagaaatttc attatcaaaa 132180
tcagaagctg aagctatgat taagtattta acaaccgtta cgccttcaat gaaaggataa 132240
ttatgattat taatgaaaac tcttggcact ataaattatt caaattgttt aacgatgaat 132300
ggcaacgacc taagacacta tgcgcatatt tttggtctat tgccattcct acatttttcg 132360
tttctatttt tgggtgtgct atactcgtag ggctaacaat tatttgtgca gaaagcctac 132420
aacgttggct tattttcggt agtttatgga ctcttcttcc atcggcattt atacttgcgc 132480
ttttggttgt tttacttatt atcggttcat ttgttattcc tgcacatttg cgtgaaaaat 132540
ataaagatta taaatggaaa aaggattatg ctttacacgt agaaaatatt gatagggcgt 132600
ataaaggttt acctcctatt caacccaaga aatcgattat tgttgaattt ttaaaagctc 132660
gtaaatctaa agtatgtcct gttattgaat ataaggctga atgatgaaaa cagtaatgaa 132720
aagctatttt ggtagtcatc tttatggaac ttctacccca gaatctgatg tagattttaa 132780
agaaatcttt gttcctcctg ctcgcgatat tcttatcgga aatgtcaaag agcacatgag 132840
taaaaacact aacaacacat catctaaaaa cactaaagat gatattgacc atgaactata 132900
cagtcttaaa tatttcttta aattagcagc agatggtgaa actgtagcat tggatatgct 132960
```

```
tcacactcca cctgaactag tggttaaatc tgatttgcct gatgtgtgga agtttattca 133020
agacaaccgt tctcgttttt atacgactaa catgaaatcc tatttaggat atgtccgcaa 133080
gcaagcttct aaatacggtg tcaagggttc tcgtttggct gcattacgtg atgtattgaa 133140
agtagttaat caaatccccg agcaatgggt tgattaccaa gaagatggtt ctattaagca 133200
gcgtcgcact aaagttgaag atattaagca tcgtcttcca gaaaacgaat tctgtgaatg 133260
ggtgttccat aatcatgaga aaacaggccc acagacgttt tacacagtgt tgggtcgtaa 133320
atatcagaca actctttctc ttattgagct taagcagtca ctgaacaaat tagatgctga 133380
atatggtgaa cgtgctcgta aggctgaagc caatgaaggc attgactgga aagctctgag 133440
ccatgcttgc cgtggtggac ttcaactatt ggaaatttac aaaactggtg acttgattta 133500
tccacttcaa gatgctccat ttattctcga cgtgaagttg ggtaaacatc catttaaaac 133560
cgttcaagag tttttggaag atgtggtcga tcaagtagaa gcagcatcta ctgaagcttc 133620
taagaacggt atgcagcaaa aagtagacat gagtttctgg gatgacttcc ttgagaaggt 133680
ctatcttgaa aaccatcgaa gttattataa atgataggga gccttcgggc tccctttta 133740
tttcaaattt tttttttca caaaactgtt tacaagcata aagctttatg gtactataca 133800
actatcaact actgatacag atttggagaa taaaatgaaa actgtaacta tcaataaggg 133860
tatctacttc ggtaaagaaa tctctggaac ttttgagctc ttaggtgaat ggttcccaga 133920
taatgctccg gtagatgcac aaggagatgg taaagttttt gttgaaattg acggtaagcg 133980
tcgcggtgtt tgggtttaca aatcagacat ttcatatgat ggtgtaaaag ttgaagaagt 134040
taaagaatca tatgaagata tgaaaacccg cattaataaa agatttaatg ttatgggaat 134100
gatgacgaat ggtattatta acggaaacat tcgttcatta attatctctg gtgcggcggg 134160
tattggtaaa acgtattctt tagataaagc tttaaataaa gcaaatgata atggatacat 134220
tgaatataaa agcattaacg gtaaaatctc tggtatcggt ctttatgaac agctctggaa 134280
taatcgtgaa gagaattctg tccttttgat tgatgatgtg gatgttttct ctgatatgga 134340
cattcttaat cttctgaaag ctgctctgga cactggagag acccgtaaag tctgctggag 134400
caccgcatct tcttacttag aagaaaaagg cattgagcgt gagtttgaat ttaaaggaac 134460
gattgttttt atcacaaacg ttgacattga ccgcgaatta gaccgtggta ctaaacttgc 134520
tccacattta caagcattag tgtcccgctc agtttattta gatttgggtg ttcacactaa 134580
tgaagaaatt atggtcaggg ttgaagatgt tattctttca accgacatga tgcaaaagcg 134640
tggtctttct gatgaagaaa cttataaagc attatcatgg atgaaagtta atgttaatcg 134700
tttacgcaat gtttcactgc gtactgctct ttatcttgct gactttatta tgaccgacaa 134760
aaacggttgg caagaaatcg ctgaggttac tcttctgaaa taaattcata agaggccttc 134820
taagacaaaa aggcagttca gaaatagatt atatggactg ccattaaaaa gatgactaga 134880
attaaactgg taaatggagg taatgatgtt atactcaaag gctcgtgaaa tttacgaaac 134940
taagattaaa gaagctgtac ttcaattcgc aacaacgatg cgatggacaa atgattggga 135000
gtattcaaaa aatcataaga agcccatggt gacaagaaag gctcatatgt tagtgttaat 135060
agaccgtgag cagattaaag cccgagaagc cctccagaat cataaaaagg ctgcctttga 135120
atggtttatg gataacactg ctcctgagac taagaaagca gtgagcgcat ggttcagtgg 135180
aaaaaattgt gaaagaagtt tcttttagtg gtttacaaga ccgttcctct gtggtactat 135240
acaactatca actacggagg aacataaaat gaacgctaaa gatattttca acctggtaaa 135300
```

```
ttacaacgat ggtaaattta aatctgaagc acaaagcaag ttctttaatg acatctcaat 135360
cggaggtgaa atcacggttg atggaggaca aatttacaaa tcccgttgga attggatcgt 135420
tattatcgat gagatcggta ttgtagaaat ttacaagaat acgaataaaa atcgtacatt 135480
acactggtct cgtgatacta acgaacagta caaaaaggat aaagcatcta aattatctcg 135540
tgtaactcaa gaagatattg agtttatcaa gaaagatatt ttaatgtatg ataacttaat 135600
tgctgaagag caagctgtta ttgataaatt tgatgagatt aaagcttctc gtgaaattcc 135660
tgattttatg aaagaatcag taaatgaacg atacactctc atttcagagc gtattgaaac 135720
ttacaaaaag caaagagctg aacgccagaa cactcttcgg aaatttgaag aacggttaaa 135780
gacggtactc gcataaccgc tttataccaa ggatggtata atggttctaa gcccttttaa 135840
ctgagattat tatgaaacag ttgataatta aaagattgaa tttattgata tgttgtttat 135900
gtgtagtagt tgcatatggt tattacgcaa ttaatgatta tatgcattat aaagattatg 135960
atgttactgt agttaatacc tttacaggaa ctcaaggaaa ggggtctagt ttatcgttta 136020
ttgctgtata tgaactcaaa gacggttata gatttagtga atatatttcc ccagagatgt 136080
attcttcaat agaaaaaggt gataatatta ctgtaagttt acgtcctttc gacgtaaaac 136140
agacattgtt tgataatatt gtttggttct ttggaatggt attagttcaa tctgtgtgtg 136200
gtgcttatat agtctgttct atcttattct gtatatttag taaaattgaa attgagtgag 136260
gaaaatatgt cagtagcaat taataatgtc aatgcagtaa ttaaatcttt agttaataaa 136320
aaatcaaatg aatggactgt acttcaacgc gacgagtcag ataaattttt tcataaattt 136380
aacccagtac taaatttaaa tgttatcgat aaagatgttc acgccgaaat tttagataag 136440
tttaaagttg atattggatt tggattagaa aaacatttac aacgaacaaa cgggtctgga 136500
atgcttttat ctaatcgcat catgaaagcc cttaataaaa ttggagcgtt gtctcgcatt 136560
aacgcgagtg aaattcttcg caattataat aaaggatatg acctttatgg tcgactaatg 136620
ccgaaattat cattcgatca aatgattgcg gatttgtggg aaaatcaacg acgattatta 136680
gcattaggcg ctagattagc taaaggtcta gataaacaaa tgatttttaa gaccaataat 136740
acagaagacc ttaaatgctt taaatttagt atgcgtggag atgattatta catcagagct 136800
cactctacag attatgttaa tatggggcat catctctgtt tagcttttga aattttaaaa 136860
gaagctggaa cattagaata tgtgtctggt gctaaatgtc cgattggttc aagttgtatt 136920
ttaatttatc gcccggatga atccagttca actaaattgc ctacaaaacc tgtaccagtt 136980
cgtagtaacg aaaaacattc tgaacaaatt gattatttta ataagcaaat tgaagagctg 137040
aatatttcta ttcaacaata tgacgatgaa attttcagac tatctggatt gagtagtaaa 137100
gctaaatctg aacgtgaaaa attaattaaa attgttgatt tacttaaatc ttaaggaaca 137160
ccatgaaaac tcgttctcaa attgaagata tggttcgtaa tgccagctat acccgtgatg 137220
ttatgacatt tttgtgtgaa aataatttag accctgataa agttaatcgt gttattcatc 137280
actttaagta tacgaatagc agtgaatggg tgcgtaattt tagcgaagca gggtatatta 137340
cgcaaatgac ggctcgtgag cagctcaccg atttctgtaa aactattgat tataaaaatc 137400
ctctatttgt tcaaggcgtt ggtcaaagta aggtcgattt atcatctgga ttttttaatc 137460
caaatcatta tcgtattgaa tggagattta ttgctctgtt ccgtagacaa ttaaagcaaa 137520
ttttatcaac tgcgagtcga ttaaaaggtt ctgatattaa cttaaagaat ctgaaatttg 137580
atggttatac tcttcagatg gaagtaagac cattaaaaga aaataataga actgcacgaa 137640
ttagctttaa acctaataca aaaaattctc tttcaatttg cgaatgcctt aaatcacagt 137700
```

taacagaagc atttaagtat atggatgttg ttgccgctgt tcagtctaag attttacctc 137760
attttgagcg aaattgggaa catacaacaa cgtatgaact tgatatgatc gtttcattta 137820
aatacgattt tttgagaaag gacgaagtca cgcaagagaa aaagcaagaa gcgcaagata 137880
acttaaattt aaatttatcc aattactcat caaacgatcc taaattttgg atgtatagtt 137940
caggtaataa ggatgcatgg aaatttaata aagtgaattt tcttcctatt gaaaatccga 138000
gtcttaaacc tgttgaaaaa tggcatgcag atgcgattga gaagtctatc aaggcagtag 138060
atgatgaact cgttaaagca actaatgaag tgctagaagc tgaaaagacg ctagaaaaag 138120
ctcaagaaaa agtcaaaaat ctcacgaagc aacgttctaa actgaacaat gcactaaatg 138180
cactgaacta gtttacttta ccacaaggat gtggtataat gttcttactt tctactgagg 138240
agattaatat gactcgtaac gaatatatca aatcattcaa tagtgttatt gatgataaag 138300
ttaaacttat gtctagtcag aatagcgtta tttccattat caatcaatgg ctcaataata 138360
ttgatgtaag cattgtttct tcaagcaaat ttattcatga agttcataaa atttctagtc 138420
gtacagataa agatgacatt aaggaaacct ttaaaggttc tcgtcttctt tcatacttag 138480
tcaacagaga tattcttagt aaatttggga aagaaattaa acgaactaaa gatgtagtag 138540
gatataattg gttcggtgat gttaattctt atcatcttaa tattaaagaa gaccctgaga 138600
atatttttac tcgtcgttgg gttagtaatt tcagactttt caagaagcaa cttctaaaat 138660
ccgcttctaa attatgctat ggcgattatc gtcaaattca tccttgggct tctgatatga 138720
ttatcataaa agaatatgaa cttgataaaa ataaagcagc tatttttgtg aattatgaat 138780
tttttacacc agaagctaat caaaagaaca ttaataaatt tttctcaatt gccagtgata 138840
taactcgtca attagagact gcattacttt gtatggaaac ggtagaaaat attcatacat 138900
atcctttcaa aaatttatgc ggttgggaag gatataaaat tgtagttagt ctccgtgaag 138960
taaagtgtgc gtactcaccg actgataaag aaatttacca acaaaaatgt gatgaaattg 139020
tgaatactcc taaagaagaa actacccttg aggaactaat ggataatctt gatgattcac 139080
ctgaaccggt agaaattcgt tcagaagtta ttgcattaga aaaagcttat aaggaagttc 139140
tagaaatttc taataaagcg cagaaagaat atgagcaggc taaaaagatt tgggaagaat 139200
ctgttaatcg tcttgatcgt cttgaacaag ctttacagtt aattaagtaa aatttaaagc 139260
caaggatggc tcggagtata aattattaac taagtgagaa gaacatgaaa actcgtaaac 139320
attatattga ttattttgac agtcttatta ctaaacatcg taattatcag atcgggcaca 139380
gagcagtaat caataatatt cttcgtgatt tccttcaata tgttggccag gaaaatcata 139440
tctgtaaaga tactcaaaac gcttattctc attcgttagg caatttgctt gaatggttta 139500
aacgttctcg tctgttatct tctactgtag ctagtgataa cattaaaaac tttatgaagc 139560
cgagcttcat taaatctgcg acatctataa ctgatttggt tgaatttact attgttaacg 139620
atgttaaaaa gacccacttg gctgattggt tatctaccat tcctgaaact aaatttgctg 139680
ataaatttgc ttgtcaattt aatgaccaag tgaatatgct tttaagcat gctcgcaaac 139740 tgtttaccgc gggtgatgac cgtacaaata cagttcatgt taaggactgg gttattgctg 139800
atgaagtaac acacaagcca ggtggttcat cagtattaat taatatccag gttccttatt 139860
attactcacg taatctcggc accatgacag ctagagaaat taataagcac aacaaaacta 139920
ttcgttcgtt gtcttataaa ctctgcacga tggtggagat gatggacgta gtggaaatgt 139980
atgacgaaac cgaagataat ggttcaatgt tatacagctc acgcattcta attaaactga 140040
agaaccctaa tacatacaag ccagttgtaa aagaacccaa agtagaaaag gttgataacc 140100
tgagtgaaga acgcgaatat cttaatgccc gcttaattga agttgaaaaa cagattgaag 140160
agcatactaa agttcttaaa gatttaactg ccaaagcaaa tggtttacgt aatgctattg 140220
aggtattaaa atgaaaaagc gtctattaga agacattgca gcttcaagta attctagcct 140280
aattaaaatt attatggctg gtgaagaaga cgatctggaa atgcgtggaa agattcatgg 140340
ctgtgacgat ttagatttta aacctccagc ttgggatgcc attatggcta tggttgaacg 140400
gcgtgaaagg gcttctaaaa acgttcctaa ttgtcctgaa tgtggtactg aacaggtgca 140460
attggtccat tggcagacta ataatcttcg ttataaatgt cgtcattgta aacaccgatt 140520
taaccgagaa gaaaatgaca aagcgtaaag aatatatgga gactgctgaa aaggcagtcc 140580
gtgaattagc aatagcttat tataatgaac atggtaaatt tcctgataga tatagtgtgc 140640
ttaaatctgc tttaactcgt tcatataaaa atatgctatc agaagtaagt gatattatat 140700
acaaacataa agaacaaacg ggccaaagtc ttgattacga cgagactttt aaacaagtac 140760
taggaattaa ggaataatat gtttaaagta tatggttatg atagcaacat ccataaatgc 140820
gtgtattgtg ataatgtaaa acgtcttttg accgtgaaga aacagccatt tgaatttatc 140880
aacattatgc cggaaaaagg tgtttttgat gatgagaaaa ttgctgagct tctgactaaa 140940
ctaggtcgtg atactcaaat cggcttgaca atgcctcagg tatttgctcc tgatggaagt 141000
catattggcg gctttgacca attgcgggaa tactttaaat gatgctcgaa ggaactgatt 141060
atatccatga ctaccgcgga agcgcggtat atgtaggtga tgaagttgca gtttactatg 141120
gatatggaac tttgatgaca gccaaagtta ttcaaattaa aaataaccgt gctaaacttg 141180
aagtttatta ttctaatggc gaaaagtcta tttctaagtg gaaatacggc gattgtatgg 141240
tcaaactggg gtaaatatga tttacgatat tagtgtagca agaactccat caatggttac 141300
tattccagct gaagaattag atcgtcttca taaaattgaa gaacttcttt gggaaattga 141360
atctgatttg ccatcaggac tagaatcctg gattgattat gaagaactta ataagcttcg 141420
gagttaaacc ctggtgggcg gttagatggg aaactgtaga gccagagccg gaagaaccgg 141480
tttacactga tgaagaaaca gtatataatg aacctacaat aaatgactta attgatatgg 141540
agatgggaca tgattacagt agataagtgg tttagaatta atcgtgctga tatagggctg 141600
tgtaattact ggccggaact tagtgcaggt actgtcttta aagttcgtga acttgcaaaa 141660
gaatgtgaag atgatataga acctgatact ggaattattg aaattgaact ttctgatgga 141720
aagattatta acatctacga taagccaatt acgtattggt gcttgtggaa tactgaatca 141780
gtcgcaactg gcgaaattga agaagtcgta gaacgagttg atcaagctat tcataaacct 141840
aaagccgctt ttcaaggtga acgtatttca tacgcattag ctaaattagc tgcacaagaa 141900
aataacgatg gttatgaagg aaatttgatg caagctgcgg cagaatatat tgaatggctt 141960
gaaactcaaa tttctttttc tgaccaaaag attcggcaat ataagcgatt gaatcaaatg 142020
ttttacaata cttgaaaata ataaataccc ttatctattt aaggtaaggg tttattatgt 142080
tattgactgg caaattatat aaagaagaaa aacagaaatt ttatgatgca caaaatggta 142140
aatgcttaat ttgccaacga gaactaaatc ctgacgttca agctaatcac ctcgaccatg 142200
accatgaatt aaatggacca aaagcaggaa aggtacgtgg attgctttgt aatctatgca 142260
atgccgcaga aggtcaaatg aagcacaaat ttaatcgttc tggcttaaag ggacaaggtg 142320
ttgattatct tgaatggtta gaaaatttac ttacttattt aaaatccgat tacacccaaa 142380
ataatattca ccctaacttc gttggagata aatcaaagga attttctcgt ttaggaaaag 142440

```
aggaaatgat ggccgagatg cttcaaagag gatttgaata taatgaatct gacaccaaaa 142500
cacaattaat agcttcattc aagaagcagc ttagaaagag tttaaaatga caattgaaaa 142560
agaaattgaa ggattgattc ataaaactaa taaagacctt ttaaacgaga atgctaataa 142620
agattctcgt gtttttccaa ctcaacggga ccttatggct ggtattgtgt ctaaacacat 142680
tgccaaaaat atggtcccgt cttttattat gaaagctcat gaaagcggaa ttatccattt 142740
ccatgatatt gattattccc ctgctcttcc atttactaat tgttgtttag tagatttaaa 142800
aggaatgctt gagaacggat ttaagcttgg taatgcacag attgaaactc ctaaatcaat 142860
tggcgttgct actgcaatta tggcacaaat tactgcgcaa gttgcttccc atcaatatgg 142920
cggaacgact tttgctaatg tagataaagt actttctcct tatgttaaac gcacctatgc 142980
aaaacatatt gaagatgcag aaaaatggca aatcgccgat gcgttgaatt atgctcaatc 143040
taaaacagaa aaagacgtat acgatgcatt tcaagcttat gaatatgaag taaatactct 143100
ctttagttca aacgggcaaa cgccttttgt aacaattaca tttggtacgg gaactgactg 143160
gactgaacga atgattcaga aagcaattct gaaaaatcgc attaaaggtc ttggccgcga 143220
tgggataact cctattttcc ctaagcttgt tatgttcgtt gaagaaggtg ttaatcttta 143280
taaagacgat ccgaactatg atattaaaca gcttgctcta gagtgtgcaa gcaaaagaat 143340
gtatcctgac atcatttcgg ctaagaacaa taaagctatc accggttcat ctattcctgt 143400
ttctccaatg ggttgtcgta gtttcttgag tgtatggaaa gattcgactg gtaatgaaat 143460
tcttgatgga cgcaataatc ttggcgttgt aacactgaat cttcctcgta ttgcgttaga 143520
ttcttatatt ggaacacagt tcaatgaaca gaaatttgcc gaattgttca atgaacgaat 143580
ggatttgtgt tttgaagctt tgatgtgtag aattagttcc ttaaaaggag ttaaagcgac 143640
tgttgctcct attctttacc aagaaggtgc attcggggtt cgtcttaaac ctgatgatga 143700
cataattgag ttatttaaaa atggtagaag ttcagtgtcc ctaggataca tcggtattca 143760
cgaattgaat attcttgtcg gtcgtgatat tggacaggaa attttaacta aaatgaatgc 143820
acatcttaag cagtggactg aaagaaccgg ttttgctttt agcttgtatt ctacacctgc 143880
tgaaaacctg tgttatcgct tctgtaaact cgataccgaa aaatatggaa gtgtaaagga 143940
tgttactgat aaaggctggt acactaacag tttccacgtt tcagtagaag aaaatattac 144000
tccgtttgaa aagatttctc gcgaagcacc atatcatttc attgcgacag gtggtcacat 144060
ttcttatgtt gaacttcctg atatgaaaaa taacctaaaa ggtcttgagg ctgtatggga 144120
ttatgccgcg caacatttag attattttgg cgttaacatg ccagtagata aatgttttac 144180
gtgtggaagt acccatgaaa tgactcctac tgaaaacgga tttgtttgtt ctatttgtgg 144240
agaaactgat cctaaaaaga tgaacaccat aagaagaaca tgcggatatc ttggaactcc 144300
tagcgttgtt ccatggaatt taggtaaaat gaaagaaatg gtaaaacgag taaaacatgc 144360
ataggtatta tataatttat aaaataacaa atataattaa ttcaaaggaa tatatcggtg 144420
cgcatagcac cgataacata aatgacggtt atatggggtc aggaacattg attcgtgccg 144480
ctttattaaa atatggtaga aaaaatttta ataaagaaat tttacatgtt tttgataatg 144540
aaaaacaaat gtatgataaa gaagctgaac ttgtaaccga agagtattgt ctaaaagaaa 144600
atacatataa tattaaaccc ggtggaaaag gtggaactgc ctatgaacag acacttgaac 144660
atcgccgcaa aaatagttta gcaaataaag gtaaaaagag aacagaagaa actaaaatag 144720
ctatttcacg tgctttaaag aaatataaac gtacgccaga gcatcaagca aatttaaata 144780
```

-continued

```
aagccgtaag catagctatg aagcgaaaag atgttagaag taaattagct ggagggcggt 144840
ctgagaaaga taaattatct atatcaaacg gtgttaaaaa atattacaat tctttgagtg 144900
aagaagaacg cgaacttcat cgcaagcgaa ttattgaagg taaaaagaat tctcccatgt 144960
cattggaatc tagacaaaag ctttcaaaag ctttaaaagg acttcaagtt ggttcaaaaa 145020
atccaatgta tggaaaaatt tctccaacta gcaaaaccgt ttcagttgac ggtattaaat 145080
atgattcaat taaaaagtgc tcaaatgcca taaaagtttc tagacatctt atactaaaac 145140
gctgtaattc tactgatgaa gcttggaaaa attggatatt attatgaatt atgacagaat 145200
atacccgtgc tgctttgtga atggccctgg atgcagggtc gttcttttcg ttacaggttg 145260
tttgcataaa tgcgaagggt gttataataa atcaacatgg aatgctagaa atggtattcc 145320
attcactggt gaaacattag aacaattaat tgaatgtttg aataatgatt atatagaagg 145380
attaactata accgggggtg accctcttta tcctgataac agagacatga ttcactctgt 145440
ggttcaaact attaaaaatc tttatcccaa taaaagcatt tggttgtgga caggatataa 145500
gtttgaagat attaaacaac tagaaatgct taaatatgtt gatgttatta ttgatgggaa 145560
gtatgagaaa aatcttccga ccaaaaagct gtggcgagga tcagataatc agcgactttg 145620
gtcaaatacc gatggggtgt ggaaacatga ttaaattgaa ttacattatg gatactataa 145680
atgatatgat ttttcatttt ggtccagaat tttattcgca gtatagttta gtacttatca 145740
atgcttggtt aattaattaa ggataaaata tgtataaatt tcgtaaaggt ttagctgatt 145800
ttcttacaac tgtagcattc tttctgttta tggcagttgg agctattttc cttattcctt 145860
ttattgctat atttttcgtg attagtttaa tttctccaga aaaaggctta tcttccagtg 145920
agttcagtga gcgtctggat aaaattacta acaagctgaa tgctgctctt agtaaggaat 145980
agttgtgaaa caaaataaga ttgaagtcta tggaattcca gatgaagtag gtcgttgtcc 146040
tggatgtcaa tcagttacaa aacttctaaa ggagctcaat gctcctttta ctttctataa 146100
agttcttaca aataatggta agattgagta tgatcgtcca ctgattgtat ctcttgccaa 146160
acgcgccgga ttcacatctc ttaacattcg ttatccagtc attttcatta atgattccag 146220
acaaaagaac attaaacact tcaaagaaac cctcatttca cttggatatg atagagatat 146280
catagaagac taagataggc cctctgggcc tttctttctt acattctgta tattaccatt 146340
ctaagctatc gttcctttct tatcattccc taaaatattt tcacaaagtt gtttacaaca 146400
agttcaaacc gtggtattat taacacatga attgcctttg aggaattgat atggttatga 146460
ttgataaaga aattaaaaag ggacagtatt atcttattaa tggtaatgtt gttcgcgtta 146520
cttacgtaaa tggttatgat gtttattatc ttatacttaa gttacataaa cacatgattt 146580
gtgaccgtgc tgtatttagt tcagttgcta aggaaattaa actccatggg taaaacgtat 146640
cgtcgtaaag acttaaaagt gcgtgattat gactatttcg gaaagcgtaa agctcctgat 146700
ggggtaagtc ataaagatat ggttgaaaac atttttcgct cagataaatg gcgtagaatg 146760
aaaggtattg attcagaagt taaagatgag ttaaatcgtc aattacgcgg tgaagtaaga 146820
aagttgaaaa aatcagttta cattgacgat gattttgatt ataatacttc tcaacgagtt 146880
gctaaacgta aatcaaacga atgttatcgt tacagctgag gaaaatatga atatcaaacg 146940
aatgcttttt aagcaggggt tatacacttt aaatgttact ccaaaaggtg atacaactaa 147000
gtggtcagta aatgactgga ttaaatttat tgatgaaaac ggtaactgga aaatttaaat 147060
gaatcctgaa tctaaattat cacaacgaat tgccgaatct cgtcgtcagt tctttgaaaa 147120
tatgatagcc caaggtattg atgatgaagt tttctaaat tggttctgga ataataagta 147180
```

```
tgcagcatgt gaaggagctt tgtcattgtc agtcgcaatg atgtacgaag gctggaaggg 147240
tgccaaaaag tttagctaag ggcttcggcc ctttttggat aataaaattt taacgtaatt 147300
gaggataatg tatgactatt caaattaaaa acgtcattaa ttcttacgca tatgataaag 147360
tagtttcttt gctagaaaaa ggcgatattg taactcctca aattttggat aaatgggaaa 147420
aagagcttca tcagatgatg aaacagaatg atcagaagat tggacgcaat actgtccgtg 147480
aattgttggt tcaatatatc ttgtcagaat ttgatgttaa agcttttggt gtagaatcta 147540
aagcttatca aaagcatgaa atttccgata aaactattcg tcgcatgaaa aatcaacgca 147600
agaaaaaatt tgcagacctg aaaattacta aggtataatt atgaacgaag ctcttattaa 147660
cgatttgcgt cttgctggat atgaagtaaa tacaaatggc attggtttaa ctcaaattga 147720
aggaaacgga ttcatccttg agtatgaatt tagccaatgg tggttatatg ctaattacgg 147780
cgaattgatt gaatatgttg accaatttga ttcactagat gcagctcttg aagcggctaa 147840
gttgatgaat gtatgaaatt tattaatatt tctattacta ttgaaaatta tggcattttc 147900
tatgttgacc aatgcatgaa aatttcattt ttcccaaata agactggtgt tggatattgg 147960
gaaagtcatg tttctgaatt aaatgaaagt gaatatgtta gcacacatga aaagttttta 148020
gactttttat attgcgctga tattaatgat cattacatag atattcatga atttaaaaag 148080
atgatggaga aagtgttcca agcatactgc ttacttagat aactgatatc ctctatgctt 148140
taagatagat cttcaaatat tatgatataa tagatctatg aattgagcta agaggtgaaa 148200
atgtcagaaa ctaagcctaa atataattac gtaaacaata aagagctttt acaagctatt 148260
attgattgga aaacagaatt agcaaataat aaagacccaa ataaagtagt tcgccagaat 148320
gatactatcg gattagccat tatgcttatt gcagaaggct tatctaaacg tttcaacttt 148380
tcaggataca cccaatcctg gaaacaagaa atgattgcag acggtataga agcttctatt 148440
aaagggcttc acaattttga tgaaacgaaa tataaaaacc cacatgcata tataactcaa 148500
gcttgtttta atgcattcgt ccaacgtatt aaaaaagaac gtaaggaagt tgcaaagaaa 148560
tacagttact tcgttcacaa tgtctatgac agtcgtgacg acgatatggt tgcgttagta 148620
gatgaaactt ttattcaaga catctacgat aaaatgacgc attacgaaga atcaacctat 148680
agaacaccgg gggctgaaaa gaaaagtgtt gtagacgatt ctcctagttt ggatttttta 148740
tatgaggcta acgattaacc tctccggatt cttggaagaa atacctgaag ttgaagctat 148800
tccctattta cttaaaatgt atctcaggga agttttagct cttgacattg atattgatcc 148860
agaaaatccg tatgataccg cttttaaatc taatggtgta gaattaaact atcggtatca 148920
tttaacagat gatgattttt attttatatt agagaaataa tatgactgat aaacccgaaa 148980
ttaatgatga agtggaaaag cttatttctt ctattgaaga aaagaaccgt cttgaagcag 149040
aaagaaaagc aaataagtta ttgtctaaaa acaaacgcga actgaatcgt ctttataagc 149100
atgctcagat tgcggctgaa aataataatt ttgctcaata cgaatatgct atcaagaaaa 149160
gtcgggatat tctaaaacag ccatataacg atgaactcat cagtattctt tggaagacta 149220
ctagatcaca gattgaggat atgattgatg cttacacacg taaaattcaa gcgtcttaaa 149280
attaatgcag gatttactga atctttgaat ggtcatcttt gcgtgaaaat ttctgaaaaa 149340
gaataccatg atagttcaat taaagaagtt aatcctccta ttgtaagagc agaccctaat 149400
atgaaagtgt gggttgattc ctatcaagtc aaaaaatggt ggcaactgtg aaagatgaac 149460
gcccagactt gtgaaataga ttataataaa attcgttcct ctaaagtaga aatgatgagg 149520
```

```
cgctttaaag agtctcatga taaagctaaa gcagaaggaa ctataacaca taaacgtata 149580
aaatttagaa gctctaatga gcctctgtat ggtgtattat gcggatagga gcttcggctc 149640
ctatattgct ttataaattt ttggtaaaat aaaccaaaac aatgaggata ttaaatgaaa 149700
gtatgcattt ttatggctcg aggtcttgaa ggttgtggcg taactaaatt ttctcttgag 149760
caacgtgatt ggtttattaa aaatggtcat gaagtaactt tggtttatgc taaagataaa 149820
tcatttactc gtaattgcgc gcatgattat aagtcatttt caattccagt tttattggca 149880
aaagaatacg ataaaacact taagctggta aatgattgcg atattctaat tatcaattca 149940
gttcctgcta cttcagtaga agaagacact attaataact ataaaaaaat tattgataac 150000
attaaacctt cagttcgtgt tgtagtttat caacatgacc attcttctct ttctttgcgc 150060
cgaaatttgg gattagaaga aactgttcgt cgagctgatg ttatttttag tcattctgat 150120
aatggcgatt ttaataaagt tctgatgaaa gaatggtatc cagaaactgt ttcactgttt 150180
gatgatattg aagaagcacc gaccgtatac aactttcagc ctcctatgga tattgcgaaa 150240
gttcgatcaa cctactggaa agatgtttct gaaattaaca tgaatgtcaa ccgttggatt 150300
ggtcgtacga ctacatggaa aggtttttat cagatgtttg attttcacga aaaacatctt 150360
aaacctgctg ggctaagtac tattatggaa ggtctggaac gttctcctgc gttcattcct 150420
attaaagaaa aaggaattcc atacgagtat tatcgtcttc atcaagtaga ccaaattaaa 150480
attgctccta atttgccaac gcaaattctt gaccgttatg taaatagcga aatgcttgaa 150540
cgcatgagta aatccggatt tggttatcag ttgagtaagt tggacaaaaa atatctacaa 150600
cgttctttag aatatactca tctcgagctt ggcgcgtgcg gaacaattcc agtattttgg 150660
aaatctactg gtgaaaattt aaaattccgt gttgataata ctccgctaat ttcacacgat 150720
agcggtatcg tttggtttga tgaaaatgac atggaatcaa catttgagcg tattaaagaa 150780
ctgtcatctg accgagctct ttatgaccgt gaacgcgaaa aagcttatga atttttgtat 150840
cagcatcaag attcaagctt ctgctttaaa gaacagtttg acattattac aaaataaagg 150900
gcttcggccc tttagcttta tacggagttt gatataatga tatttcttgg atatgtgata 150960
ctttttctcg cattttatct attcactaga gcatgttgga ttgggttctt tagcacacca 151020
gatgggttta tttcaataat tttattttgc atttcaatga cggttcttga tatatgaaaa 151080
ttttaaattt aggtgattgg catttaggcg ttaaagccga tgatgagtgg attcaatcca 151140
ttcagttgga tggaattaaa caagcaatag aatattctaa gaaaaatgga attactacat 151200
ggattcaata cggcgatatt tttgatgtgc gaaaagcaat cacgcataaa actatggagt 151260
tcgctcgtga aatagttcaa atgcttgatg atgctggtat tacactgcat actgttgtag 151320
gaaaccatga tatgcacttt aaaaatactt taactccaaa tgcttctact gagcttttgg 151380
ctaaatatcc taatgttaaa gtatatgata agcctactac agtagatttt gacggatgtt 151440
tgattgattt aattccttgg atgtgcgaag aaaatactgg tgaaattctt gagcatatca 151500
aaacttcatc tgcttctttt tgtgttggtc actgggaact gaatggattt tatttttata 151560
aaggaatgaa atctcatggt cttgaacctg atttccttaa gacttataaa gaagtgtggt 151620
ctggtcactt ccatactatc tctgaggctg ctaacgtcag atatattggg acaccatgga 151680
cactaactgc aggtgacgag aatgaccctc gtgggttctg gatgtttgat acagaaacag 151740
aacgaatgga atttattcca aacaacacta cctggcatcg tcgaattcaa tatccattta 151800
agggaaaaat tgactataaa gattttacaa atctatcagt acgtgttata gtaactgaag 151860
tagacaaaaa tctaacgaag ttcgaatctg aactagaaaa agttgtgcat tcattacgag 151920
```

ttgtgtcaaa gattgataac tctgtcgagt cagatgatag tgaagaagtt gaagttcaat 151980
ctcttcagac attgatggaa gaatacatta atgcaattcc agacatcact gattctgatc 152040
gcgaagcact tattcaatat gcaaatcagt tatatgtaga ggcaacacaa tgatttttga 152100
tgaatttaaa aatgttatga tgagtcagca ttttgaatgc gaagtaaaag atgatattgg 152160
gcataaagaa attattgaat attggtttga accgctagag gttgaagata attgtattaa 152220
aaaggttacg gtctgcactg actgggctgt atcttttaac ttcaacattt tagataatga 152280
cacacctaaa tcattacaag atatggctgt atcttgtatt aaggatgcat actgtgaagt 152340
tttcgacatt tgacattaac gatgaattcg tagcaaatat tgattacacc gaagaagatt 152400
ctagatatgt tggaataatt tatatcacat caaaagcagc acaaggtgtt gtttgcatgg 152460
ctgaatttga tgaatacttt ttagattatg atgatatgat agaatggtct aaaagataca 152520
ttaaaaggaa tcttttgtga agaattttaa actaaaccga gttaggtatc aaaatataat 152580
gtcagtaggt ggaaatccta ttgacattca actagataag gttcaaaaaa ctcttattac 152640
tggacgaaat ggcggtggta agtctactat gttagaagcc atcacatttg ggctttttgg 152700
caagccattc cgtgatgtaa agaaaggcca attaataaac agcacaaata agaaagaact 152760
tttagttgaa ctgtggatgg aatatgatga gaaaaagtac tatatcaaaa gaggacaaaa 152820
accgaatgtt ttcgaaatca ccgttaacgg tacacgtctt aatgaatctg ccagcagtaa 152880
agatttccaa gcagaatttg aacagcttat cggaatgtca tatgccagtt tcaagcagat 152940
tgttgtcctt ggtacagcag ggtatacccc tttcatgggt ttgtcgaccc ctgcgcgaag 153000
aaagcttgtg gaagacctgc ttgaggtagg aacattagct gaaatggata agcttaataa 153060
agcactaata cgtgaattaa actcacaaaa ccaagtgctt gatgttaaaa aagatagtat 153120
tatccaacaa attaaaatat ataacgataa tgttgaacgc cagaaaaaat tgtctggtga 153180
caatcttact cgtctgcaga atatgtatga cgatttggca aaagaagcta gaacgctaaa 153240
atcggaaata gaagaagcta atgaaagatt agttaatatt gttttagatg aagacccgac 153300
tgatgcattt aataaaatcg gtcaagaagc agttttgatt aaatcaaaaa ttgactcgta 153360
taataaagtc attaatatgt atcacgaagg tggattatgt ccaacctgtt tgtcacaatt 153420
aagttccggt gataaagttg tttctaaaat taaagataaa gtttctgaat gtacgcattc 153480
gtttgaacag ctttcaacac accgtgataa tttaaaagtt cttgttgatg aataccgaga 153540
taatattaaa acccaacagt cgttggcaaa tgatattcgc aataaaaagc aatctctgat 153600
cgcagcagta gataaagcta aaaaggttaa agcggctata gaaaaagcat cttctgagtt 153660
tattgaccat gctgatgaaa tagcactgct tcaagaagaa cttgataaaa ttgttaagac 153720
aaaaactaat ttagtaatgg aaaaatacca ccgaggaatt ttgactgata tgctcaaaga 153780
ttctggtatt aaaggtgcta ttattaaaaa gtacattcca ttatttaata agcagattaa 153840
ccattatctt aaaataatgg aagcggatta tgtgtttaca ttagatgaag aatttaatga 153900
gacaattaaa tcccgtggtc gtgaagattt tagttatgct tcatttagtg aaggtgaaaa 153960
ggcacgaatc gatattgctc ttttatttac ttggcgtgat attgcttcta tcgtatctgg 154020
tgttagtatt agtacattaa ttcttgatga agtgtttgat gggtcatttg atgccgaagg 154080
tattaaaggt gtagctaata ttataaattc aatgaaaaac actaatgttt ttataatttc 154140
gcataaagac catgacccgc aagaatatgg tcagcatctt caaatgaaga aagtcggtcg 154200
atttactgta atggtttaat ttataagaga ttatgcttta atttattaga gtataatctc 154260

-continued

```
tatggaggaa aaacatggaa tattcaactg gacagcatct attaactttt cctgaaataa 154320
aacgatatat tctgagaaat aatttttcta atgaagagca tatagttact gaatctatgc 154380
ttaggaatgc atttaaatca gaatatacaa aaataatgtc caatagaaat gaagcttgga 154440
ctgttactga ttattatgac taaaggtgta ttatgactaa aattactgtg aattatactg 154500
ttgatgtaaa agatattcag ccaaaacacg tgcgttctga atcaaatcca caaaaccaaa 154560
ataaaattcg tcgagcatgg gttttgtctc tttctgataa cgcaatggaa gttattcaga 154620
acaaaattaa atctgcacct gctcgtcatg cgtattatga agctatcgat cgtgaagtaa 154680
gtaataaatg gattgaatta atgcgcaaac atactacaga atctctaaac gccggtgcta 154740
aatttattat gacttcatgt ggtgaacgcc ttgaagatga atattgtggc aatgcagatg 154800
aacgtctgat tgttgccgct caaattgttg ccgaaacaat cgcagctgat tttaatcgtt 154860
aattgcttta ttaaattagt tataaaatta aatctcattt gaattgaagg aaattacatg 154920
aaactgtcta aagatactac tgctctgctt aaaaatttcg ctactattaa ctctggtatt 154980
atgcttaaat ccggtcaatt tattatgact cgcgcagtta atggtacaac ttatgcggaa 155040
gcaaatattt ctgacgttat tgattttgat gtagcaattt acgatttgaa cggttttctc 155100
ggtattctgt ctttagttaa tgatgatgca gaaatttccc agtcagaaga tggtaatatt 155160
aaaattgctg atgctcgctc aacaattttt tggccagcag ccgatccgag tacagtagtt 155220
gctcctaata aaccaattcc attcccggta gcatctgttg ttactgaaat taaagctgaa 155280
gaccttcaac aactgttgcg tgtatctcgt ggtctgcaaa ttgatacaat tgctatcacg 155340
gtaaaagaag gtaaaatcgt aattaacggt tttaataaag tagaagattc tgctctgacc 155400
cgtgttaaat attctttgac tcttggtgat tatgatggtg aaaatacatt taatttcatt 155460
atcaatatgg caaatatgaa aatgcaacca ggaaattata aacttctgct ctgggcaaaa 155520
ggtaaacaag gcgctgctaa atttgaaggt gaacacgcga attatgtagt agctcttgaa 155580
gctgattcta cccacgattt ttaatagagg gcttcggccc tttataattt acactaaaac 155640
ttgaatgagg aaattatgat tactgtaaat gaaaaagaac acattcttga acagaaatat 155700
cgtccatcta ctatcgatga atgtattctt cccgcctttg ataaagaaac ctttaaatct 155760
attacaagta aaggtaagat tccacatatt attcttcatt ctccttctcc aggaacaggt 155820
aaaacaactg tagcaaaagc attgtgtcat gatgtaaatg ctgatatgat gtttgtgaat 155880
ggatcagatt gtaaaattga tttcgttcgc ggtcctttga ctaattttgc cagtgcagct 155940
tcatttgatg gtcgtcaaaa agtaatcgtt attgatgaat ttgaccgttc aggtttagca 156000
gaatctcagc gacatcttcg ttcctttatg gaagcttata gttcaaactg tagtattatt 156060
attactgcta ataatattga tggtattatt aaaccacttc agtcacgctg ccgagttatt 156120
acattcggtc aaccgaccga tgaagataaa attgaaatga tgaagcagat gattcgtcga 156180
ttgactgaaa tctgcaaaca tgaaggaatt gctatagctg atatgaaagt tgtagcagct 156240
ttggttaaaa agaattttcc tgattttcgt aaaactattg gcgagctcga tagttattca 156300
tctaaaggtg ttttggatgc tggtatttta tcactggtta ctaacgatcg tggtgctatt 156360
gatgatgttc ttgagtctct caaaaataaa gatgttaaac agctcagagc tttagcacca 156420
aaatatgcag ctgattattc gtggttcgta ggtaaacttg ccgaagaaat ctatacacgc 156480
gtaactccgc aaagtattat tcgtatgtat gaaattgtcg gcgaaaataa ccagtatcat 156540
ggaattgcgg ctaatactga attacattta gcgtatcttt tcattcaatt ggcatgtgaa 156600
atgcagtgga agtgatatga gcttatttga agatgatatt caattaaacg agcatcaagt 156660
```

```
tgcttggtat tcaaaagatt ggacagctgt ccaatctgct gctgattctt ttaaggaaaa 156720
agctgaaaat gaatttttttg aaataattgg agctattaat aataaaacta aatgctctat 156780
tgctcaaaaa gattattcaa aatacatggt tgagaatgca ttatcacaat ttccggagtg 156840
catgccagct gtatatgcta tgaatttaat tggatcaggt ttaagcgatg aagcccattt 156900
taattatctg atggctgctg ttcctcgggg taaaagatat ggtaaatggg caaaactggt 156960
tgaagattct accgaagtat tgattattaa gttacttgct aagcggtatc aagttaatac 157020
aaatgatgca attaactata aatcaattct tactaaaaat ggaaaacttc ctttagtatt 157080
aaaagaacta aaaggtttag tcacggatga tttttttgaaa gaagtgacta agaatgtaaa 157140
agaacagaaa caactcaaaa aactagcatt ggaatggtaa aatgattgaa attactctta 157200
aaaaacctga agattttctg aaagttaaag aaactttgac tcgtatggga attgctaata 157260
ataaagataa agttctgtat caatcctgtc atattctcca gaaaaaagga ctatactata 157320
tcgttcattt taaagaaatg cttcgtatgg atggtcgcca ggttgaaatg acagaagaag 157380
atgaagttcg tcgtgattcg attgcatggc tattagaaga ttggggactg attgaaatcg 157440
ttcctggtca aagaactttt atgaaagatt taactaataa cttccgagtt atttctttta 157500
aacaaaaaca tgaatggaaa ctcgttccta aatatacgat tggtaattaa tatgactgct 157560
ataactccgc aagaatacat ggcgtctctt aaagaaaaat ataatctttc tgcaacagaa 157620
acactttttg atttaccaga aaacctccaa ctaaaatttc aggtagaatt tcaaaaacta 157680
gttcatccag aacaaaaaca ttttacagca gtcgttaagt caattaatgc agatggaatg 157740
acaatttttc accgacaaat agtactaatt taagcaaggg gcttcggccc cttatttgga 157800
gtataatata tcaagagcct aataactcgg gctataaact aaggaatatc tatgaaagaa 157860
ttttatatct ctattgaaac agtcggaaat aacattgttg aacgttatat tgatgaaaac 157920
ggaaaggaac gtactcgcga agtagaatat cttccaacta tgtttagaca ttgtaaggaa 157980
gagtcaaaat acaaagacat ttatggtaaa aactgcgctc ctcaaaaatt tccatcaatg 158040
aaagatgcac gagactggat gaagcgaatg gaagacatcg gtctcgaagc tctcggtatg 158100
aacgatttta aactcgctta tatcagtgat acgtatggtt cagaaattgt ttatgaccga 158160
aaatttgttc gtgtagctaa ctgtgacatt gaggttactg gtgataaatt tcctgaccca 158220
atgaaagcag aatatgaaat tgatgctatc actcattacg attcaattga tgatcgtttt 158280
tatgttttcg acctttttgaa ttcaatgtac ggttcagtat caaaatggga tgcaaagtta 158340
gctgctaagc ttgactgtga aggtggtgat gaagttcctc aagaaattct tgaccgagta 158400
atttatatgc catttgataa tgagcgtgat atgctcatgg aatatatcaa tctctgggaa 158460
cagaaacgac ctgctatttt tactggttgg aatattgagg ggtttgacgt tccatatatc 158520
atgaatcgcg ttaaaatggt tctcggtgaa cgtagtatga aacgcttctc tccaatcggt 158580
cgagtaaaat ctaaactaat tcaaaatgtg tacggtagca aagaaattta ttctattgat 158640
ggcgtatcta ttcttgatta tttagatttg tacaagaaat tcgcttttac taatttgccg 158700
tcattctctt tggaatcagt tgctcagcat gaaaccaaaa aaggtaaatt accgtatgat 158760
ggtcctatta ataaacttcg tgagactaat catcaacgat acattagtta taacatcatt 158820
gacgtagaat cagttcaagc aattgataaa attcgcgggt ttatcgatct agttttaagt 158880
atgtcttatt atgctaaaat gcctttttct ggtgtaatga gtcctattaa aacttgggat 158940
gctattattt ttaactcatt gaaaggtgaa cataaggtta ttcctcaaca aggttcgcac 159000
```

```
gttaaacaga gttttccggg tgcatttgtg tttgaaccta aaccaattgc tcgtcgatat 159060
attatgagtt ttgacttgac gtctctgtat ccgagcatta ttcgtcaggt taacattagt 159120
cctgagacta ttcgtggaca atttaaagtt catccaattc atgaatatat cgcaggaaca 159180
gctcctaagc caagtgatga atattcttgt tctccgaatg gatggatgta tgataagcac 159240
caagaaggta tcattccaaa ggaaatcgct aaagtatttt tccagcgtaa agactggaaa 159300
aagaaaatgt tcgcggaaga aatgaatgcc gaagctatta aaaagattat tatgaaaggc 159360
gcagggtctt gttcaactaa accagaagtt gaacgatatg ttaagttcag tgatgatttc 159420
ttaaatgaac tatcgaatta cgcagaatct gttcttaaca gtctgatcga agaatgtgaa 159480
aaagcagcta cacttgctaa cacaaatcag ctgaaccgta aaattcttat taacagtctt 159540
tatggtgctc ttggtaatat tcatttccgt tactatgatt tgcgaaatgc tactgctatc 159600
acaatttttg gtcaagtcgg tattcagtgg attgctcgta aaattaatga atacctgaat 159660
aaagtatgtg gaactaatgg tgaagatttc atcgcagcag gtgatactga ttcagtatat 159720
gtctgtgtag ataaagttat tgaaaaagta ggtcttgatc gctttaaaga acaaaatgat 159780
ttagttgaat tcatgaatca gtttggtaag aaaaagatgg aacctatgat tgatgttgca 159840
tatcgtgagt tatgtgacta tatgaataac cgcgagcatc tgatgcatat ggaccgtgaa 159900
gctatttctt gtcctccgct tggttcaaag ggtgttggtg gattttggaa agcgaaaaaa 159960
cgttatgctc tgaacgttta tgatatggaa gataagcgat ttgctgaacc acatctaaaa 160020
atcatgggta tggaaactca gcagagttca acaccaaaag cagtacaaga agctctcgaa 160080
gaaagtattc gtcgcattct tcaggaaggt gaagagtccg tccaagaata ctacaagaac 160140
ttcgagaaag aatatcgtca acttgactat aaagttattg ctgaagtaaa aactgcgaac 160200
gatatagcga aatatgatga taaaggttgg ccaggattta aatgcccgtt ccatattcgc 160260
ggtgtgctaa cttatcgtcg agctgttagt ggtctgggtg tagctccaat tttggatgga 160320
aataaagtaa tggttcttcc attacgtgag ggaaatccat ttggtgacaa gtgcattgct 160380
tggccatcgg gtacggaact tccaaaagaa attcgttctg atgtgctatc ttggattgac 160440
cactcaactt tgttccaaaa atcgtttgtt aaaccgcttg caggtatgtg tgaatcggct 160500
ggcatggact atgaagaaaa agcttcgtta gacttcctgt ttggctgata gaataaatct 160560
agggacctcc aggtcccttt ttcatacaag taatataaat ctatacttat gaaaaagaga 160620
tgattctagg tcctgtaaat tcattaaaaa ttttttcaca aaacggttta catctctgtt 160680
cttccatggt actatacaac tatcaactga tacggatttg gagaataaaa tgaaaattgt 160740
ttatggttgt ttagcagcgt gtttagttgc attagcagtt gttctagttg cattagcagc 160800
tgttccattt attgatattg aaaatgacac tcagaatgtg attgaatcta atactgttat 160860
tcacatgaat ggtaaagtat caacaaaaat tgatgataat cttcatatga atactaatgg 160920
aacgcttggt gttcaattag gtaatacctg tgtaagcact actggagtaa ttactacttg 160980
tatttgagga aattattatg aaaattgcta ttttggttat tacattgggt cttactgact 161040
gtgtagctca aggaccggta gtaaatcaat ctgatgtagg aaaaattgta aactgttcaa 161100
gcaaatttta taatcctaac gtcaagtgtt ataaagaagc tccaaaacag acagtagaac 161160
aaatgcaggc gaattttgac gaagctattc gtccagatga atctgctcaa gcatatcgta 161220
attcagatgt aattacacgc gaagaaaaaa ttgaaaacta ctgcgccgaa ctttgggcta 161280
attgggctaa taattaccaa tggcgtacag gtaaaaatgc tccgatggag tatgtagtga 161340
attcttataa ttcatgtgta aaaaatttga ctaagtgagg aaaacatgga aactttagta 161400
```

gcaggttcaa tttttatggt tttagtttca ggcgtgttgg ctatcattat atacatgctt 161460
ccgtggttca tcgccttgat gcgtgggtca aaatcgacag taggaatctt tttcacatct 161520
ttactgttta attggtcaat tattggttgg tttattacat ttatttggtc aattgcgggt 161580
gaaactaaaa aatctgcaca accgaatcaa gtaattatca tcagagagaa ggaatgaaaa 161640
gcaaaatttt agcagtattg cttttaatct tgatgattat aataagtata tactatagcg 161700
taacggttcc ttgtatgatt ccgacactta ttataggttg gggtttatta ctgttacaag 161760
ttaaatatga atgtatcaat tgaggtttaa atgattagtg actctatgac agttgaagaa 161820
atccgtcttc atttggggct tgcattaaag gaaaaagatt tcgtagttga taaaactggc 161880
gttaaaacta ttgaaattat tggcgcatca tttgtagcag atgaaccgtt tatttttggc 161940
gctcttaatg atgaatacat tcagcgtgaa cttgaatggt ataaatctaa aagtttgttt 162000
gttaaagata ttccgggtga aacaccgaag atttggcaac aggtagcatc ttctaaaggc 162060
gaaattaatt cgaattatgg ttgggccatc tggtcagaag ataactatgc ccaatatgat 162120
atgtgtttag ctgaacttgg tcaaaatcct gattctcgac gcggtatcat gatttatact 162180
cgtccatcca tgcaatttga ctacaataaa gatggtatgt cagatttcat gtgtacgaat 162240
acagtacagt acctgattcg tgataagaaa gtcaatgcgg ttgttagcat gagaagcaat 162300
gattgctggg caggctatcg taatgattat gcttggcaaa aatacgtact agataaatta 162360
gtatctgatt tgaatgcagg cgacccatcg cggcaatata aagcaggttc tattatatgg 162420
aacgttggaa gtcttcatgt gtacgaaaat cagttttatt tagttgacca ttggtggaac 162480
accggtgaga ctcatattgc taaaaaggat tatactggaa aatggaagta aatgtgccac 162540
atgtttataa gtataaacat cctaaaacta aaaagtggta tataggaagt catgatggtc 162600
acaacccgaa ttatgatggt tcgggtgtag tttggcaaca tgctaaaaag aaatatggaa 162660
taaaatcctt taataaagaa atattatatg aaggaccaat gtttagacag gttgaagaaa 162720
ttattttaac ttgtttagat gctgctaatt gtccggattc atataattta aagaatgaag 162780
catggggagg aagttttcca ggcaaattaa atggaatgta cggtaaaaaa ctatctccag 162840
aagaaagata taagtgcgga aatgcctttc gtggaatcaa gcgtcctgat cattctaaaa 162900
gaatgaaagg cgaaggtaat ccaatgtatg gtaaaaatga gcaggcatat ggaattataa 162960
atcgagccaa ggaaaattct ggtaaaactt atgaagaaat tttggcgtta gaaaaagcta 163020
aaataattaa agaaacgatg tctaaaaatc gtaaaggaaa acctcataat ttgatagaaa 163080
aaatatgtcc gcattgcgga ctaaaaggac gtgggccaaa tatgacaaga taccattttg 163140
acaaatgtaa ggcacttaaa tgattcaatt cgtaattcca agttatcagc gtgtcggggc 163200
agtttctgcc cttaatatgt ttccgactga ttatgaaccc catattgtag tgcgtgaaca 163260
tgaagaaaaa gtttattatg atgcttatgg gtctagagct aaaattatag ctattcctga 163320
tgatgttaat ggaattgccg gtactcgtaa agcaattact gatatgtatg caggtcaacg 163380
aatctggatg attgacgatg atactactat tcgtatgagt tcaatacgaa agagagacga 163440
taaacggcgc gtagataaaa ttaatcaatt aactcgtgaa cagttctatg aattgattca 163500
atacgttgaa gatgctatgg attgcgggta ttatcacggt catgctcgtc taccaatttt 163560
taaaattact tcatcttggg gtaattatcg tgaaaactca tatggattca cgaatacatg 163620
gtatgacctc ggaaaactta cggcagaaca aattgggtat ggaaaaattg atttatgcga 163680
agatatgtat gcatttctca atttaattaa tcaaggttat ccgcatttgg ccttgttcaa 163740

```
atatctagtt gtatctggaa aatcacacgc tcccggtgga tgtagttcaa ttcgtagtaa 163800
ttctaaacat aatagagcgc ttgagcaaat caatagagag tttccagagc aagctcgttg 163860
gaaaacttca aatattgaaa aacgaaaatc gttgggtgaa gaagacgagc cattaaaggt 163920
tcttcgcatg tgtgtttcgc gtaaagaaaa atcagaagca tttcataagt ttaatgctat 163980
tcatccaata gcagttgatt aatgcctaaa tttattgtgt tataattact ttatctttaa 164040
ccagtgagga aaatataatg atgcctatgg aaaaaatgaa tgtctattgc agatttaaaa 164100
tcccgtttga ttaaagcttc cacttctaaa atgactgctg aactgactaa agcaaagcaa 164160
gttctttaat gaaaaggatg tggttcgtac taaaattcca atgctgaata ttgcaattag 164220
cggtgcgatt gatgacatga aaagacataa agaaaagaaa tataattata cttatgttat 164280
aactaattta gttaataata aaatttacta tggaactcat tcaaccgatg atttaaatga 164340
tggttatatg ggatcaggaa ctttattagc acaagccaag aaaaagtatg gtaagaaaaa 164400
ttttaattta agcattcttg ggttttataa agattttaaa tcagcccgtg atgctgaaag 164460
agaattagta acaatagatg tggtaaatga tcctatgact tataatttaa aaattggtgg 164520
agagggtggt agaagaattg gttatagagt ttcatcagaa accaaagaaa aaatttcaaa 164580
agctcaaaaa ggaaaaccaa aacatcttgg atttagtgat gtttgccgga aagcccagct 164640
aggcaaaaag cagtcagaag aaactaaagc aaaacgaaaa gaagctttgc ttaataatcc 164700
atatggttat aatagaaata aaccatcaca taaacgtgac ccaataatgt gggataacat 164760
tgaaaagatt aaagaaatat gggaaaactc tggaaaaccc ggtgctatta agcttaaaaa 164820
attagcaatt gaagctggat ttccaaataa atcttatgca agaatgctcg aagtatttcg 164880
tggaacaaga acactactat aaggtattat atgtctgatt taaaatctcg tttgattaaa 164940
gcttctactt ctaaattgac tgcagaatta acagcatcta aattctttaa tgaaaaagat 165000
gtagttcgaa caaaaaattcc tatgatgaat attgcacttt ctggtgaaat tactggtggt 165060
atgcaatctg gtctgttaat tttggcaggt ccatcaaaat catttaaatc aaactttgga 165120
ttaacaatgg tgtcatctta catgcgtcaa tatcctgatg cagtatgttt gttttatgat 165180
agtgaatttg gtattactcc tgcttatttg cggtctatgg gagtcgatcc agaacgagta 165240
attcatactc cggttcaatc acttgagcaa ttacgtattg acatggttaa tcaattggat 165300
gcaattgaac gtggcgaaaa ggtagtcgtt tttatcgatt cacttggtaa cttagcttct 165360
aagaaagaaa ctgaagatgc tttaaatgaa aaagttgtta gtgatatgac tagagctaaa 165420
acaatgaaaa gcttatttcg tatcgtaact ccctatttta gtactaaaaa tattccatgt 165480
attgctatta accatacata cgaaacacaa gaaatgttta gtaaaacagt tatgggaggt 165540
ggtactggac cgatgtattc ggctgatact gtattcatta tcggtaaacg tcagattaaa 165600
gatggttctg atcttcaggg gtatcaattt gttctaaatg tagaaaaatc tcgtaccgtt 165660
aaagaaaaaa gtaaattctt tattgatgtt aaatttgacg gtggtatcga tccttattct 165720
ggattgttag atatggctct agaattagga tttgtagtaa aaccaaaaaa tggctggtat 165780
gctcgtgaat ttcttgatga agaaaccggc gagatgattc gcgaagaaaa atcttggcgt 165840
gcaaaagata ccaactgcac tacattctgg ggtcctttat ttaagcatca accattccga 165900
gatgctatta aacgtgctta tcagttaggt gctattgata gtaatgaaat tgttgaagct 165960
gaagtcgacg aattgattaa ctcaaaggtt gaaaaattta aatctccaga aagtaaaagt 166020
aaatcagctg ctgatttaga aactgaccta gaacagttaa gtgatatgga agaatttaat 166080
gaataaagat gatttagatt tagatctaga aattatcgac gaatccccct cttcggaggg 166140
```

ggaagaagaa agaaaagaac gcctttttaa tgaatctctt aagataatta aatctgccat 166200
ggaaaatgtt atccaggaga ttgtcattaa actagaagac ggttctacac acattgtgta 166260
tgtgacaaaa ttagattggg ttgatggaaa agtcgtaatg gactttgctg ttcttgacca 166320
agaaagaaaa gctgagttag ctcctcatgt agaaaaatgt attacaatgc aactacaaga 166380
tgcatttaat aaaaggtcaa agaaaaaatt taaattcttt taaggagtaa gtgtggtaga 166440
aattattctt tcccatctca tatttgatca agcttatttt tcaaaagttt ggccatatat 166500
ggattcagaa tattttgaaa gtggtccagc taaaaataca ttcaaattaa ttaaatctca 166560
tgttaatgag taccatagcg ttccatctat taatgcgtta aatgttgcat tagaaaatag 166620
ttcatttact gaaacagaat attctggtgt aaaaacactt atttcgaaac tagccgattc 166680
tccagaagac catagctggt tagtaaaaga aacagaaaaa tatgttcagc aaagggcgat 166740
gtttaatgct acgtctaaaa taattgaaat tcaaactaat gctgagcttc ctccggaaaa 166800
acgaaataag aaaatgccag atgtaggtgc tattcctgac atcatgcgcc aagcattatc 166860
aatttcattt gatagttacg ttggtcatga ttggatggat gactacgaag cacgttggct 166920
atcttatatg aataaagctc gtaaggttcc atttagactc aaaattctaa ataaaattac 166980
taaaggtgga gctgaaactg gaacactgaa cgttttaatg gctggtgtta acgtcggtaa 167040
gtcattagga ttgtgttcat tggcagcaga ttatttgcag ctcggacata atgttcttta 167100
catttccatg gaaatggcag aagaagtctg tgctaagcgt attgatgcta atatgcttga 167160
tgtttctctt gatgacattg atgacgggca tatttcttac gccgagtata aaggaaaaat 167220
ggaaaaatgg cgtgagaaat ctacccttgg tcgtttaatc gttaagcaat atcctactgg 167280
tggagcagac gctaatacat ttcgatcgct tttaaacgaa ttaaaactca agaagaattt 167340
tgttccaaca atcattattg tcgactatct aggtatttgt aaatcttgcc gcatcagggt 167400
ttactcagaa aatagttaca caactgttaa agctattgca gaggaattgc gtgctcttgc 167460
tgttgaaacc gaaactgttc tttggactgc agcacaggtt ggtaaacaag cttgggattc 167520
ttctgatgtt aacatgagcg atatcgcaga atctgccggt cttccagcaa cagccgattt 167580
tatgcttgca gtcattgaaa ccgaggagtt agcagctgct gaacaacaac tcattaagca 167640
aatcaaatca cgatatggtg ataagaataa atggaataag tttttgatgg gtgttcaaaa 167700
aggaaatcag aaatgggtag aaattgaaca agattctact ccaactgaag tgaacgaagt 167760
agcaggttca cagcagattc aggctgaaca gaatcgctat caaagaaacg aatctgctcg 167820
agctcagtta gatgctttgg caaatgaatt aaaattttag tttacaagcc aacaagacta 167880
tggtatagta gtcttgttgg ttaaatgagg agattgttgt ggaattggta aaggtagttt 167940
ttatggggtg gtttaagaac gaaagcatgt ttactaaaga aatcacaatg atgaaagatg 168000
acgttcaatg ggctactaat caatatgctg aagttaataa agcgctagtt aaagctttca 168060
ttgatgacaa gaaagtatgc gaagtggatt gccgaggata atatgcatat tgttttattt 168120
aaacctactc catataacgt caggaaaaat actcaattca aagcacttat tgcagatacg 168180
tgggaattag tattagatat tccggcagaa gaaagccctc catttggtcg agtggaattt 168240
attaagtttg ctgtgcgccc tacgaagcga cagattcgtc aatgcaaaag atactttcgt 168300
aaaatcgtca agttagagaa acagtttgta acatgtgatt atgcagaagt tttaaaatag 168360
ctgtttactt ttattagaaa ttgagatact ataaacataa actactgagg agattatcat 168420
gaaaaaattt atctttgctg caatttttgc tttatcttct tgcgctgctc agcctgctat 168480

-continued

```
ggcgggttat gacaaagatt tgtgtgaatg gtctatgact gcagatcaga ctgaggttga 168540

aactcaaatt gaagcagata ttatgaatat cgttgagcgt gatcgtcctg aaatgaaagc 168600

tgaagtgcaa aaacaactta agtctggcgg tgtaatgcag tataattatg ttctgtattg 168660

cgataaaaac tttaataata aaaatatcat cgctgaagtg gtaggtgagt aattagaggt 168720

tagtatgtac agttctgaat tttcatattt aaaaatggaa aaaatttcat acgattttat 168780

agatgaaaag gtttattaca gtttccatga accacgtttt aatagtgagg ttgggtttat 168840

tgtagtaaaa gacaatttca ttttaaaaat atattcggca ttaaaggatt ttcactacga 168900

aaatattaac ctaaaatttg ataaagaaaa cgttcgtaat tgtgcagtaa caattacagg 168960

aaataaaggt acatgcgtta tgctatctga tgaaattaat gatttgctaa atgatgcaga 169020

aaaagttgct attccatcga ttgatgacca aatttttaat gcttttatga atagaggtta 169080

atatgaaaac atataaagaa tttattaaag aagatatggt agctggagat tcaggtggta 169140

atcctgaaaa tatctccact ggaacaacgt caggcgctgt agtaaataaa ggtcctgaac 169200

agattcctaa aaagaaaaaa gaggaatcta aagaaaaaga agagtaaaaa tgtcatcaat 169260

accttggatt gataatgagt ttgcgtgccg tgcattggct catttaccta aattcgcaca 169320

agtaaataat agttcaactt ttaaattacg gtttagatgc cctgtttgcg gagattcaaa 169380

aaccgatcaa aataaagccc gtggatggta ttatggcgat aataatgaag gaaatattca 169440

ttgttataac tgtaactatc atgcaccaat tggaatatat ttaaaggagt ttgaacctga 169500

tttatatcgt gagtatatct ttgaaataag aaaagaaaaa ggtaaaagtc gtccagtaga 169560

aaaacctaaa gaacttccta aacagcctga gaagaaaata attaaatctc ttccgtcatg 169620

cattagatta gataaacttg cggaagacca tccaattata aaatatgtaa aagctcgttg 169680

tattccaaag gataaatgga aatatctttg gtttacgacc gaatggc             169727
```

SHIGATOXIN-PRODUCING F18 TYPE *E. COLI* BACTERIOPHAGE ESC-COP-1 AND USE THEREOF FOR INHIBITING PROLIFERATION OF SHIGATOXIN-PRODUCING F18 TYPE *E. COLI*

CROSS-REFERENCE TO RELATED APPLICATIONS

The present application is a U.S. National Phase Application of International Application No. PCT/KR2015/014331, filed Dec. 28, 2015, which claims priority to Korean Application No. 10-2014-0192983, filed Dec. 30, 2014, each of which are hereby incorporated by reference in their entirety.

REFERENCE TO SEQUENCE LISTING

The Sequence Listing submitted Jun. 21, 2017, as a text file named "08162_0032U1_Sequence_Listing.txt," created on May 24, 2017, and having a size of 215,533 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills Shigatoxin-producing type F18 *E. coli*, and a method for preventing and treating the infections of Shigatoxin-producing type F18 *E. coli* using a composition comprising the bacteriophage as an active ingredient. More particularly, the present invention relates to a Myoviridae bacteriophage Esc-COP-1 that is isolated from the nature and can kill specifically Shigatoxin-producing type F18 *E. coli* strains, which has a genome represented by the nucleotide sequence of SEQ. ID. NO: 1 (Accession NO: KCTC 12662BP), and a method for preventing the infections of Shigatoxin-producing type F18 *E. coli* and thereafter treating them using the composition comprising said bacteriophage as an active ingredient.

2. Description of the Related Art

There are two kinds of *Escherichia coli* (*E. coli*): non-pathogenic *E. coli* and pathogenic *E. coli*. The non-pathogenic *E. coli* is normal residential flora in bowels and beneficial to make a balance with other enterobacteria, helping digestion etc. The pathogenic *E. coli* attaches on intestinal wall through pili to proliferate and produces enterotoxins causing diarrhea.

The pathogenic *E. coli* affects various kinds of livestock regardless of ages and gives rise to diarrhea, a notable symptom, possibly leading to high mortality due to dehydration. In Korea, this diarrhea is reported to occur in almost livestock farms. Moreover, in case of mixed infections by Rotavirus, Coronavirus, protozoa Coccidium and the like, this outbreak is stimulated because of damaging enteral mucosa and symptoms is highly aggravated, compared to the case of single infections. There are several pathogenic *E. coli* strains causing diarrhea. Above all, Shigatoxin-producing type F18 *Escherichia coli* is often reported to provoke severe diarrhea and edema in pigs. The Shigatoxin-producing type F18 *E. coli* attaches on intestinal epithelial cells through pili (F18) so as to secrete Shigatoxin. The secreted toxin is absorbed into blood vessels to increase blood pressure and injure arterioles, thereby generating edema in each part of a body and accompanying convulsion, paralysis and the like. Considering a significant damage in livestock industry by the Shigatoxin-producing type F18 *E. coli*, it is urgently requested to develop a method for preventing and treating such infections effectively. A variety of antibiotics have been used to prevent or treat such infections of Shigatoxin-producing type F18 *E. coli*. However, according to the recent rise of antibiotic-resistant bacteria, an efficient alternative is urgently requested.

Recently, the use of bacteriophages has drawn our attention as a new way of treating bacterial infections. Particularly, the reason of our high interest in bacteriophages is because bacteriophage-based treatment is a nature-friendly method. Bacteriophages are an extremely small microorganism that infects bacteria, which are called phage in short. Once bacteriophage infects bacteria, the bacteriophage is proliferated in the inside of the bacterial cell. After full proliferation, the progenies destroy the bacterial cell wall to escape from the host, suggesting that the bacteriophage has bacteria killing ability. The bacteriophage infection is characterized by high specificity, so that a certain bacteriophage infects only a specific bacterium. That is, the bacterium that can be infected by certain bacteriophage is limited, suggesting that bacteriophage can kill only a specific bacterium and cannot harm other bacteria.

Bacteriophage was first found out by an English bacteriologist Twort in 1915 when he noticed that *Micrococcus* colonies melted and became transparent by something unknown. In 1917, a French bacteriologist d'Herelle found out that *Shigella disentriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella Typhi*, and *Vibrio cholerae* have been continuously identified.

Owing to the unique capability of bacteriophage to kill bacteria, bacteriophages have been studied and anticipated as a better method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new anti-bacterial agent that can replace the conventional antibiotics.

Furthermore, the recent regulation of using antibiotics is fortified by the government world-widely. The interest on bacteriophages is increasing more and also industrial applications are increasingly achieved.

Therefore, the present inventors tried to develop a composition applicable for the prevention or treatment of Shigatoxin-producing type F18 *E. coli* infections by using a bacteriophage that is isolated from the nature and can kill Shigatoxin-producing type F18 *E. coli* selectively, and further to establish a method for preventing or treating the infections of Shigatoxin-producing type F18 *E. coli* using the composition. As a result, the present inventors isolated bacteriophages suitable for this purpose and secured the nucleotide sequence of the genome that distinguishes the bacteriophage of the present invention from other bacteriophages. Then, we have developed a composition comprising the isolated bacteriophage as an active ingredient, and confirmed that this composition could be efficiently used for the prevention and treatment of Shigatoxin-producing type F18 *E. coli* infections, leading to the completion of the present invention.

SUMMARY OF THE INVENTION

It is an object of the present invention to provide a Myoviridae bacteriophage Esc-COP-1 that is isolated from the nature and can kill Shigatoxin-producing type F18 *E. coli* specifically, which has the genome represented by the nucleotide sequence of SEQ. ID. NO: 1 (Accession NO: KCTC 12662BP).

It is another object of the present invention to provide a composition applicable for the prevention of Shigatoxin-producing type F18 *E. coli* infections, which comprises the bacteriophage Esc-COP-1 that can infect and kill Shigatoxin-producing type F18 *E. coli*, as an active ingredient and a method for preventing the infections of Shigatoxin-producing type F18 *E. coli* using said composition.

It is another object of the present invention to provide a composition applicable for the treatment of Shigatoxin-producing type F18 *E. coli* infections, which comprises the bacteriophage Esc-COP-1 that can infect and kill Shigatoxin-producing type F18 *E. coli*, as an active ingredient and a method for treating the infections of Shigatoxin-producing type F18 *E. coli* using said composition.

It is another object of the present invention to provide a disinfectant for preventing and treating the infections of Shigatoxin-producing type F18 *E. coli* using said composition.

It is another object of the present invention to provide a drinking water additive for preventing and treating the infections of Shigatoxin-producing type F18 *E. coli* using said composition.

It is also an object of the present invention to provide a feed additive effective upon farming by preventing and treating the infections of Shigatoxin-producing type F18 *E. coli* using said composition.

To achieve the above objects, the present invention provides a Myoviridae bacteriophage ESC-COP-1 that is isolated from the nature and can kill specifically Shigatoxin-producing type F18 *E. coli*, which has the genome represented by the nucleotide sequence of SEQ. ID. NO: 1 (Accession NO: KCTC 12662BP), and a method for preventing and treating the infections of Shigatoxin-producing type F18 *E. coli* using a composition comprising the bacteriophage as an active ingredient. The bacteriophage Esc-COP-1 has been isolated by the present inventors and then deposited at Korean Collection for Type Cultures, Korea Research Institute of Bioscience and Biotechnology in Aug. 21, 2014 (Accession NO: KCTC 12662BP). The present invention also provides a disinfectant, a drinking water additive, and a feed additive applicable for the prevention or treatment of Shigatoxin-producing type F18 *E. coli* infections, which comprises the bacteriophage Esc-COP-1 as an active ingredient.

Since the bacteriophage Esc-COP-1 included in the composition of the present invention kills Shigatoxin-producing type F18 *E. coli* efficiently, it is regarded as effective to prevent or treat *E. coli* diarrhea (infections) caused by Shigatoxin-producing type F18 *E. coli*. Therefore, the composition of the present invention can be utilized for the prevention and treatment of *E. coli* diarrhea caused by Shigatoxin-producing type F18 *E. coli*. In this specification, the *E. coli* diarrhea includes symptoms caused by the *E. coli* infections accompanying fever, diarrhea and the like.

In this description, the term "treatment" or "treat" indicates (i) to suppress the diarrhea caused by Shigatoxin-producing type F18 *E. coli*; and (ii) to relieve the diarrhea caused by Shigatoxin-producing type F18 *E. coli*.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

The pharmaceutically acceptable carrier included in the composition of the present invention is the one that is generally used for the preparation of a pharmaceutical formulation, which is exemplified by lactose, dextrose, sucrose, sorbitol, mannitol, starch, acacia rubber, calcium phosphate, alginate, gelatin, calcium silcate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the present invention can additionally include lubricants, wetting agents, sweeteners, flavors, emulsifiers, suspending agents, and preservatives, in addition to the above ingredients.

In the composition of the present invention, the bacteriophage Esc-COP-1 is included as an active ingredient. At this time, the bacteriophage Esc-COP-1 is included at the concentration of $1\times10^{1}$ pfu/ml~$1\times10^{30}$ pfu/ml or $1\times10^{1}$ pfu/g~$1\times10^{30}$ pfu/g, and preferably at the concentration of $1\times10^{4}$ pfu/ml~$1\times10^{15}$ pfu/ml or $1\times10^{4}$ pfu/g~$1\times10^{15}$ pfu/g.

The composition of the present invention can be formulated by the method that can be performed by those in the art by using a pharmaceutically acceptable carrier and/or excipient in the form of unit dose or in a multi-dose container. The formulation can be in the form of solution, suspension or emulsion in oil or water-soluble medium, extract, powder, granule, tablet or capsule. At this time, a dispersing agent or a stabilizer can be additionally included.

The composition of the present invention can be prepared as a disinfectant, a drinking water additive, or a feed additive according to the purpose of use, but not always limited thereto.

Advantageous Effect

The method for preventing and treating the infections of Shigatoxin-producing type F18 *E. coli* using this composition comprising the bacteriophage Esc-COP-1 as an active ingredient, have the advantage of high specificity to Shigatoxin-producing type F18 *E. coli*, compared with the conventional methods based on the chemical materials including the conventional antibiotics. That means, the composition of the present invention can be used for preventing or treating the infections of Shigatoxin-producing type F18 *E. coli* specifically without affecting other useful residential bacteria, and accordingly has fewer side effects. In general, when chemical materials such as antibiotics are used, the general residential bacteria are also damaged to weaken immunity in animals with carrying various side effects. In the meantime, the composition of the present invention uses the bacteriophage isolated from the nature as an active ingredient, so that it is very nature-friendly.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
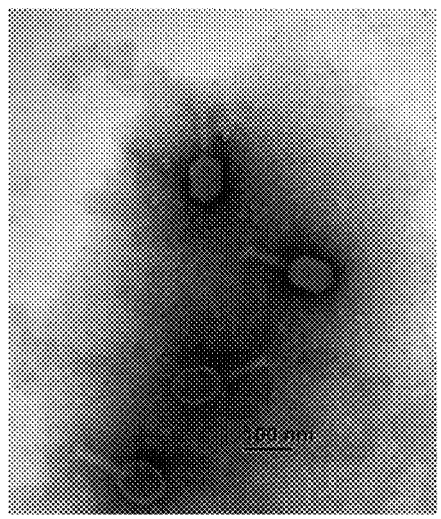
FIG. 1 is an electron micrograph showing the morphology of the bacteriophage Esc-COP-1.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing Shigatoxin-Producing Type F18 *E. coli*

Samples were collected from the nature to screen the bacteriophage capable of killing Shigatoxin-producing type F18 *E. coli*. The Shigatoxin-producing type F18 *E. coli* used for the bacteriophage isolation herein were the one that had been isolated by the present inventors and identified as Shigatoxin-producing type F18 *E. coli* previously.

The isolation procedure of the bacteriophage is described in detail hereinafter. The collected sample was added to the TSB (Tryptic Soy Broth) medium (pancreatic digest of casein, 17 g/L; papaic digest of soybean, 3 g/L; dextrose, 2.5 g/L; sodium chloride, 5 g/L; dipotassium phosphate, 2.5 g/L) inoculated with Shigatoxin-producing type F18 *E. coli* at the ratio of 1/1000, followed by shaking culture at 37° C. for 3~4 hours. Upon completion of the culture, centrifugation was performed at 8,000 rpm for 20 minutes and supernatant was recovered. The recovered supernatant was inoculated with Shigatoxin-producing type F18 *E. coli* at the ratio of 1/1000, followed by shaking culture at 37° C. for 3~4 hours. When the sample contained the bacteriophage, the above procedure was repeated total 5 times in order to increase the titer of the bacteriophage. After repeating the procedure 5 times, the culture solution proceeded to centrifugation at 8,000 rpm for 20 minutes and the resulting supernatant was recovered. The recovered supernatant was filtrated by using a 0.45 μm filter. The obtained filtrate was used in spot assay for examining whether or not the bacteriophage capable of killing Shigatoxin-producing type F18 *E. coli* was included therein.

Spot assay was performed as follows; TSB medium was inoculated with Shigatoxin-producing type F18 *E. coli* at the ratio of 1/1000, followed by shaking culture at 37° C. for overnight. 3 ml (1.5 of $OD_{600}$) of the culture broth of Shigatoxin-producing type F18 *E. coli* prepared above was spread on the TSA (Tryptic Soy Agar; pancreatic digest of casein, 17 g/L; papaic digest of soybean, 3 g/L; sodium chloride, 5 g/L; agar, 15 g/L) plate. The plate stood in a chamber for about 30 minutes to dry. After drying, 10 μl of the resulting filtrate was spotted directly onto the surface of the Shigatoxin-producing type F18 *E. coli* lawns and dried for about 30 minutes. Following drying, the plate was incubated at 37° C. for a day and then, examined for the formation of clear zones on the surface of the bacterial lawns. If a clear zone was generated where the filtrate was dropped, it could be judged that the bacteriophage capable of killing Shigatoxin-producing type F18 *E. coli* was included in the filtrate. Through the above procedure, the filtrate containing the bacteriophage having the killing ability of Shigatoxin-producing type F18 *E. coli* could be obtained.

After that, the bacteriophage was isolated from the filtrate confirmed above to have the bacteriophage capable of killing Shigatoxin-producing type F18 *E. coli*. The conventional plaque assay was used for the isolation of pure bacteriophages. In detail, a plaque formed in the course of the plaque assay was picked up by using a sterilized tip, which was then added to the culture solution of Shigatoxin-producing type F18 *E. coli*, followed by culturing for 4~5 hours. Upon completion of the culture, centrifugation was performed at 8,000 rpm for 20 minutes to obtain supernatant. The recovered supernatant was inoculated with Shigatoxin-producing type F18 *E. coli* culture at the ratio of 1/50, followed by culturing again for 4~5 hours. To increase the titer of the bacteriophage, the above procedure was repeated at least 5 times. Then, centrifugation was performed at 8,000 rpm for 20 minutes to obtain supernatant. Plaque assay was performed with the obtained supernatant. In general, the pure bacteriophage isolation is not completed by one-time procedure, so the above procedure was repeated by using the plague formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by the observation under electron microscope. Until the pure bacteriophage isolation was confirmed under electron microscope, the above procedure was repeated. The observation under electron microscope was performed by the conventional method. Briefly, the solution containing the pure bacteriophage was loaded on copper grid, followed by negative staining with 2% uranyl acetate. After drying thereof, the morphology was observed under transmission electron microscope. The electron micrograph of the bacteriophage isolated in the present invention is presented in FIG. 1. From the morphological observation, the bacteriophage isolated above was identified as belonging to the family Myoviridae.

The solution containing the pure bacteriophage confirmed above proceeded to purification. The culture broth of Shigatoxin-producing type F18 *E. coli* was added to the solution containing the pure bacteriophage at the volume of 1/50 of the total volume of the bacteriophage solution, followed by culturing again for 4~5 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 ml of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was resuspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Esc-COP-1 and then deposited at Korean Collection for Type Cultures, Korea Research Institute of Bioscience and Biotechnology in Aug. 21, 2014 (Accession NO: KCTC 12662BP).

Example 2: Separation and Sequence Analysis of the Bacteriophage Esc-COP-1 Genome The genome of the bacteriophage Esc-COP-1 was separated as follows. The genome was separated from the bacteriophage suspension obtained in Example 1. First, in order to eliminate DNA and RNA of Shigatoxin-producing type F18 *E. coli* included in the suspension, DNase I and RNase A were added 200 U each to 10 ml of the bacteriophage suspension, which was incubated at 37° C. for 30 minutes. 30 minutes later, to remove the DNase I and RNase A activity, 500 μl of 0.5 M ethylenediaminetetraacetic acid (EDTA) was added thereto, which was incubated for 10 minutes. The suspension was further incubated at 65° C. for 10 minutes and then added with 100 μl of proteinase K (20 mg/ml) to break the outer wall of the bacteriophage, followed by incubation at 37° C. for 20 minutes. After that, 500 μl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the bacteriophage Esc-COP-1 genome.

The nucleotide sequence of the genome of the bacteriophage Esc-COP-1 obtained above was analyzed by Next Generation Sequencing (NGS) using illumina Mi-Seq device at National Instrumentation Center for Environmental Management, Seoul National University. As a result, it is suggested that the final genome of bacteriophage Esc-COP-1 has 169,727 bp of size and the nucleotide sequence of the whole genome has SEQ. ID. NO: 1.

Similarity of the genomic sequence of the bacteriophage Esc-COP-1 obtained above with the previously reported bacteriophage genome sequences was investigated by using BLAST. From the BLAST result, it is confirmed that the genomic sequence of the bacteriophage Esc-COP-1 has high-sequence homologies with the sequences of *E. coli* bacteriophage vB_EcoM_ACG-C40 (Genbank Accession NO: JN986846.1), *E. coli* bacteriophage RB14 (Genbank Accession-NO: FH839692.1), *E. coli* bacteriophage HY01 (Genbank Accession NO: KF925357.1), *E. coli* bacteriophage RB51 (Genbank Accession NO: FJ839693.1) and *E. coli* bacteriophage RB68 (Genbank Accession NO: KM607004. 1) (96%, 96%, 97%, 95% and 95%). However, their genome sizes were discriminated one another. Precisely, the whole genome of bacteriophage Esc-COP-1 was determined to have 169,727 bp of size, while whole genome of *E. coli* bacteriophage vB_EcoM_ACG-C40 had 167,396 bp of size, that of *E. coli* bacteriophage RB14 had 165,429 bp of size, that of *E. coli* bacteriophage HY01 had 166,977 bp of size, that of *E. coli* bacteriophage RB51 had 168,394 bp of size and that of *E. coli* bacteriophage RB68 had 168,401 bp of size distinctly. Furthermore, the number of ORFs (Open Reading Frame) within the genome of bacteriophage Esc-COP-1 was determined to 275 ORFs, while the number of ORFs within *E. coli* bacteriophage vB_EcoM_ACG-C40 was 273 ORFs, that of *E. coli* bacteriophage RB14 was 274ORFs, that of *E. coli* bacteriophage HY01 was 257 ORFs, and that of *E. coli* bacteriophage RB68 was 276 ORFs distinctly. But the number of ORFs within the genome of *E. coli* bacteriophage RB51 was 275 ORFs, which was same with that of bacteriophage Esc-COP-1. Nevertheless, the ORFs arrangement within the genome of *E. coli* bacteriophage RB51 was very different from that of bacteriophage Esc-COP-1.

Based upon this result, it is concluded that the bacteriophage Esc-COP-1 should be a novel bacteriophage never reported previously.

Example 3: Investigation of Killing Ability of the Bacteriophage Esc-COP-1 Against Shigatoxin-Producing Type F18 *E. coli*

Figure 2:
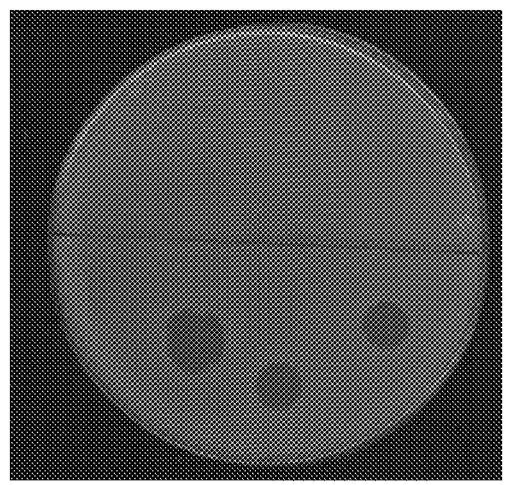
FIG. 2 is a photograph illustrating the capability of the bacteriophage Esc-COP-1 to kill Shigatoxin-producing type F18 *E. coli*. The clear zone on the dish is the formation of plaque by lysis of bacteria cells.

The killing ability of the isolated bacteriophage Esc-COP-1 against Shigatoxin-producing type F18 *E. coli* was investigated. To do so, the formation of clear zone was observed by the spot assay by the same manner as described in Example 1. The Shigatoxin-producing type F18 *E. coli* used for this investigation were total 10 strains which had been isolated and identified as Shigatoxin-producing type F18 *E. coli* previously by the present inventors. The bacteriophage Esc-COP-1 demonstrated the killing ability against 9 strains of the Shigatoxin-producing type F18 *E. coli* used in this experiment. The representative result of the killing ability test is shown in FIG. 2. In the meantime, the activity of the bacteriophage Esc-COP-1 to kill *Staphylococcus aureus, Enterococcus faecalis, Enterococcus faecium, Lactobacillus plantarum, Streptococcus uberis* and *Pseudomonas aeruginosa* was also investigated. As a result, it is decided that the bacteriophage Esc-COP-1 did not have the killing activity against these microorganisms.

Therefore, it was confirmed that the bacteriophage Esc-COP-1 has the specific ability to kill Shigatoxin-producing type F18 *E. coli* and a broad antibacterial spectrum against Shigatoxin-producing type F18 *E. coli*, suggesting that the bacteriophage Esc-COP-1 of the present invention could be used as an active ingredient of the composition for preventing and treating the infections of Shigatoxin-producing type F18 *E. coli*.

Example 4: Preventive Effect of Bacteriophage Esc-COP-on the Infections of Shigatoxin-Producing Type F18 *E. coli*

100 μl of the bacteriophage Esc-COP-1 solution at $1\times10^8$ pfu/ml was added to a tube containing 9 ml of TSB. To another tube containing 9 ml of TSB, only the same volume of TSB was added. Then, the Shigatoxin-producing type F18 *E. coli* culture was added to each tube to prepare bacterial suspension in 0.5 of $OD_{600}$. After that, the tubes were transferred to an incubator at 37° C., followed by shaking culture, during which the growth of Shigatoxin-producing type F18 *E. coli* was observed. As presented in Table 1, the growth of Shigatoxin-producing type F18 *E. coli* was inhibited in the tube added with the bacteriophage Esc-COP-1 solution, while the growth of Shigatoxin-producing type F18 *E. coli* was not inhibited in the tube without the bacteriophage Esc-COP-1 solution.

TABLE 1

| Inhibition of growth of Shigatoxin-producing type F18 *E. coli* | | | |
|---|---|---|---|
| | $OD_{600}$ | | |
| item | Culturing 0 min. | Culturing 60 min. | Culturing 120 min. |
| (−) bacteriophage solution | 0.5 | 1.5 | 2.1 |
| (+) bacteriophage solution | 0.5 | 0.4 | 0.3 |

The above results indicate that the bacteriophage Esc-COP-1 not only inhibited the growth of Shigatoxin-producing type F18 *E. coli* but also could kill them. Therefore, the bacteriophage Esc-COP-1 can be used as an active ingredient of the composition for preventing the infections of Shigatoxin-producing type F18 *E. coli*.

Example 5: Therapeutic Effect of Bacteriophage Esc-COP-1 on the Infections of Shigatoxin-Producing Type F18 *E. coli*

Therapeutic effect of the bacteriophage Esc-COP-1 on animals affected by Shigatoxin-producing type F18 *E. coli* was investigated. 4 weaning pigs at 25 days of age were grouped together; total 2 groups of pigs were raised in a pig pen (1.1 m×1.0 m) for 14 days. Heating system was furnished and the surrounding environment was controlled. The temperature and the humidity of the pig pen were controlled and the floor was cleaned every day. On the $7^{th}$ day of the experiment, all the animals were orally administered with 1 mL of Shigatoxin-producing type F18 *E. coli* suspension using an oral injection tube. The Shigatoxin-producing type F18 *E. coli* suspension administered above was prepared as follows: Shigatoxin-producing type F18 *E. coli* was cultured in TSB medium at 37° C. for 18 hours and the bacterial cells were collected by centrifugation. Saline (pH 7.2) was added to the bacterial cell pellet to make cell suspension at a concentration of $10^9$ CFU/ml. From the next day of the Shigatoxin-producing type F18 *E. coli* challenge, the experimental group (bacteriophage solution treated pigs) were orally administered with the bacteriophage Esc-COP-1 ($10^9$ PFU/head) via the same way as used for the above administration twice a day. The control group (bacteriophage solution non-treated pigs) was treated with nothing. Feeds and drinking water were equally provided to both groups. After the challenge of Shigatoxin-producing type F18 *E. coli*, all the animals were observed every day whether or not they experienced diarrhea. The observation was performed by measuring the diarrhea index. The diarrhea index was set as follows according to Fecal Consistency (FC) score (normal: 0, loose stool: 1, moderate diarrhea: 2, and severe diarrhea: 3). The results are shown in Table 2.

TABLE 2

| Fecal Consistency score | | | | | | | | |
|---|---|---|---|---|---|---|---|---|
| | Days after Shigatoxin-producing type F18 *E. coli* challenge | | | | | | | |
| | 0 | 1 | 2 | 3 | 4 | 5 | 6 | 7 |
| Control group (− bacteriophage solution) | 2.25 | 2.5 | 2.5 | 2.25 | 2 | 2 | 1.5 | 1.5 |
| Experimental group (+ bacteriophage solution) | 2.5 | 1.75 | 1 | 0.5 | 0.25 | 0.25 | 0 | 0 |

From the above results, it is confirmed that the bacteriophage Esc-COP-1 of the present invention could be very effective to treat the infections of Shigatoxin-producing type F18 *E. coli*.

Example 6: Preparation of Feed Additives and Feeds

Feed additive containing bacteriophage Esc-COP-1 at a concentration of $1\times10^8$ pfu/g was prepared using the bacteriophage Esc-COP-1 solution. The preparation method thereof was as follows: Maltodextrin (40%, w/v) was added to the bacteriophage solution and then, trehalose was added to reach 10% of final concentration. After mixing well, the mixture was freeze-dried. Lastly, the dried mixture was grinded into fine powders. The drying process above can be replaced with vacuum-drying, drying at warm temperature, or drying at room temperature. To prepare the control feed additive for comparison, feed additive that did not contain the bacteriophage but contained buffer (10 mM Tris-HCl, 10 mM $MgSO_4$, 0.1% Gelatin, pH 8.0) only was prepared.

The above two kinds of feed additives were mixed with the 1,000 times volume of feed for pig farming respectively, resulting in two kinds of final feeds.

Example 7: Preparation of Drinking Water Additives and Disinfectants

Drinking water additive and disinfectant are different in intended use but same in the composition, so they have been prepared by the same manner. Drinking water additive (or disinfectant) containing bacteriophage Esc-COP-1 at a concentration of $1\times10^8$ pfu/ml was prepared using the bacteriophage Esc-COP-1 solution. Particularly, to prepare drinking water additive (or disinfectant), the bacteriophage ESC-COP-1 solution was added to buffer solution to reach $1\times10^8$ pfu/ml, which was mixed well. For the comparison, the above buffer solution itself was used as the drinking water additive (or disinfectant) that did not contain the bacteriophage.

The prepared two kinds of drinking water additives (or disinfectants) were diluted in water at the ratio of 1:1000, and then used as drinking water or disinfectant.

Example 8: Effect on Pig Farming

The effect of the feeds, drinking water, and disinfectant prepared in Example 6 and Example 7 on pig farming was investigated. Particularly, the investigation was focused on diarrhea conditions by fecal consistency score used in Example 5. Total 30 piglets were grouped into three groups, and each group was composed of 10 piglets (group A: feed test group, group B: drinking water test group; and group C: disinfectant test group). The experiment was continued for 2 weeks. Each group was divided by two sub-groups comprising 5 piglets each. The sub-groups were divided according to the treatment of the bacteriophage Esc-COP-1 or not (sub-group-①: treated with the bacteriophage Esc-COP-1; and sub-group-②: not-treated with the bacteriophage). The piglets used in this experiment were weaning pigs at 20 days of age and raised in a separated room placed at a sufficient distance from each other. Each sub-group was divided and named as shown in Table 3.

TABLE 3

Sub-groups of pig farming experiment

| Item | Sub-group: Treated with the bacteriophage Esc-COP-1 | Sub-group: Not-treated with the bacteriophage |
|---|---|---|
| Fed with feeds | A-① | A-② |
| Provided with drinking water | B-① | B-② |
| Treated with disinfectant | C-① | C-② |

Feeds were provided according to the conventional feed supply method as presented in Table 3 with the feeds prepared in Example 6. Drinking water was provided according to the conventional water supply method as presented in Table 3 with the drinking water prepared in Example 7. Disinfectant was treated three times a week with taking turns with the conventional disinfectant. That is, on the day when the disinfectant of the present invention was sprayed, the conventional disinfectant was not treated. The results are shown in Table 4.

TABLE 4

Fecal consistency score of pig farming experiment

| Group | Fecal consistency score | | | | | | | | | | | | | |
|---|---|---|---|---|---|---|---|---|---|---|---|---|---|---|
| 그룹 | d1 | d2 | d3 | d4 | d5 | d6 | d7 | d8 | d9 | d10 | d11 | d12 | d13 | d14 |
| A-① | 0 | 0 | 0.2 | 0.2 | 0 | 0 | 0 | 0.2 | 0.2 | 0 | 0 | 0 | 0.2 | 0 |
| A-② | 0 | 0.2 | 0.4 | 0.4 | 0.2 | 0.2 | 0.2 | 0.4 | 0.4 | 0.4 | 0.4 | 0.2 | 0.2 | 0.2 |
| B-① | 0.2 | 0 | 0 | 0 | 0 | 0 | 0.2 | 0 | 0 | 0 | 0 | 0.2 | 0 | 0 |
| B-② | 0.2 | 0.2 | 0.2 | 0.4 | 0.4 | 0.4 | 0.2 | 0.2 | 0.4 | 0.4 | 0.2 | 0.4 | 0.4 | 0.2 |
| C-① | 0.2 | 0.2 | 0 | 0 | 0 | 0.2 | 0.2 | 0.2 | 0 | 0 | 0.2 | 0 | 0 | 0 |
| C-② | 0 | 0.2 | 0.2 | 0.2 | 0.4 | 0.4 | 0.2 | 0.4 | 0.4 | 0.2 | 0.2 | 0.2 | 0.2 | 0.4 |

From the above results, it is confirmed that the feeds, drinking water, and the disinfectant prepared according to the present invention were effective in reducing the animal diarrhea. Therefore, it is concluded that the composition of the present invention could be efficiently applied for the improvement of productivity of animal farming.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for preventing or treating infections of Shigatoxin-producing type F18 *E. coli*, the method comprising a step of administering to a subject a composition comprising Myoviridae bacteriophage Esc-COP-1 (Accession NO: KCTC 12662BP) that is isolated from nature and can kill Shigatoxin-producing type F18 *E. coli* specifically, which has the genome represented by the nucleotide sequence of SEQ ID NO: 1, as an active ingredient.

2. The method according to claim 1, wherein said composition is administered to the subject in the form of a feed additive, a drinking water additive, or a disinfectant.

* * * * *